United States Patent [19]

Spitz, Jr. et al.

[11] 4,446,651

[45] May 8, 1984

[54] METHOD OF INCREASING EXTRACTABLE CEDARWOOD OIL FROM JUNIPERUS MEXICANA

[75] Inventors: Seymour J. Spitz, Jr., New York, N.Y.; Braja D. Mookherjee, Holmdel, N.J.; Ira D. Hill, Locust, N.J.; Lloyd F. Keleher, Rumson, N.J.; Robert W. Trenkle, Bricktown, N.J.; Robin K. Wolff, Point Pleasant, N.J.

[73] Assignee: International Flavors & Fragrances Inc., New York, N.Y.

[21] Appl. No.: 409,701

[22] Filed: Aug. 19, 1982

Related U.S. Application Data

[63] Continuation-in-part of Ser. No. 399,068, Jul. 16, 1982, abandoned.

[51] Int. Cl.³ ............................................. A01G 23/10
[52] U.S. Cl. ........................................ 47/10; 47/57.5; 71/92
[58] Field of Search .................................... 47/10–12, 47/58, 57.5; 71/92

[56] References Cited

U.S. PATENT DOCUMENTS

| | | | |
|---|---|---|---|
| 1,636,550 | 7/1927 | Buel | 426/430 |
| 2,665,196 | 1/1954 | Poffenberger | 422/259 |
| 3,542,755 | 11/1970 | Tiemstra | 260/118 |
| 3,839,823 | 10/1974 | Roberts et al. | 47/10 |
| 3,971,159 | 7/1976 | Brown et al. | 47/10 |
| 4,176,495 | 12/1979 | Dale | 47/57.5 |
| 4,201,566 | 5/1980 | O'Neal | 71/92 |
| 4,203,253 | 5/1980 | Wolter et al. | 47/10 |
| 4,313,912 | 2/1982 | Barger | 422/267 |

FOREIGN PATENT DOCUMENTS

1324361  7/1973  United Kingdom .

OTHER PUBLICATIONS

Attempt to Induce Lightwood, Kiatgrajai et al., Jul. 1976, Wood Science, vol. 9, No. 1, p. 31.
Chemically Inducing Lightwood, Roberts et al., Jun. 1977, Forest Prod. Journ., vol. 27, No. 6, p. 28.
Developments in Paraquat, Drew et al., Jul. 1977, Forest Prod. Journ., vol. 27, No. 7, p. 43.
Paraquat Treatment, Sandberg et al., Jul. 1977, Wood Science, vol. 10, No. 1, p. 28.
Lightwood Formation; Wroblewska et al., Jul. 1977, Wood Science, vol. 10, No. 1, p. 1.

*Primary Examiner*—Robert E. Bagwill
*Attorney, Agent, or Firm*—Arthur L. Liberman

[57] ABSTRACT

Described is a method of chemically increasing the amount of extractable cedarwood oil from Juniperus Mexicana (commonly known as "Texas cedarwood") by treating standing living Juniperus Mexicana with a solution comprising a bipyridylium salt and permitting said trees to continue to grow in their natural environment for a period of time of at least two months. Portions of the trees are then cut and the cedarwood oil is extracted therefrom using unit operations including, but not limited to, steam distillation, in relatively large yields.

12 Claims, 68 Drawing Figures

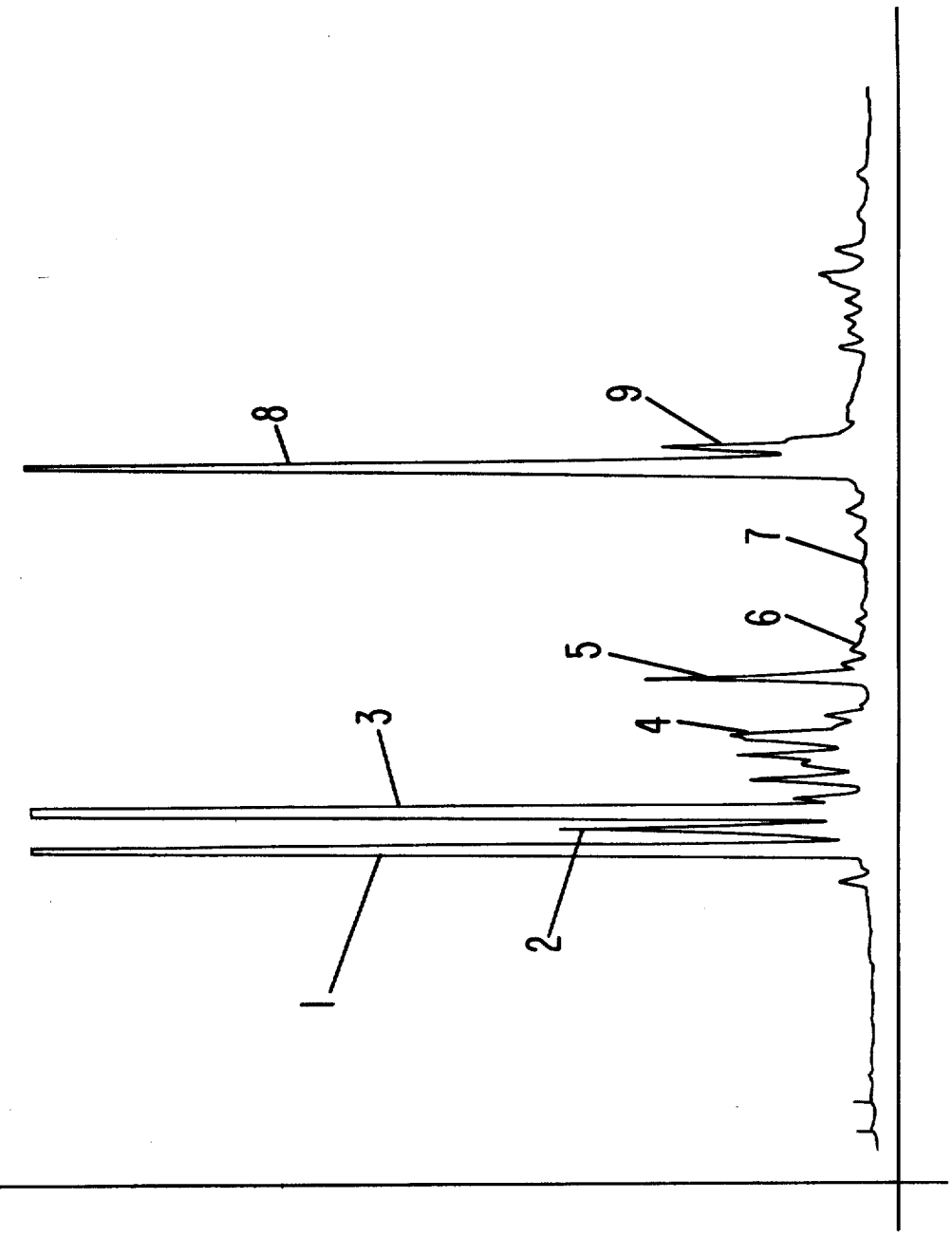

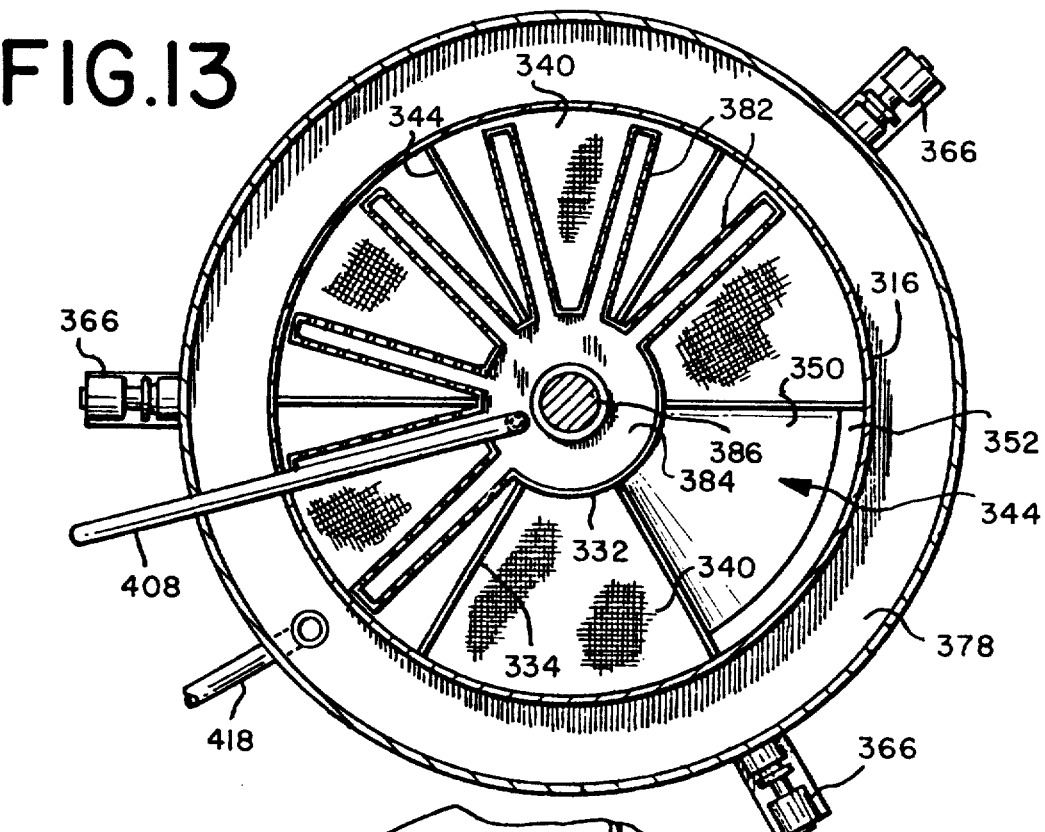
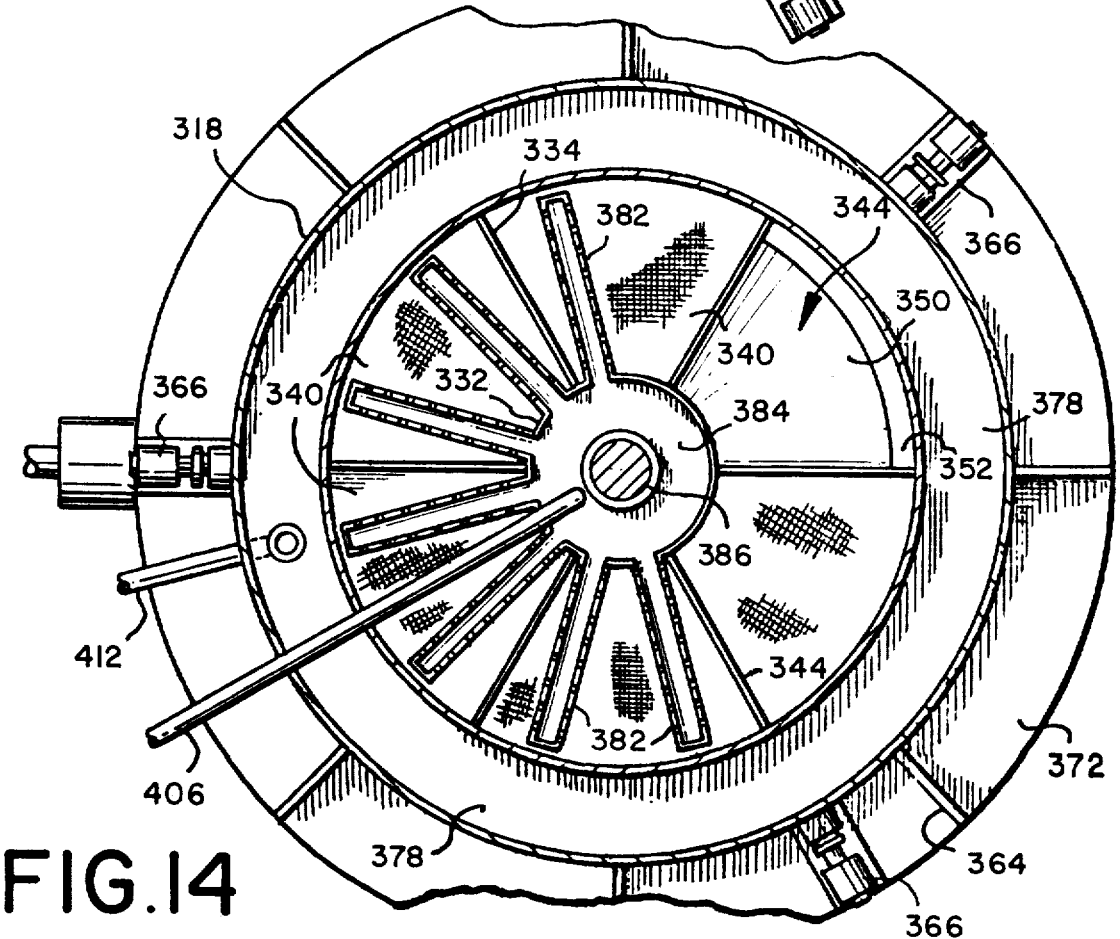

FIG.26
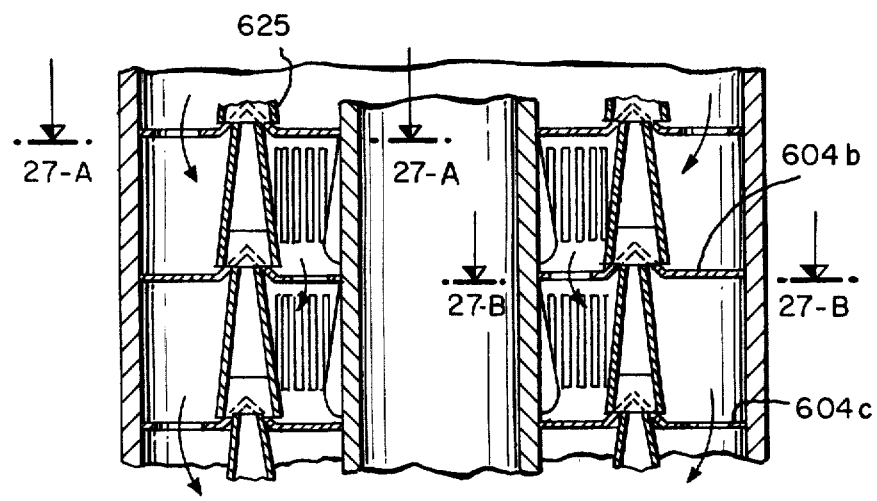
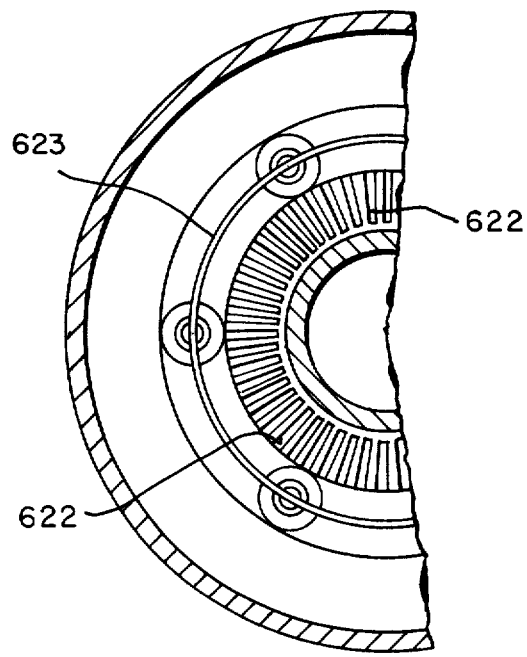
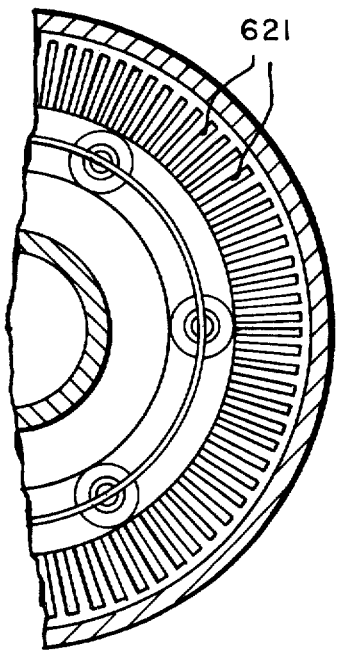
FIG.27-A    FIG.27-B

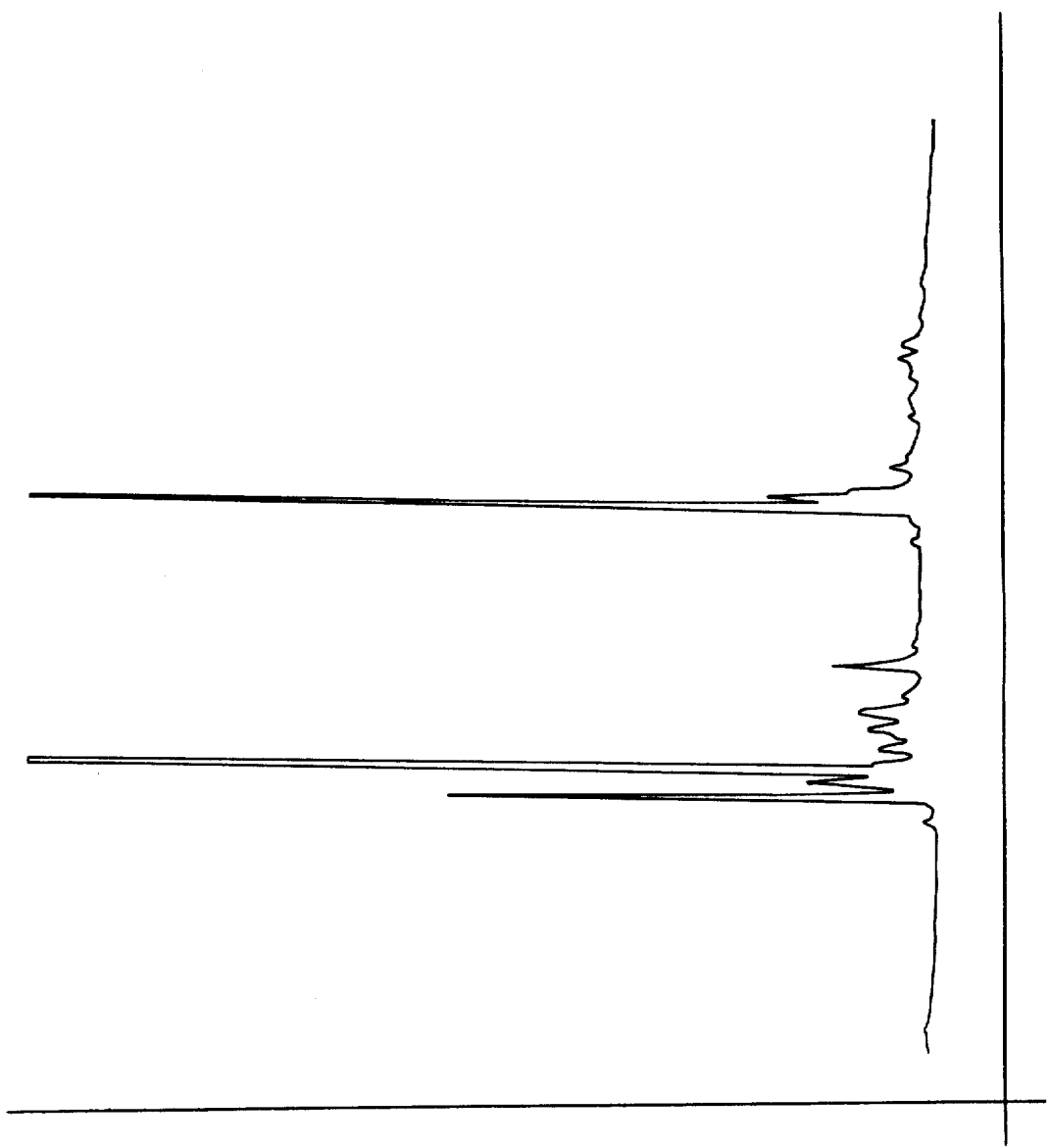
FIG. 28 GLC PROFILE FOR EXAMPLE I A.

IR SPECTRUM FOR EXAMPLE IA.

FIG. 30 GLC PROFILE FOR EXAMPLE I B.

IR SPECTRUM FOR EXAMPLE I B.

GLC PROFILE FOR EXAMPLE I C.
CRUDE

IR SPECTRUM FOR EXAMPLE I C.

GLC PROFILE FOR EXAMPLE II A.

FIG. 36 GLC PROFILE FOR EXAMPLE II B.

FIG. 37 GLC PROFILE FOR EXAMPLE II A.

GLC PROFILE FOR EXAMPLE II D.

GLC PROFILE FOR EXAMPLE II E.

GLC PROFILE FOR EXAMPLE II F.

GLC PROFILE FOR EXAMPLE II G.

GLC PROFILE FOR EXAMPLE II H.

GLC PROFILE FOR EXAMPLE II J.

FIG.44 GLC PROFILE FOR EXAMPLE II K.

GLC PROFILE FOR EXAMPLE III A.

GLC PROFILE FOR EXAMPLE III B.

FIG. 47  GLC PROFILE FOR EXAMPLE III C.

FIG. 48 — GLC PROFILE FOR EXAMPLE IIID.

FIG.50 GLC PROFILE FOR EXAMPLE IIIF.

FIG. 51 GLC PROFILE FOR EXAMPLE III G.

GLC PROFILE FOR EXAMPLE III J.

FIG.54 GLC PROFILE FOR EXAMPLE III K.

METHOD OF INCREASING EXTRACTABLE CEDARWOOD OIL FROM JUNIPERUS MEXICANA

This application is a continuation-in-part of application for U.S. Letters Patent Ser. No. 399,068 filed on July 16, 1982 and now abandoned.

BACKGROUND OF THE INVENTION

Texas cedarwood oil, a material having a high thujopsene content is a natural product of "Texas cedarwood" trees otherwise properly known as *Juniperus Mexicana*. The oil of *Juniperus Mexicana* ranks among one of the more highly utilized essential oils and it enjoys the steady interest of perfumers and an increasing interest of the manufacturers of aromatic chemicals. *Juniperus Mexicana* grows abundantly in the southwestern parts of Texas, toward the south in Mexico and Central America. The cedarwood oil is generally steam distilled from the heartwood of this tree which is filled substantially exclusively for the purpose of producing the essential oil. The crude oil is a viscous liquid having an odor which is pleasant, sweet woody jet somewhat tar-like or cade-like and smoky. On drying it becomes increasingly balsamic-sweet and shows a great tenacity with a uniform sweet, woody dry-out. The rectified oil of *Juniperus Mexicana* is pale yellow to colorless. Its odor is less tar-like, less cade-like or smoky than that of the crude oil. The dry-out is clean, sweet, woody with a typical "pencil sharpener" odor. It is customary to fractionate the crude oil during the redistillation according to Arctander, "Perfume and Flavor Materials of Natural Origin" at column 144 and 145, a "light" fraction consists mainly of sesquiterpenes and it presents the dry-woody part of the cedarwood notes. The "heavy" fractions consist mainly of cedrol. These sesquiterpene alcohols can be isolated in a more or less pure state from the resulting product. They are solid materials of weak, but very pleasant, woody-balsamic aromas.

In an effort to conserve growing areas for *Juniperus Mexicana*, it has become commercially feasible to cause the Juniperus Mexicana to yield a larger quantity of cedarwood oil having the same chemical constituency as that yielded ordinarily by *Juniperus Mexicana*.

Accordingly, the present invention relates to a method of chemically increasing the amount of thujopsene-containing cedarwood oil extractable from the wood of *Juniperus Mexicana* by treating living growing *Juniperus Mexicana* with solutions containing, but not necessarily limited to, bipyridylium salts, continuing to permit the *Juniperus Mexicana* to grow for a period of at least two months and then cutting all or sections of said *Juniperus Mexicana* and extracting the resulting high thujopsene-containing cedarwood oil from the wood.

The prior art has shown that such bipyridylium compounds can induce increased production of materials such as oleoresin materials. Thus, U.S. Pat. No. 4,201,566 issued May 6, 1980, the disclosure of which is incorporated by reference herein, discloses a method of chemically increasing the amount of extractable oleoresinous and tall oil material from pine wood by treating severed living portions of pine trees with a dilute solution of a bipyridylium salt and storing the treated wood for a period of approximately 3-30 days. It is stated in said U.S. Pat. No. 4,201,566 that the living portions of pine trees may be in the form of tree boles from felled trees, stems, twigs, roots or needles and chips, shavings or sawdust thereof.

It has also been shown that bipyridylium compounds can induce increased production of oleoresin material in living, standing pine trees. Thus, Roberts, et al U.S. Pat. No. 3,839,823 issued Oct. 8, 1974, the specification of which is incorporated herein by reference, states that the living tree may typically be treated with a chemical solution by applying the solution to a treatment site on the living tree. Treatment sites are prepared by various methods such as: removing a small section of bark to expose sapwood, making an ax cut deep enough to expose sapwood or by boring a small, downwardly sloping hole into the sapwood. Also pertinent is U.S. Pat. No. 2,971,159, the specification of which is incorporated by reference herein. It is taught in said U.S. Pat. Nos. 3,839,823 and 4,201,566 that the purpose of these treatment sites is to permit the chemical solution, e.g. the solution of bipyridylium salts, to be adsorbed into the living cells of the tree. Once applied to a living tree, the chemical is mobile and may be carried to distant areas within the tree. The chemical, once absorbed into the living cells of the bark and wood (xylem), induces the cells to produce and secrete copious amounts of oleoresin into other adjacent wood fibers until the wood becomes resin or "pitch" soaked. At least some of the carbon necessary to carry out the synthesis of the oleoresins comes from sugars and other substrates ultimately produced by photosynthesis in the leaves of the living tree. In this manner, the oleoresin production of a living tree may, after a period of from 6–12 months following treatment, be increased manyfold. Following the treatment period, the tree must be felled and the heavy "pitch" soaked portions are then transported to an extraction plant where the oleoresins and tall oil components are extracted from the wood using methods well known in the art.

More specifically, U.S. Pat. No. 4,176,495, issued Dec. 4, 1979, the specification of which is incorporated by reference herein, discloses an apparatus and method for drilling a borehole, into the sapwood of a tree and injecting such chemical solution as bipyridylium salts into the borehole, preferably during withdrawal of the drill bit, including facilities for supplying a liquid through a passageway within the bit and facilities for injecting a quantity of liquid proportional to the volume of the borehole and allocated simultaneously with and in response to progression of the drill bit into the borehole as the drill bit is being withdrawn therefrom.

Bipyridylium salts have been used and taught to be useful in the prior art for lightwood formation in red pine and northwest conifers as shown in:

(a) Wroblewska, et al "Lightwood Formation in Red Pine Treated With Paraquat" *Wood Science*, Volume 10, Number 1, July 1977, page 1.

(b) Lightwood et al "Paraquat Treatment of Northwest Conifers for Lighwood Induction" *Wood Science*, Volume 10, Number 1, July 1977, page 28.

(c) Roberts and Peters "Chemically Inducing Lightwood Formation in Southern Pines" *Forest Products Journal*, Volume 27, Number 6, June 1977, page 28.

(d) Drew and Roberts "Developments in Paraquat Treatment of Trees to Induce Lightwood Formation" *Forest Products Journal*, Volume 27, Number 7, July 1977, page 43.

(e) Kiatgrajai, et al "Attempt to Induce Lightwood in Balsam Fir and Tamarack by Treating with Paraquat" *Wood Science*, Volume 9, Number 1, July 1976, Page 31.

In addition, other processes for increasing oleoresin synthesis in pinus species are set forth in, for example, Wolter, et al., U.S. Pat. No. 4,203,253 issued May 20, 1980, wherein it is disclosed that stimulation of oleoresin production associated with living cells can be chemically induced with dilute systemic application of ethylene or ethylene-releasing compounds taken in combination with bipyridylium salts. Disclosed is the fact that one such ethylene-releasing compound is 2-chloroethylphosphonic acid. It is further stated in U.S. Pat. No. 4,203,253, the specification of which is incorporated by reference herein, that oleoresin production can be accomplished by using ethylene-releasing chemicals in combination with the bipyridylium salts, diquat or paraquat.

A specifically disclosed technique for preparing a treatment site on the hole of a conifer useful in conjunction with the instant application for U.S. Letters Patent is set forth in U.S. Pat. No. 3,971,159 issued on July 27, 1976, the specification of which is incorporated by reference herein.

OBJECTS OF THE INVENTION

It is an object of this invention to induce a multiplefold increase in the production of high thujopsene-content cedarwood oil by means of appropriate treatment of Juniperus Mexicana during growth using bipyridylium salts.

Another object of this invention is to optimize the process variables for obtaining a maximum amount of cedarwood oil from 15-20 foot tall, 20-30 year old Juniperus Mexicana trees by treatment thereof using bipyridylium salts defined according to one of the structures:

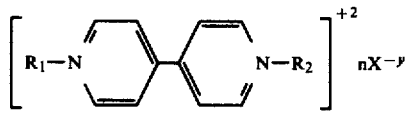

or

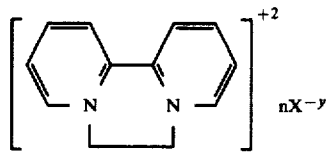

wherein $R_1$ and $R_2$ are the same or different and each represents $C_1$-$C_4$ lower alkyl; wherein $n=1$, $y=1$ and the product of n and y is 2 and wherein X represents chloride, bromide, fluoride, iodide, sulfate, nitrate, hydroxyl or methyl sulfate.

SUMMARY OF THE INVENTION

The invention discloses a new method of inducing formation in high yields of high thujopsene-content cedarwood oil within the heartwood of Juniperus Mexicana trees as a result of applying a bipyridylium salt to a portion or portions of said Juniperus Mexicana. The chemicals used are a class of substituted bipyridylium (bipyridinium) salts defined according to one of the structures:

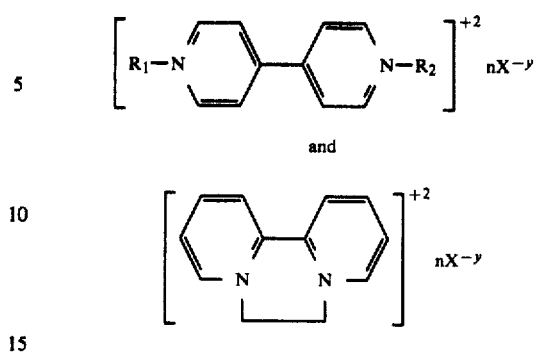

wherein $R_1$ and $R_2$ are the same or different and each represents $C_1$-$C_4$ lower alkyl; wherein $n=1$, $y=1$ and the product of n and y is 2 and wherein X represents chloride, bromide, fluoride, iodide, sulfate, nitrate, hydroxyl or methyl sulfate.

By this method, high thujopsene-containing cedarwood oil containing various terpene hydrocarbons including alpha-cedrene, beta-cedrene, alpha-chamigrene, thujopsene, cuparene, iso-laurene, delta-cadinol, cedrol and widdrol are deposited and stored in the heartwood of various sections of the *Juniperus Mexicana*. After tree harvesting, the resulting high thujopsene-containing cedarwood oil products are produced from the particularized tree wood (e.g. chips).

The bipyridylium salts can be applied to the leaves of the tree, as by spraying, or by means of impregnation through a drilled elongated hole in the hole or base of the tree or elsewhere in accordance with U.S. Pat. No. 3,971,159 issued on July 27, 1976, the specification of which is incorporated by reference herein.

The bipyridylium salt is applied during the growth stage of the *Juniperus Mexicana*. Subsequent to application the *Juniperus Mexicana* is permitted to grow for a period of between three months and over twelve months at the end of which point in time the *Juniperus Mexicana* is either cut down or parts are cut away and utilized either as green wood or in the dried stage for purposes of extraction.

The extraction of the high thujopsene-containing cedarwood oil is carried out by means of:

(a) first steam distilling the resultant green or aged cedarwood chips and condensing the overhead distillate thereby forming two liquid phases; an aqueous phase and an organic phase;

(b) separating the aqueous phase from the organic phase;

(c) optionally extracting the aqueous phase with an organic solvent such as diethylether to form a solvent extract;

(d) optionally evaporating the solvent extract and recycling the solvent;

(e) optionally combining the resulting residue with the steam distilled organic oil phase;

(f) optionally fractionally distilling the resultant combined organic phase or separated organic phase (if no extraction takes place) to yield a rectified cedarwood oil in high yield.

The organic phase resulting from the steam distillation may be re-steam distilled one or more times if desired to give rise to a more highly rectified material.

The bipyridylium salts are applied at concentrations of from about 0.15% up to about 40% in aqueous, alcoholic or aqueous/alcoholic solutions. The growing tree to which the solution may be applied may be from about 20 years up to about 80 years old. The harvesting of the trees may take place from about 2 months up to about 2 years after said solutions are applied.

BRIEF DESCRIPTION OF THE DRAWINGS

FIG. 1 is the GLC profile of a composite cedarwood oil sample extracted from cedarwood chips using the apparatus of FIGS. 55 or 56, described infra.

FIG. 2A being a schematic diagram of a cedarwood tree showing percentages of cedarwood oil in various parts of the tree untreated and FIG. 2B a schematic diagram of a cedarwood tree treated with 1% "PARAQUAT®" having the structure:

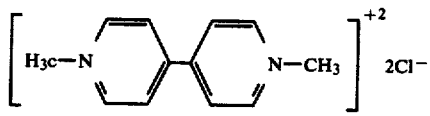

indicating the various percentages of high thujopsene-containing cedarwood oil in various parts of the tree after 12 months treatment.

Figure 3:
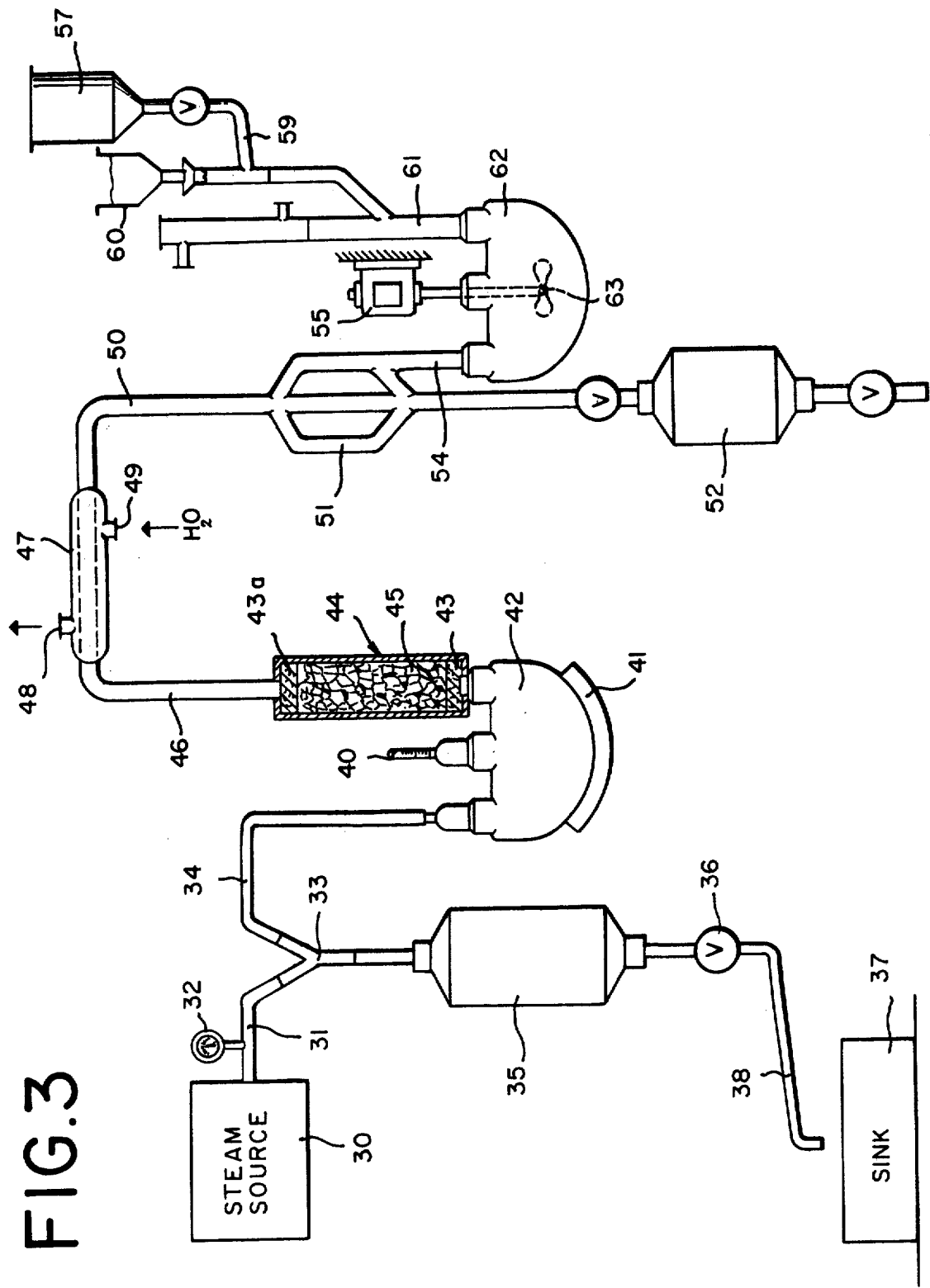

FIG. 3 illustrates laboratory apparatus for testing quantities of high thujopsene-containing cedarwood oil by steam distilling the cedarwood oil from *Juniperus Mexicana* chips and appropriately treating the resulting two phases of the steam distillate.

Figure 4:
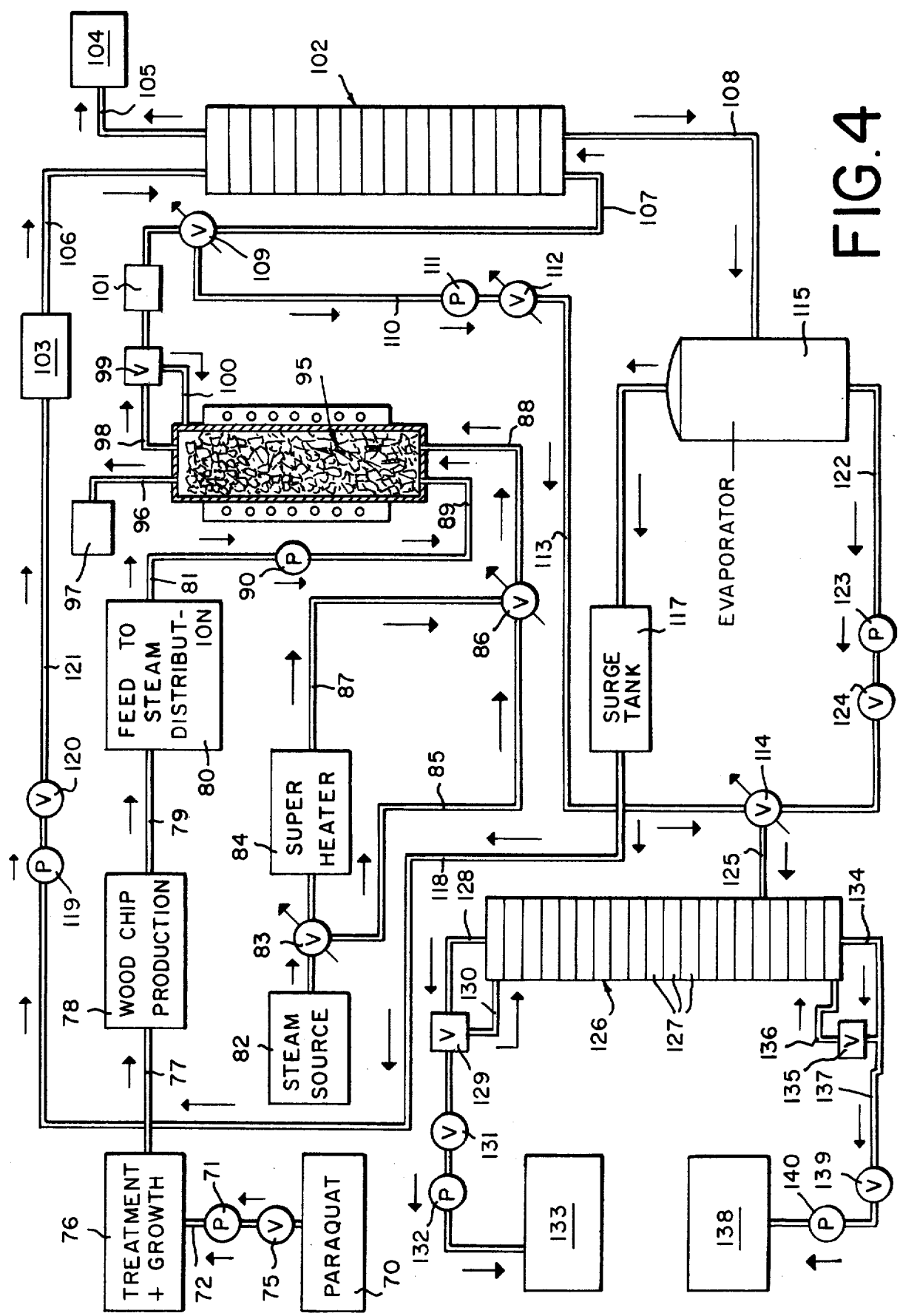

FIG. 4 is a diagram of commercial apparatus useful for carrying out the process of our invention commencing with the treatment of growing *Juniperus Mexicana* using bipyridylium salts followed by harvesting of the *Juniperus Mexicana* after a fixed amount of time followed by steam distillation and appropriate treatment of the steam distillate to yield high thujopsene-containing cedarwood oil.

Figure 5:
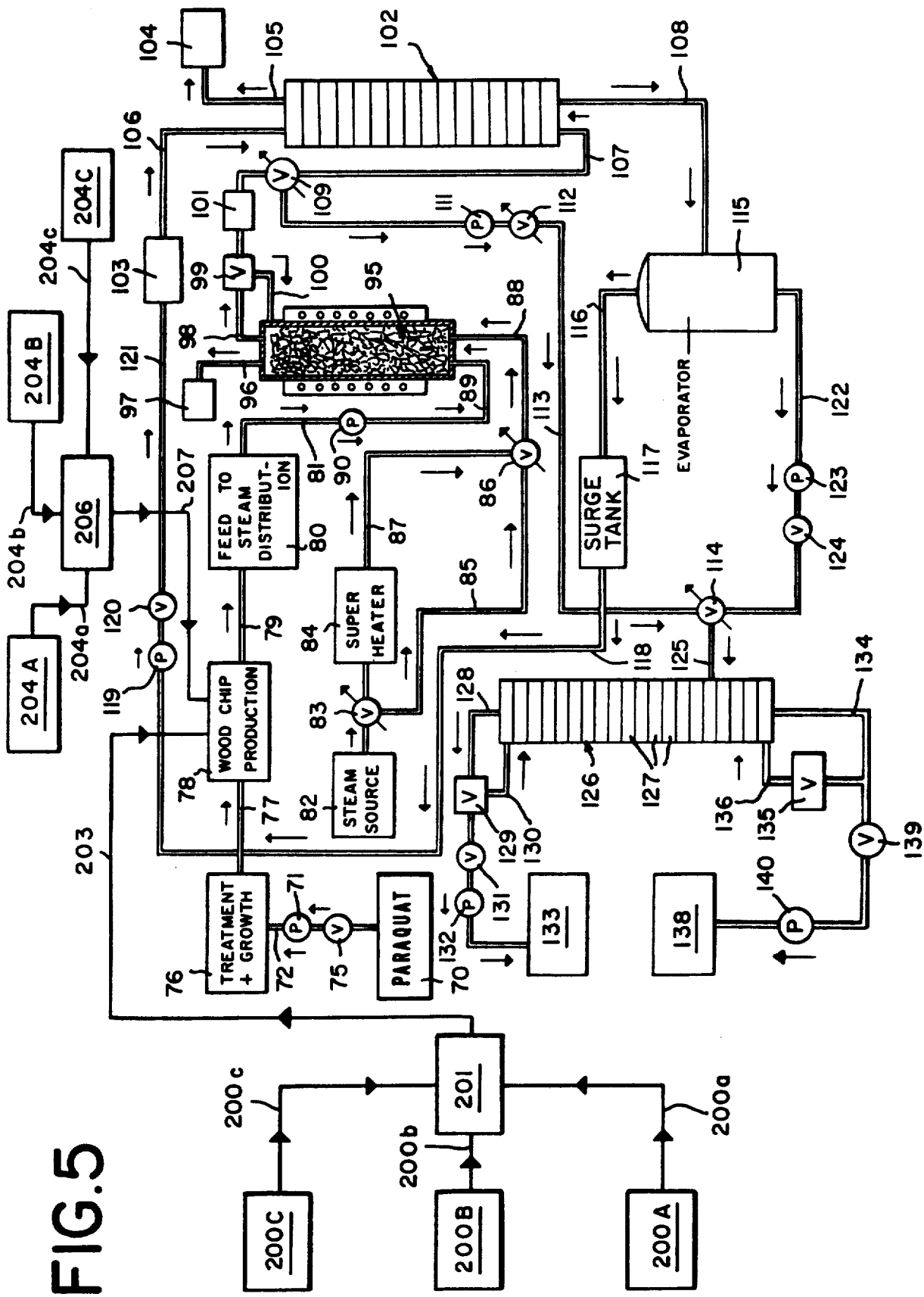

FIG. 5 is another schematic flow diagram showing apparatus useful in practicing the process of our invention whereby in addition to bipyridylium salts being used to treat *Juniperus Mexicana* other materials may also be used to treat the *Juniperus Mexicana* and, simultaneously, other oils are extracted from other botanical species after treatment thereof with bipyridylium salts, the various harvested wood chips being combined for subsequent steam distillation and additional unit operations to produce a combined essential oil.

Figure 6:
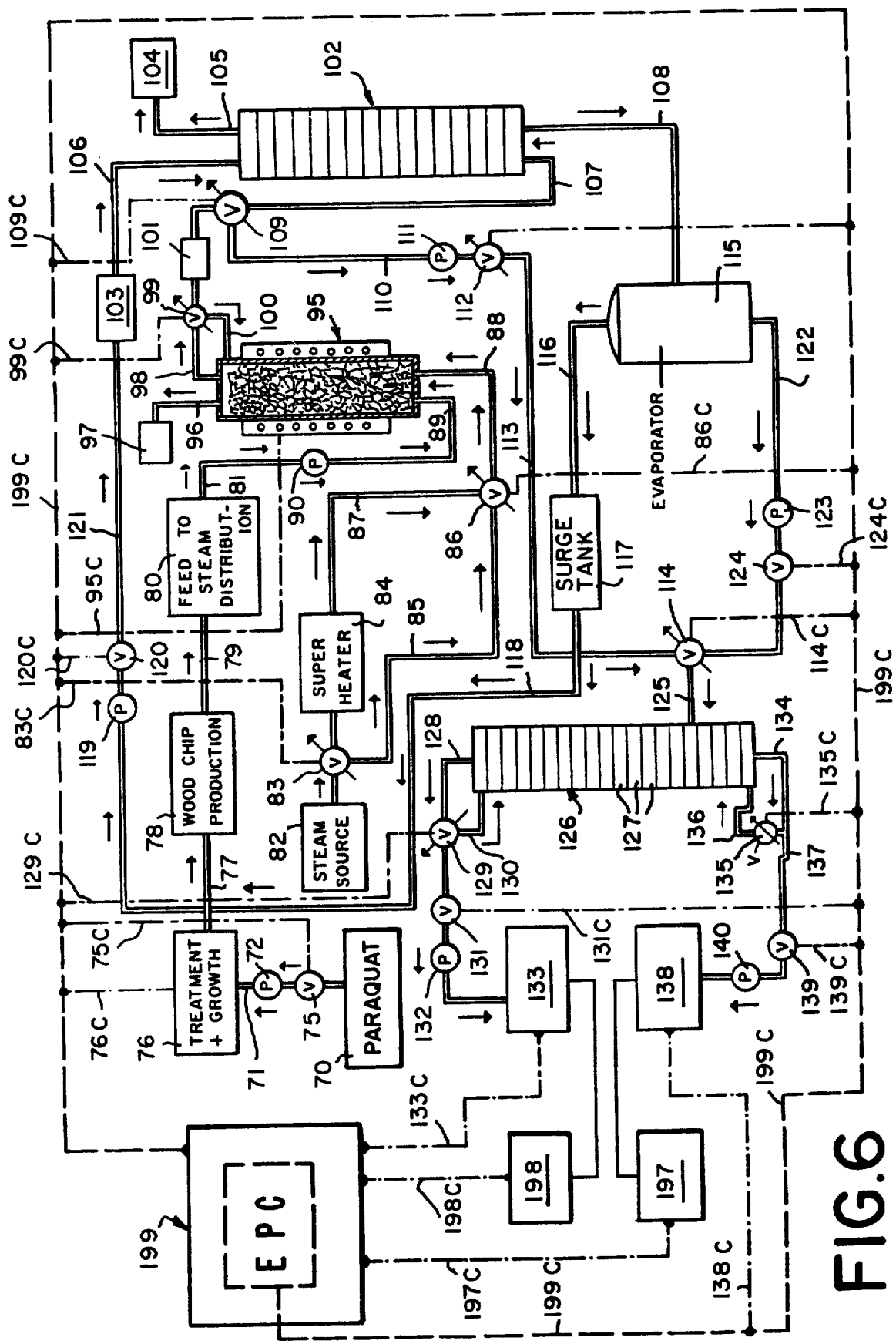

FIG. 6 shows the schematic diagram of FIG. 4 showing the apparatus used to carry out the process of our invention wherein the flow rates of feeds and extraction agents are controlled in order to optimize the yield of high thujopsene-containing cedarwood oil using an electronic programming system.

Figure 7:
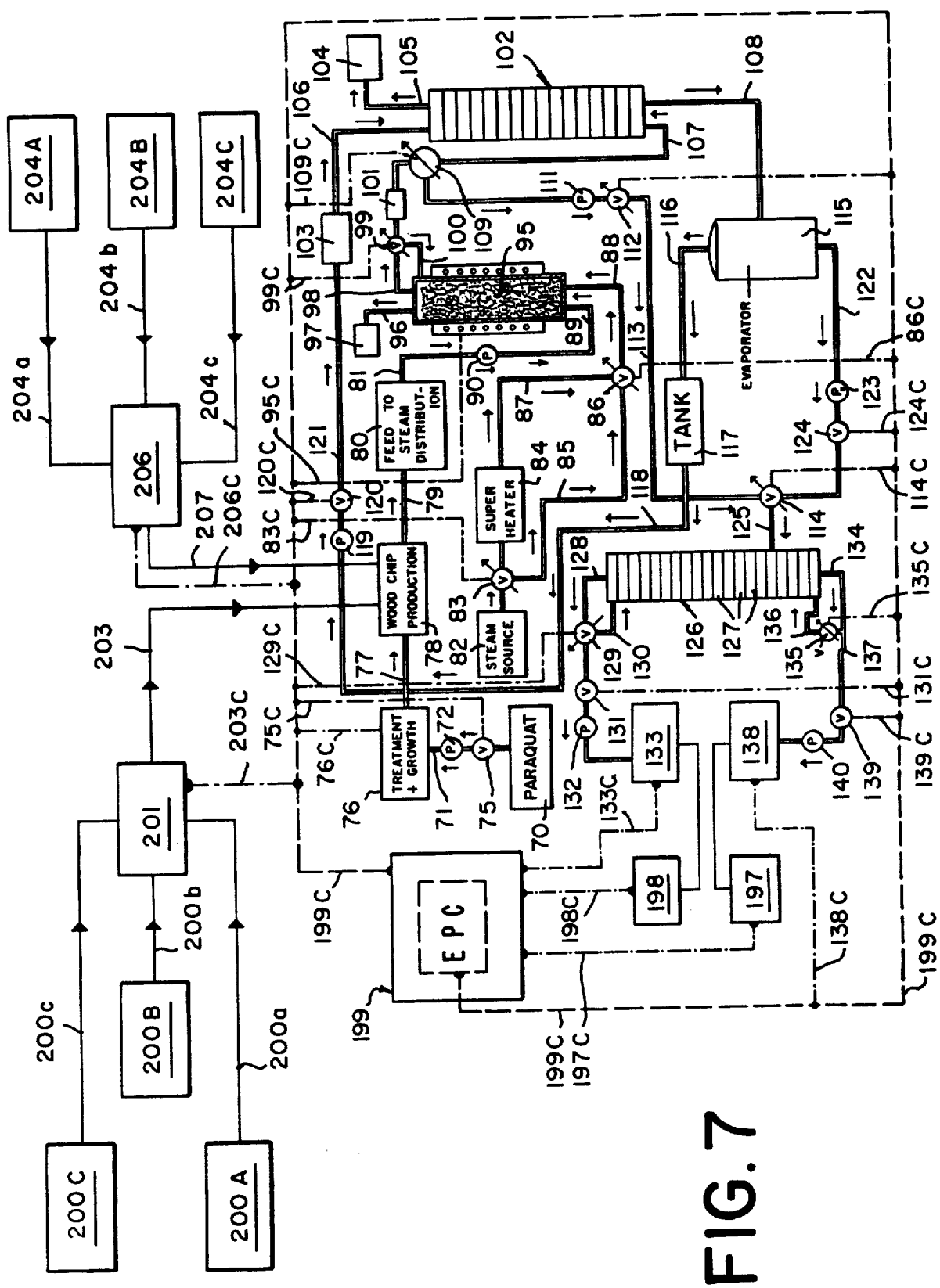

FIG. 7 is the process flow diagram of FIG. 5 showing the apparatus of FIG. 5 with various feed rates and solvent flow rates controlled for purposes of optimization of the production of the high thujopsene-containing cedarwood oil using an electronic programming control system.

Figure 8:
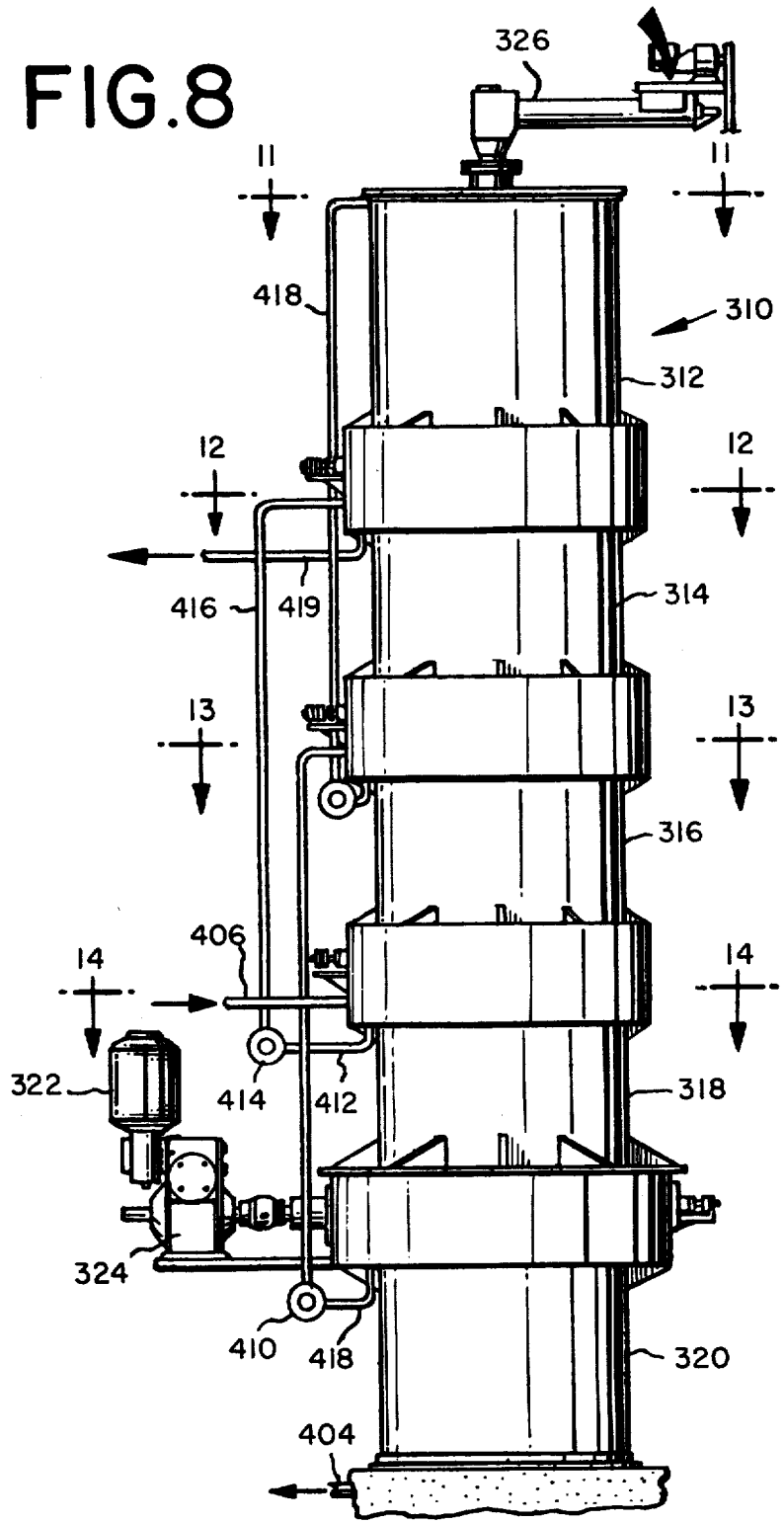

FIG. 8 is an elevational view of a preferred embodiment of apparatus useful for the steam distillation of high thujopsene-containing cedarwood oil from green or aged cedarwood chips from cut Juniperus Mexicana.

Figure 9:
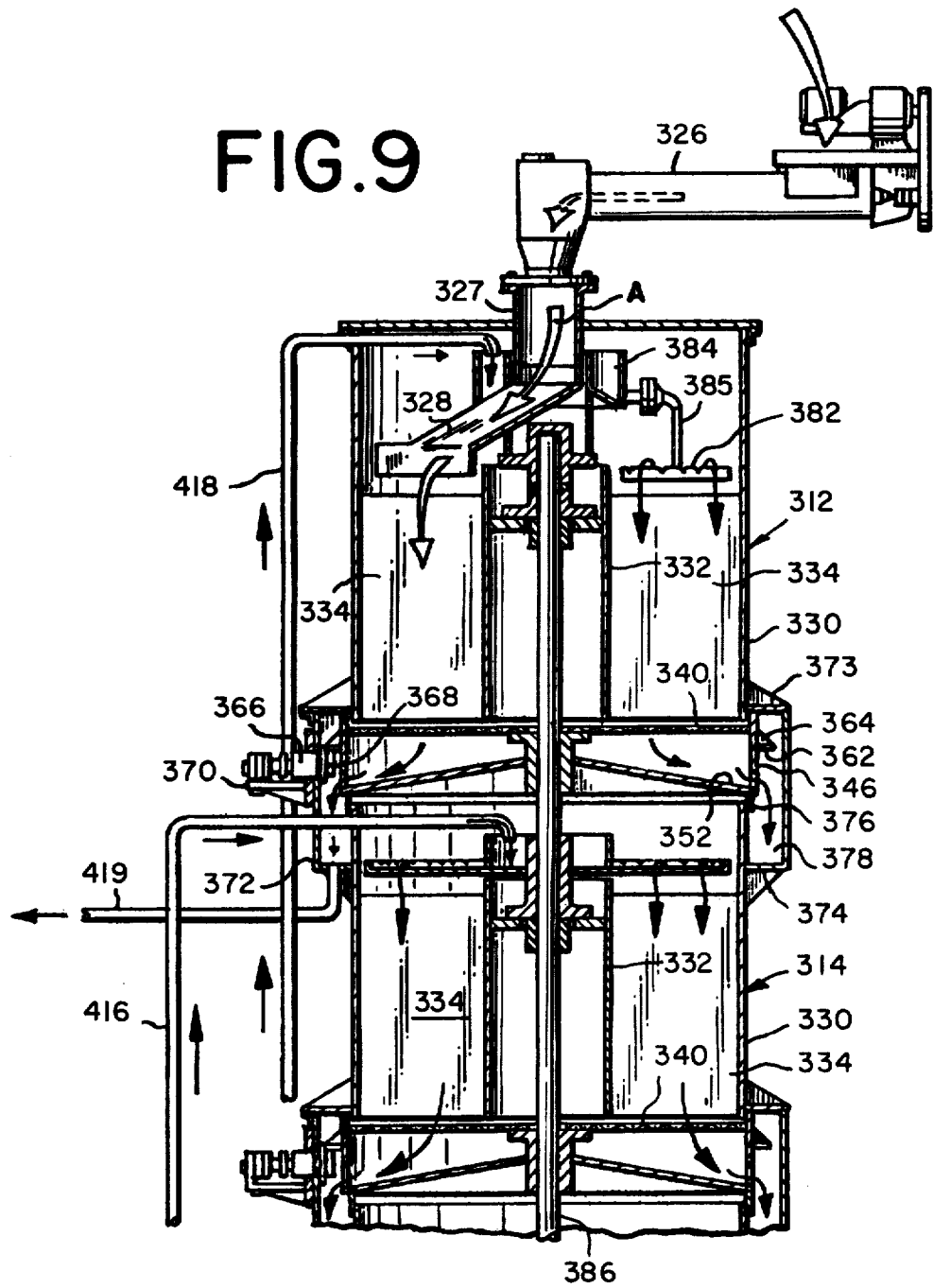

FIG. 9 is a vertical cross-sectional view of the upper two stages of the embodiment of FIG. 8.

Figure 10:
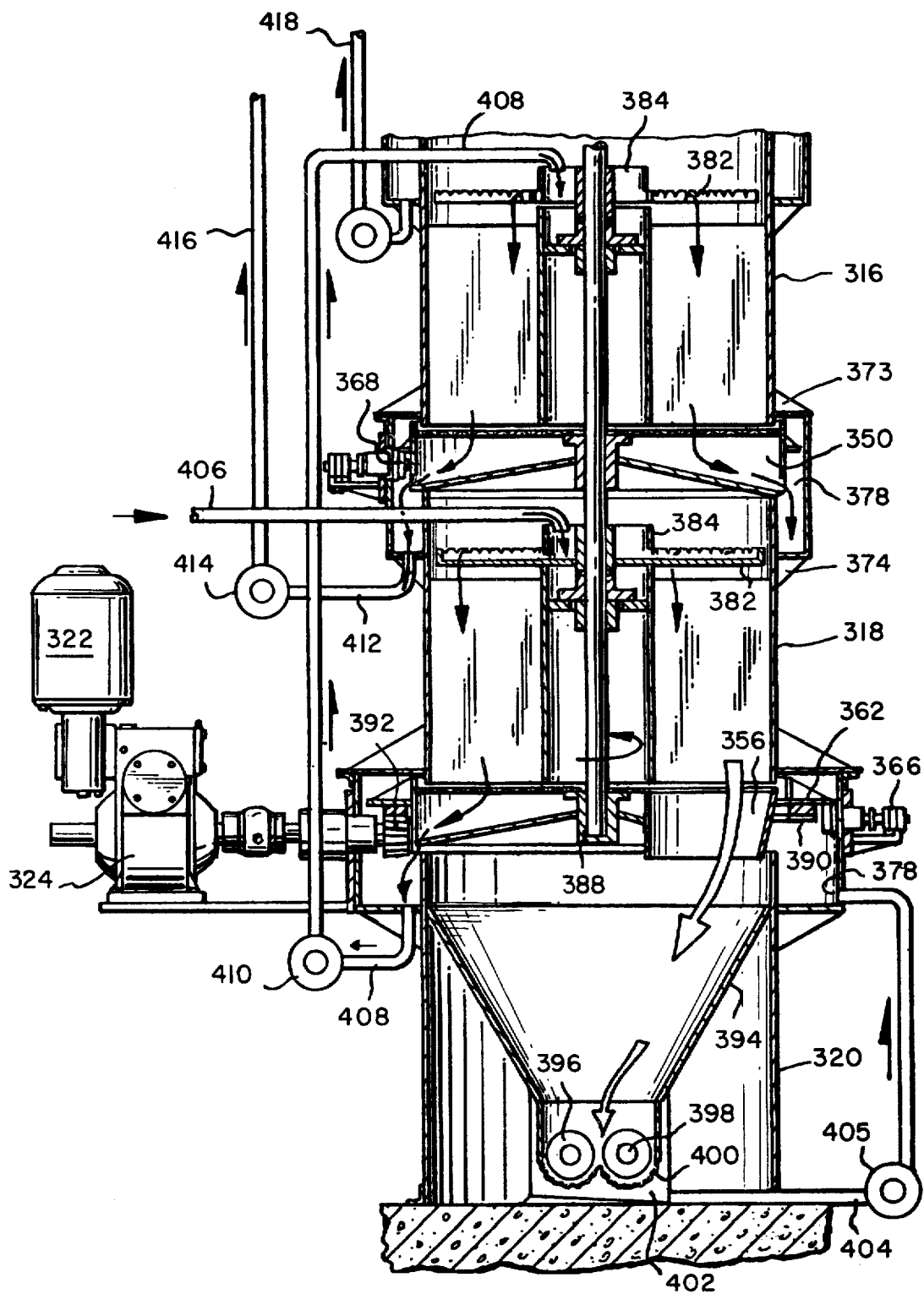

FIG. 10 is a vertical cross-sectional view of the lower two stages and material removal system of the embodiment of FIG. 8.

Figure 11:
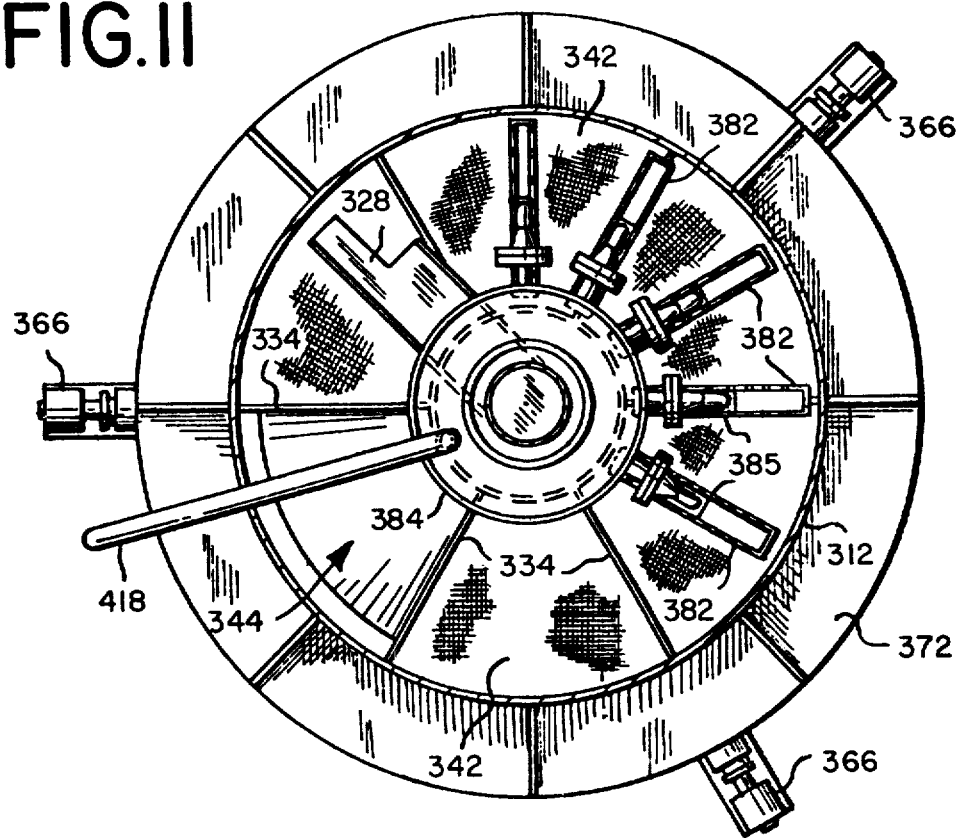

FIG. 11 is a cross-sectional view along the line 11—11 of FIG. 8 showing the miscella distribution system and material distribution troth in the first stage.

Figure 12:
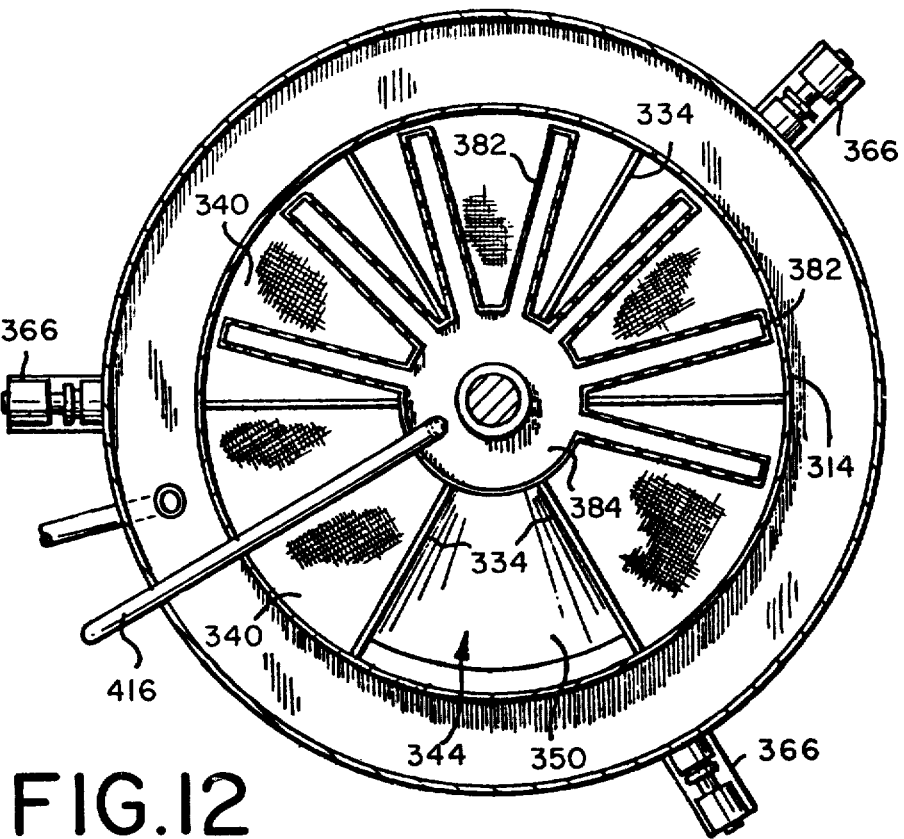

FIG. 12 is a horizontal cross-sectional view along the line 12—12 of FIG. 8 illustrating the miscella distribution system for the second stage.

FIG. 13 is a horizontal cross-sectional view along the line 13—13 of FIG. 8 showing the miscella distribution system for the third stage.

FIG. 14 is a horizontal cross-sectional view along the line 14—14 of FIG. 8 illustrating the miscella distribution system of the fourth stage.

Figure 15:
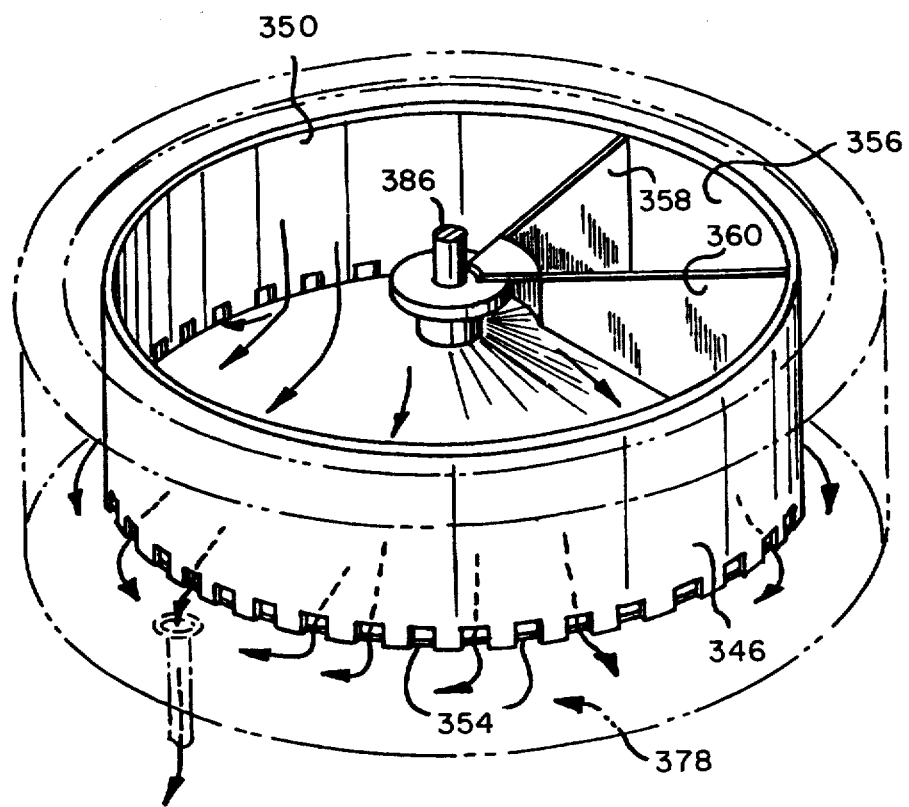

FIG. 15 is a pictorial illustration of a collection pan exemplary of the collection pan in each of the stages of the embodiment of FIG. 8.

Figure 16:
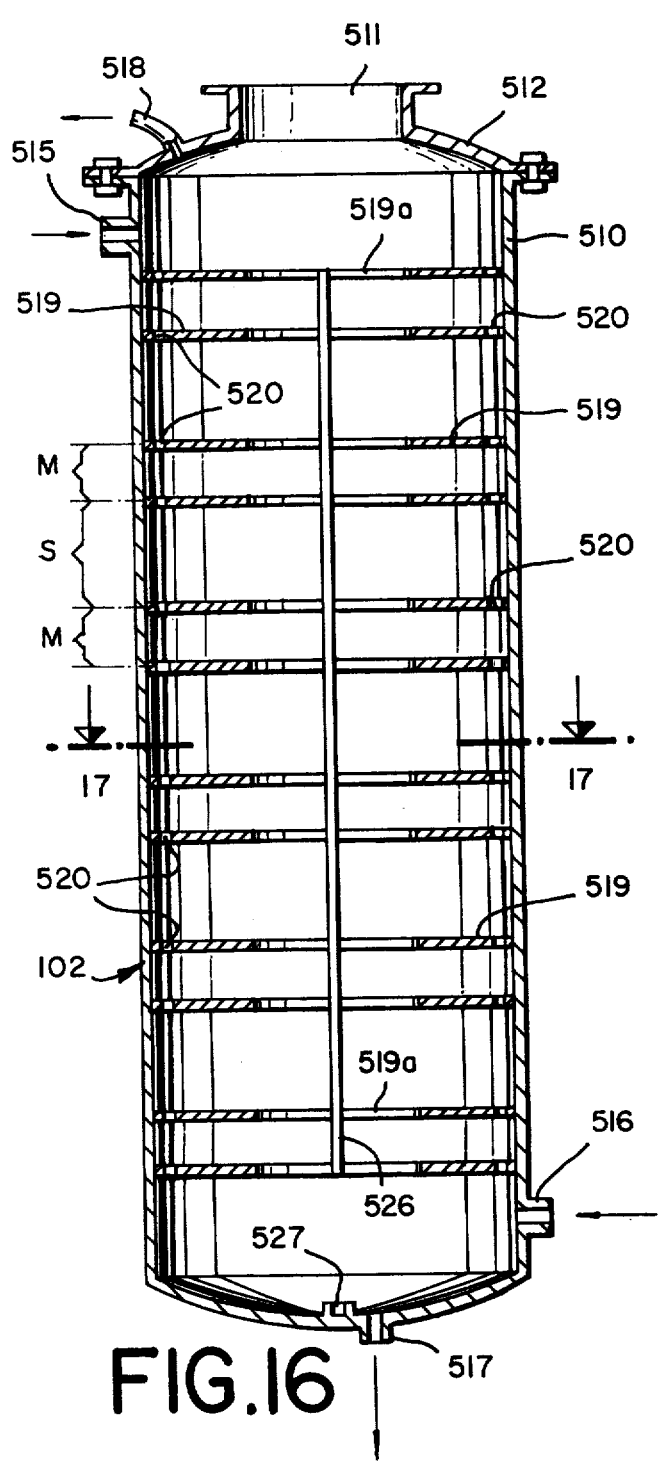

FIG. 16 is an elevation longitudinal cross-sectional view through the cylindrical shell of multi-stage internal mixer-settler extraction apparatus useful in carrying out the process of our invention as illustrated in FIGS. 4, 5, 6 and 7, the extractor being apparatus indicated by reference numeral "102" in FIGS. 4, 5, 6 and 7.

Figure 17:
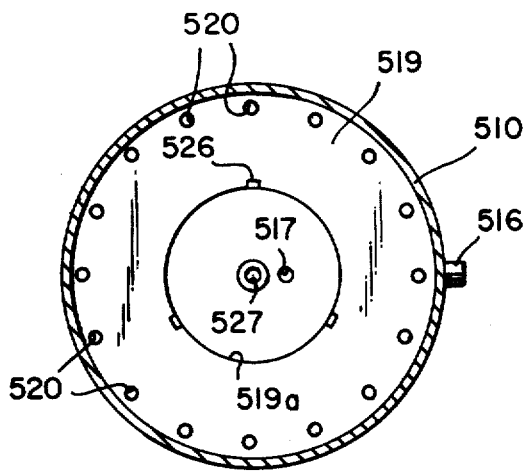

FIG. 17 is a transverse section taken along line 17—17 of FIG. 16.

Figure 18:
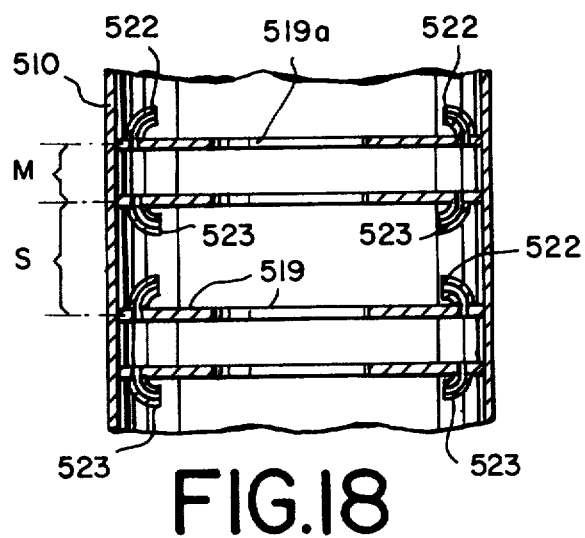
Figure 19:
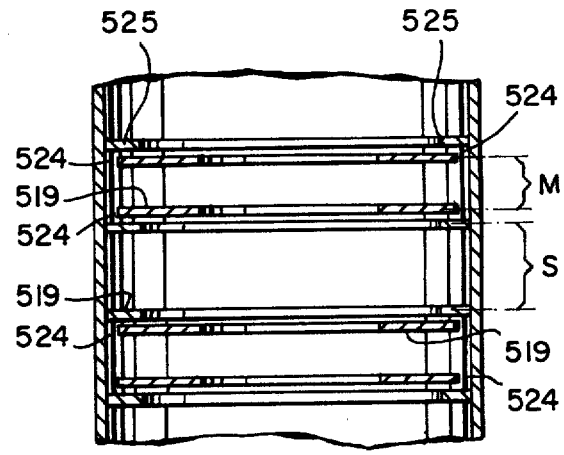

FIGS. 18 and 19 are fragmentary views similar to FIG. 16 of the extraction apparatus but showing alternative forms of passages through the transverse plates of said extraction apparatus.

Figure 20:
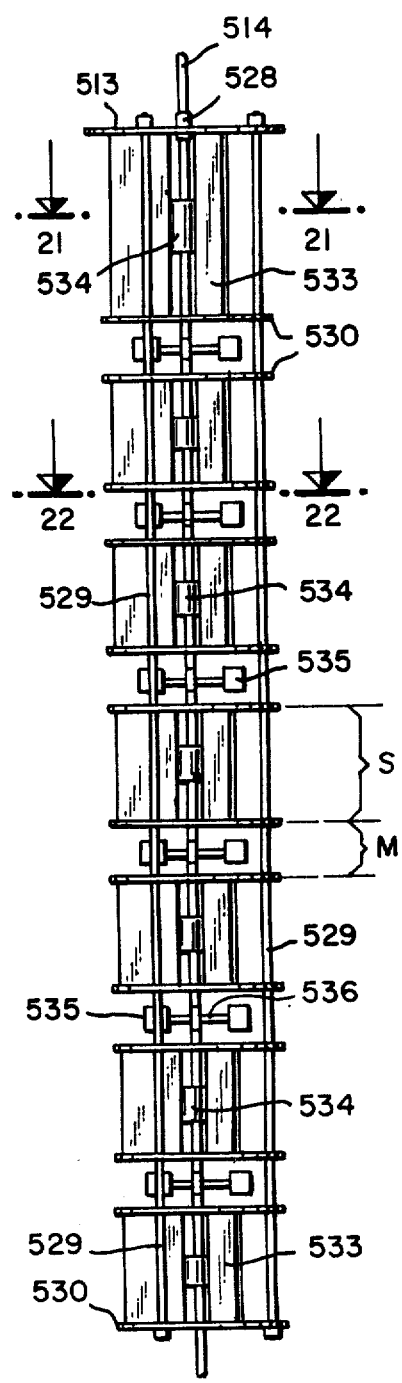

FIG. 20 is an elevation view of the core assembly or the extraction apparatus of FIG. 16 with certain elements shown in vertical section.

Figure 21:
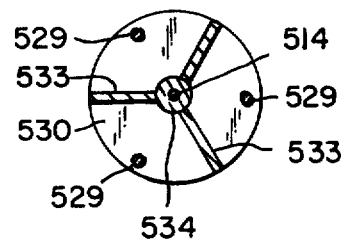

FIG. 21 is a horizontal section through that part of the core assembly in a settling zone taken along line 21—21 of FIG. 20.

Figure 22:
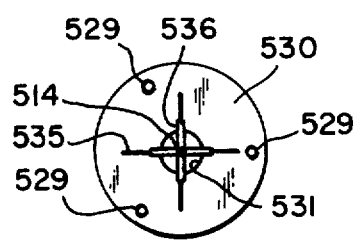

FIG. 22 is a section similar to that section of FIG. 21 through that part of the core assembly of the extraction apparatus of FIG. 16 in a mixing zone taken along line 22—22 of FIG. 20.

Figure 23:
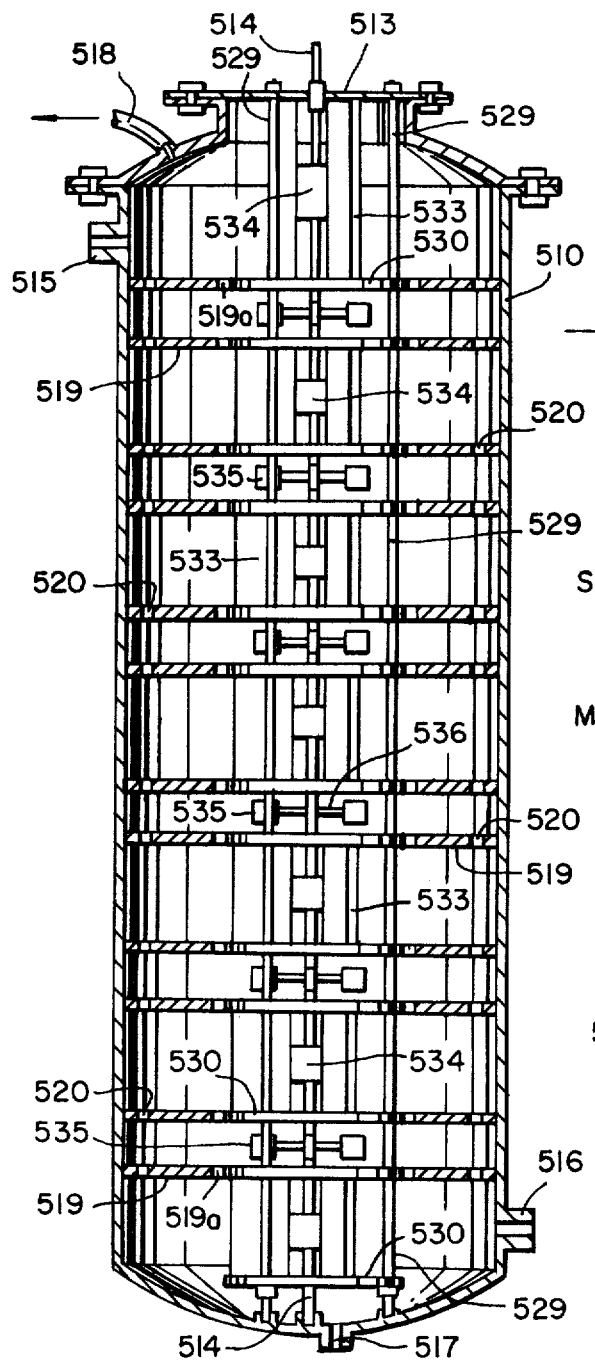

FIG. 23 shows the assembled multi-stage internal mixer-settler extraction apparatus useful in carrying out the processes as set forth in the diagrams of FIGS. 4, 5, 6 and 7 supra of our invention.

Figure 24:
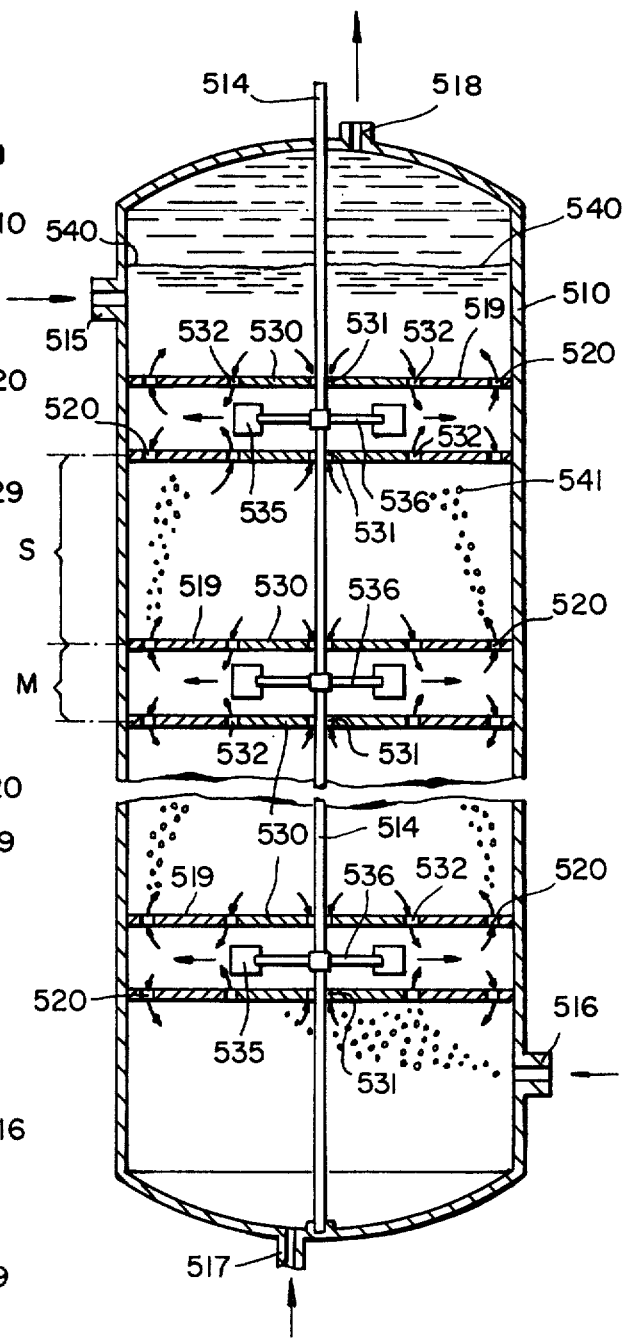

FIG. 24 is a simplified side elevation view of the extraction apparatus useful in carrying out the process of our invention showing the flow of two liquid phases therethrough during counter-current extraction (e.g. diethylether extraction of aqueous steam distillate) operations.

Figure 25:
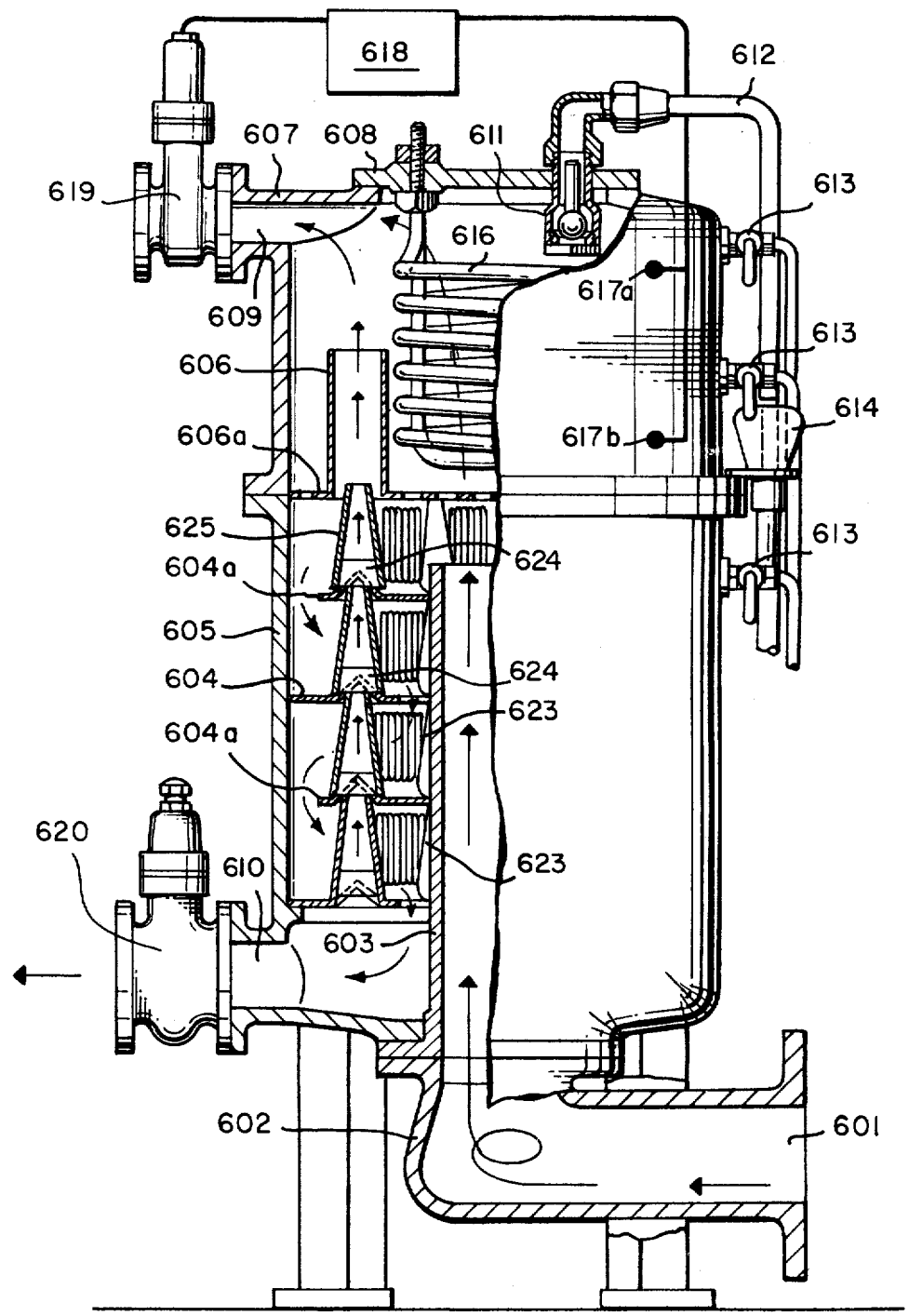

FIG. 25 is a partly sectional side view of a separator embodying extraction apparatus useful in carrying out the process of our invention as set forth in the schematic flow diagrams of FIGS. 4, 5, 6 and 7, the extraction apparatus being shown by the reference numeral "102".

FIG. 26 illustrates in cross-section, a partial construction of the plates having frustro-conical members useful in the apparatus as illustrated in FIG. 25.

FIG. 27A is a partial cross-sectional view taken along lines 27A—27A of FIG. 26; of a separator having the plate of FIG. 26.

FIG. 27B is a partial cross-sectional view taken along lines 27B—27B of FIG. 26; of a separator having the plate of FIG. 26.

Figure 55:
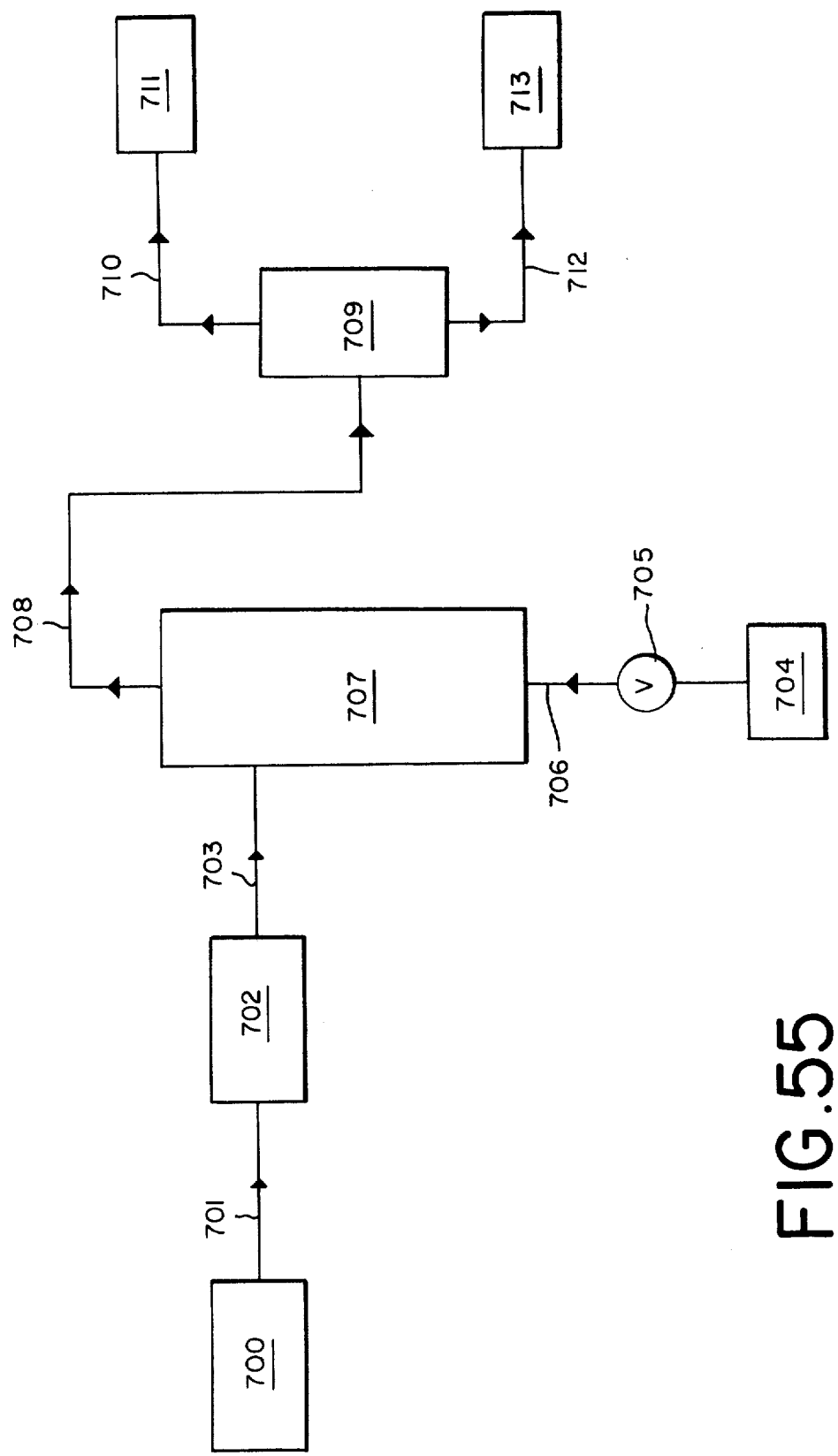
Figure 56:
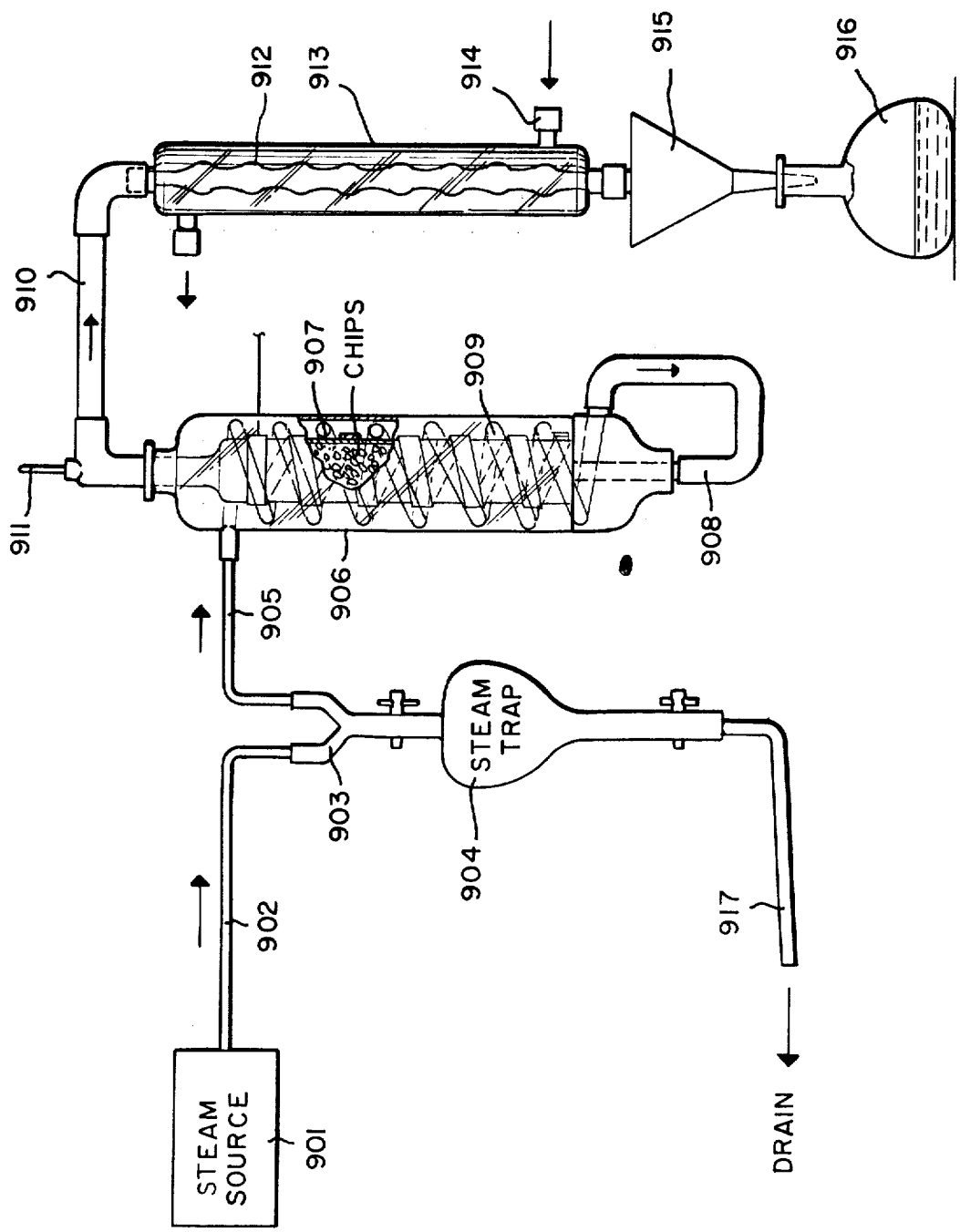

FIG. 28 is the GLC profile for the organic phase of the steam distillation product of steam-distilled cedarwood chips produced according to the process of Example I(A) using apparatus illustrated in FIGS. 55 and 56.

Figure 29:
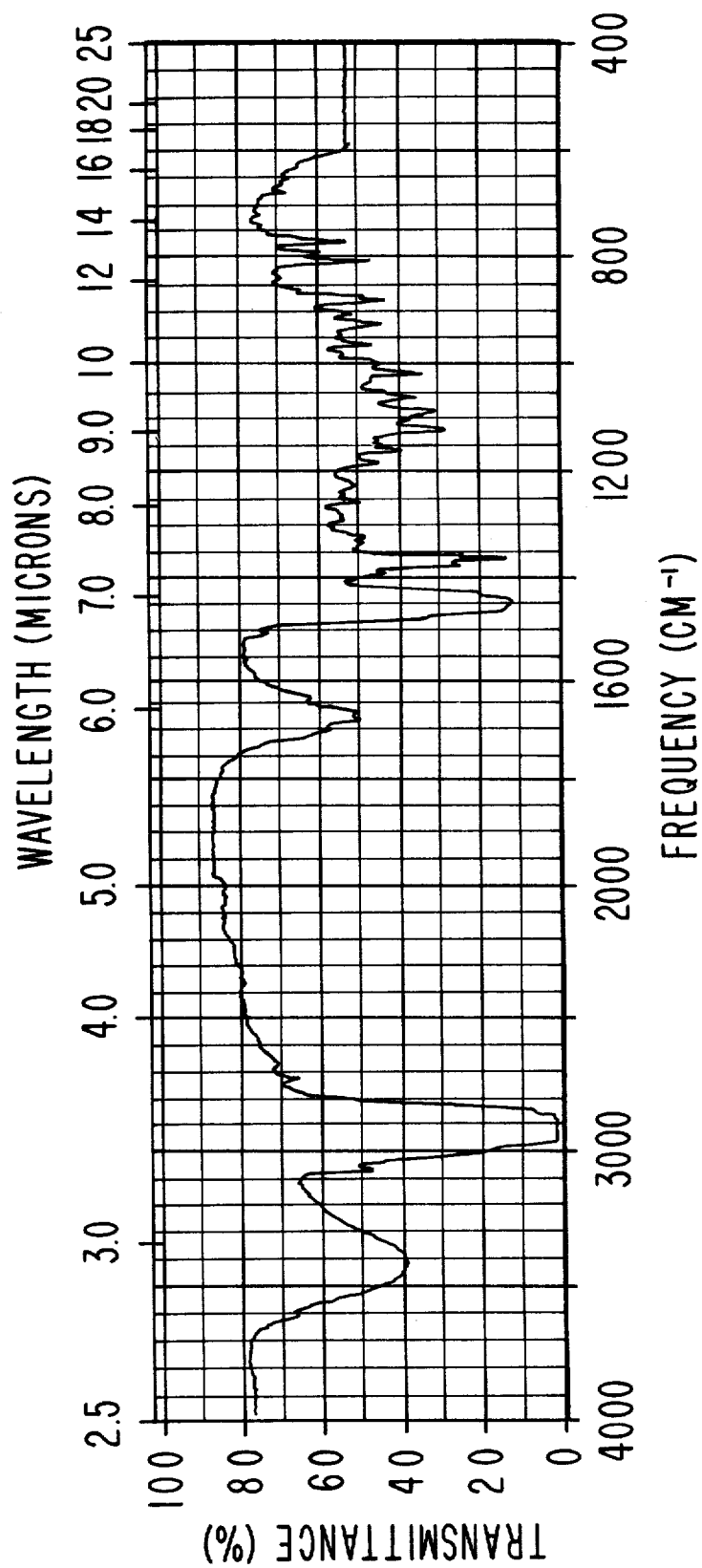

FIG. 29 is the infra-red spectrum for the steam distillate produced according to Example I(A).

Figure 30:
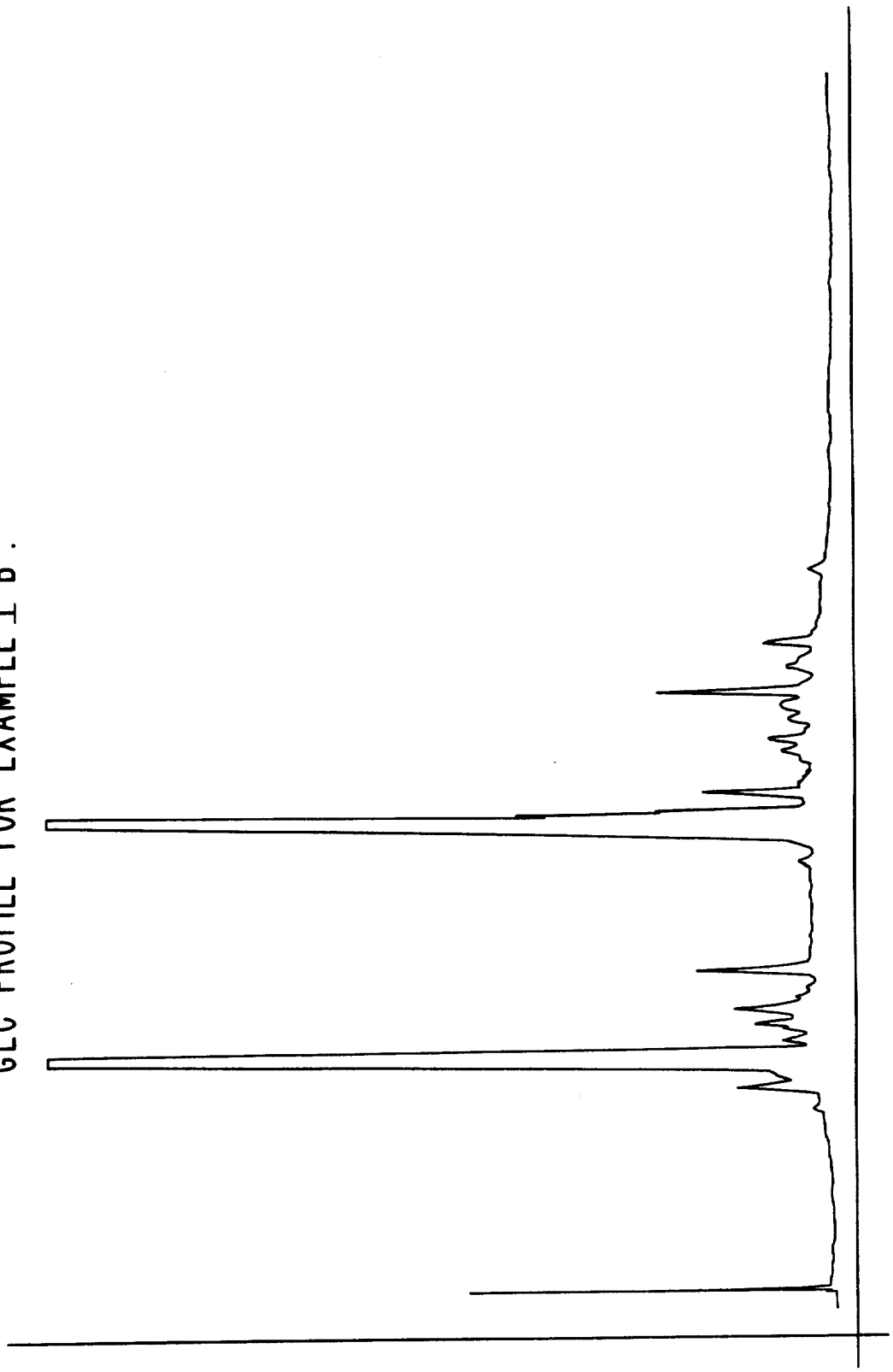

FIG. 30 is the GLC profile for the organic phase of the steam distillate of the cedarwood chips produced according to Example I(B) using the apparatus set forth in FIGS. 55 and 56.

Figure 31:
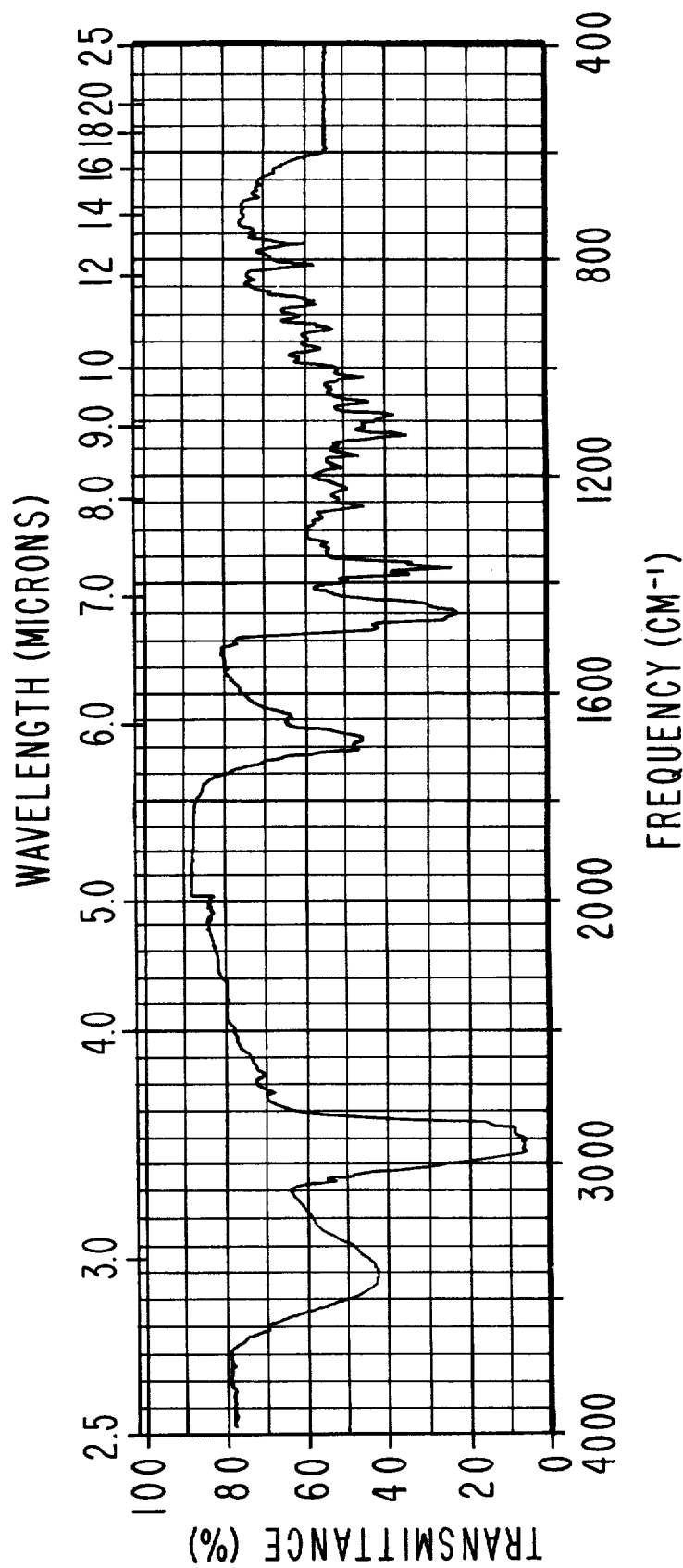
Figure 57:
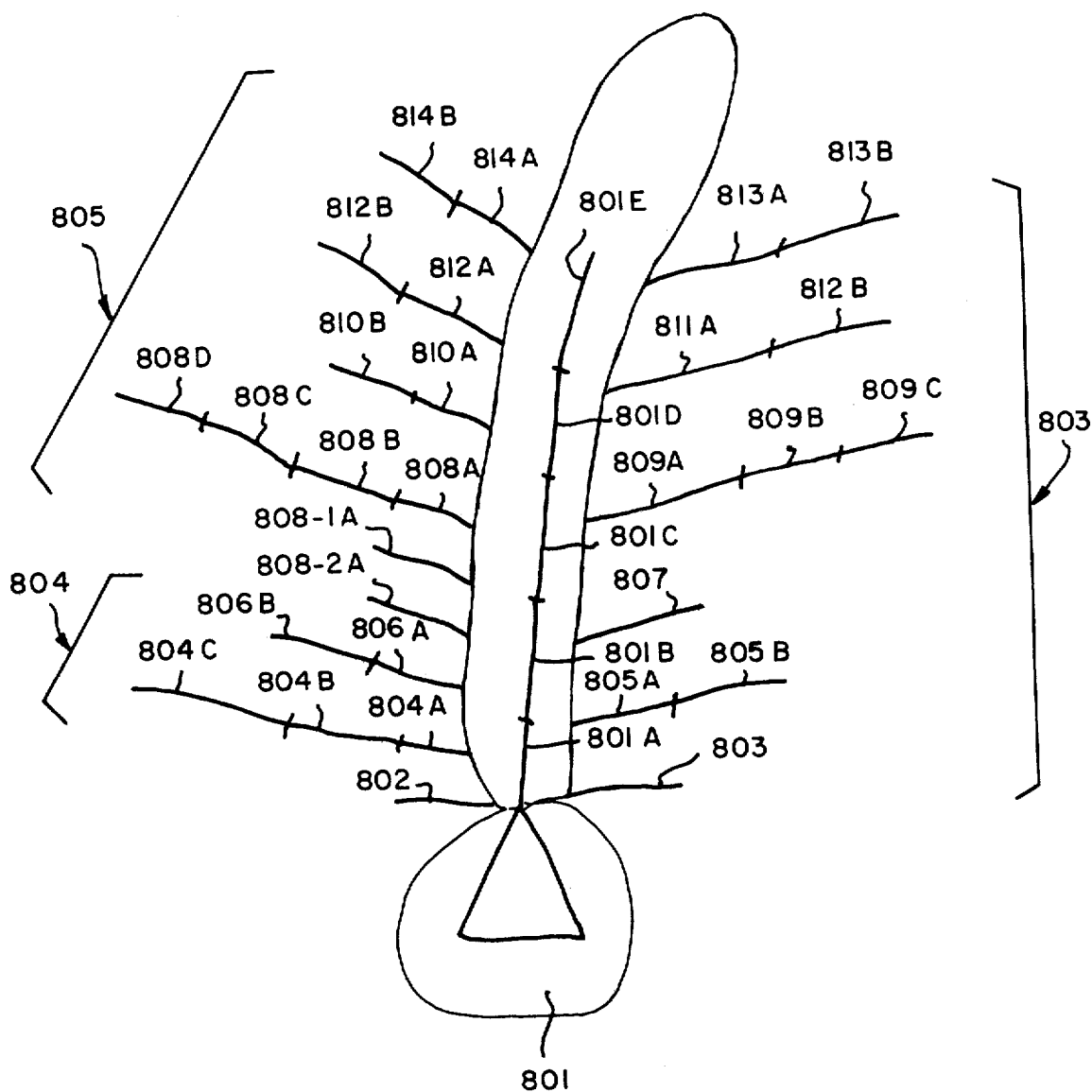

FIG. 31 is the infra-red spectrum of the cedarwood oil steam distillate produced according to Example I(B), the cedarwood chips being taken from section 812-B of the schematic diagram of the *Juniperus Mexicana* tree as set forth in FIG. 57.

Figure 32:
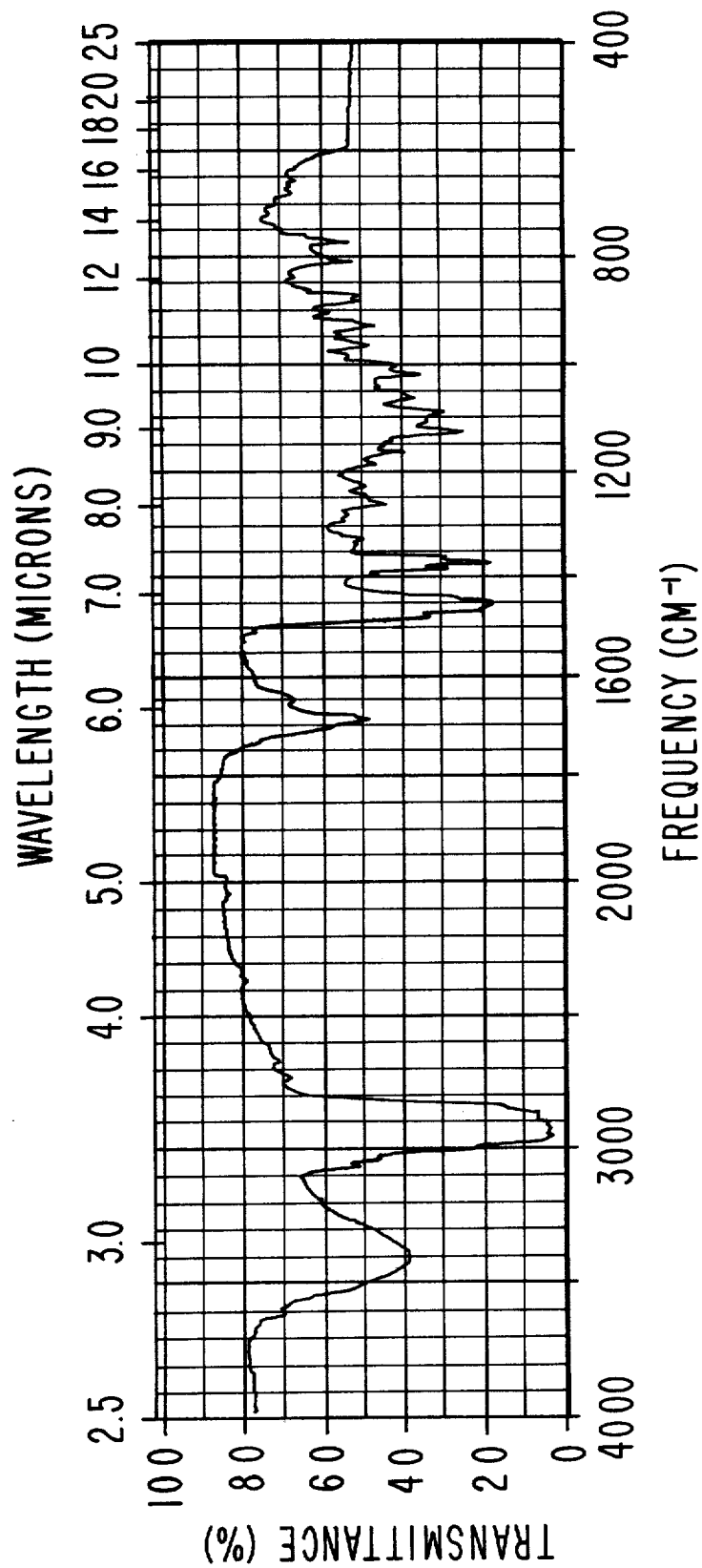

FIG. 32 is the infra-red spectrum of the organic phase of the steam distillate of untreated cedarwood chips taken from section 801-A of the *Juniperus Mexicana* tree as schematically set forth in the diagram of FIG. 57 and as produced according to Example I(B).

Figure 33:
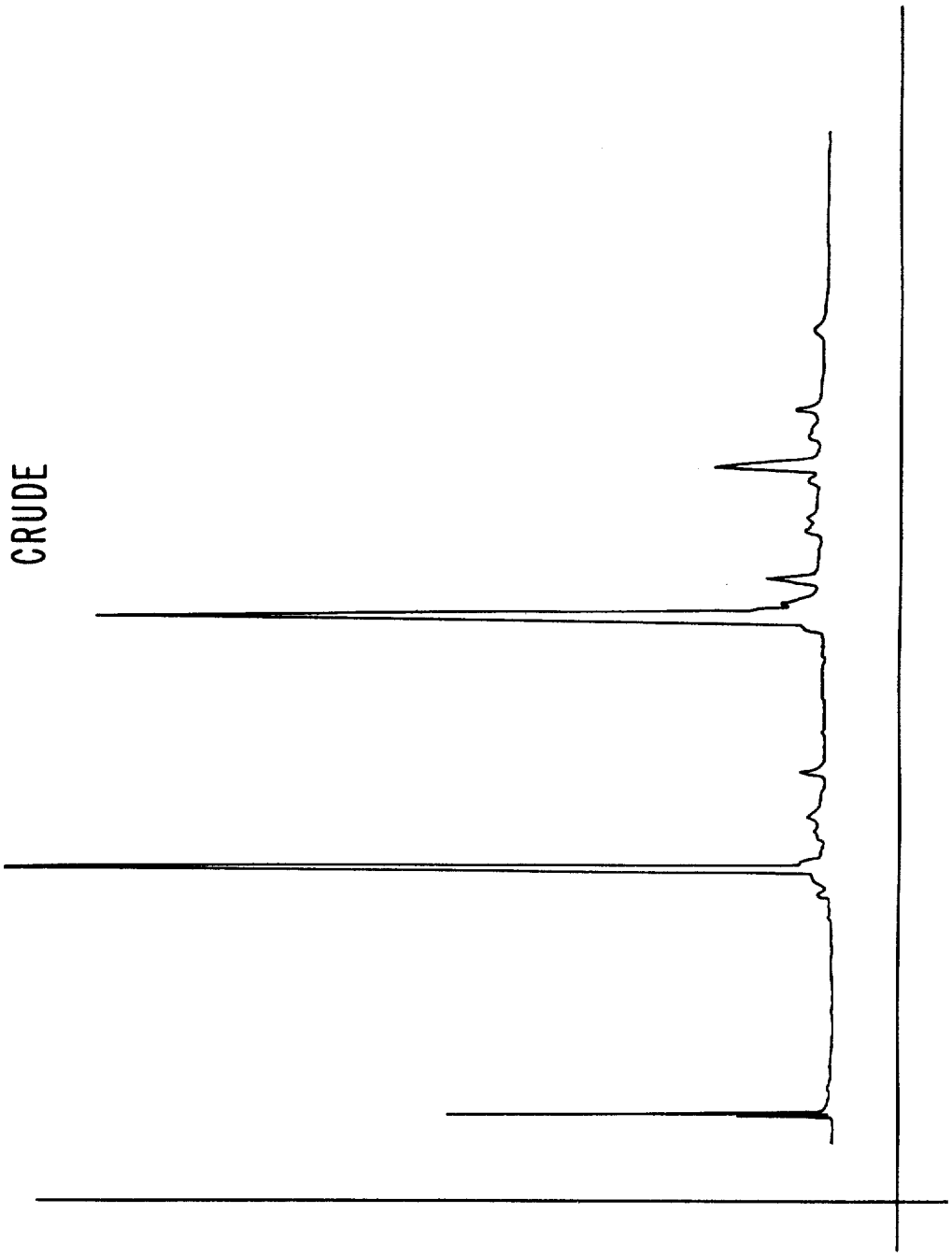

FIG. 33 is the GLC profile for the crude organic phase of the steam distillate prior to distillation of treated *Juniperus Mexicana* chips produced according to Example I(C) using the apparatus of FIG. 3.

Figure 34:
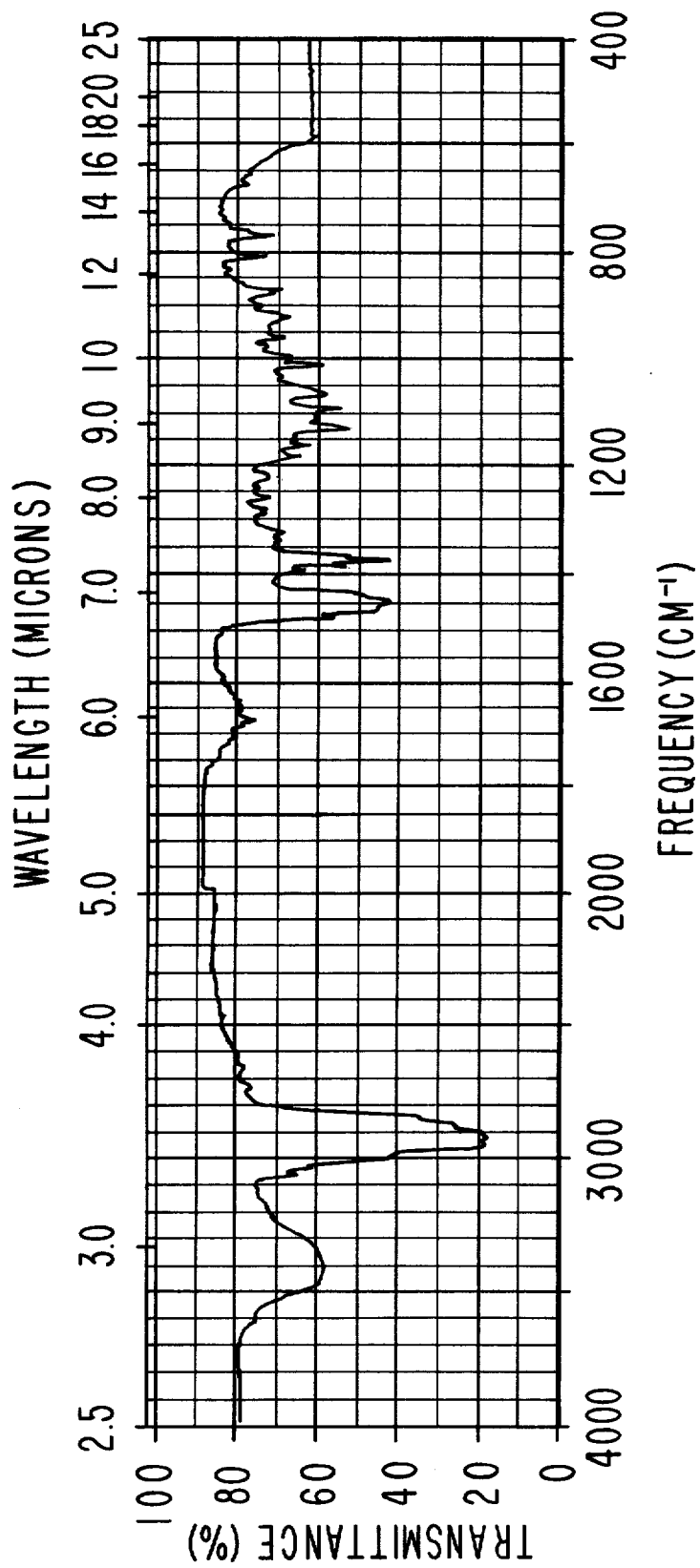
Figure 35:
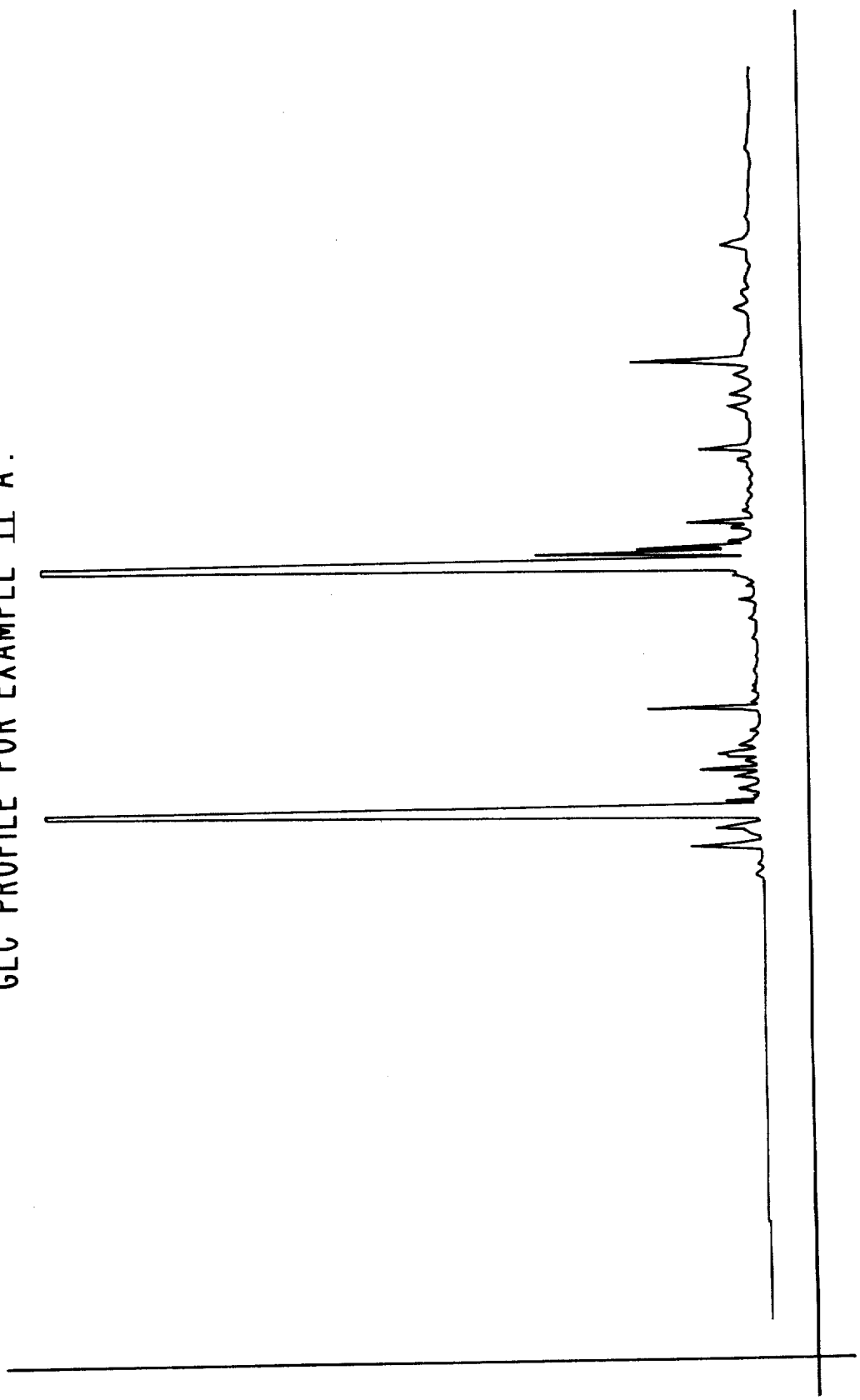
Figure 36:
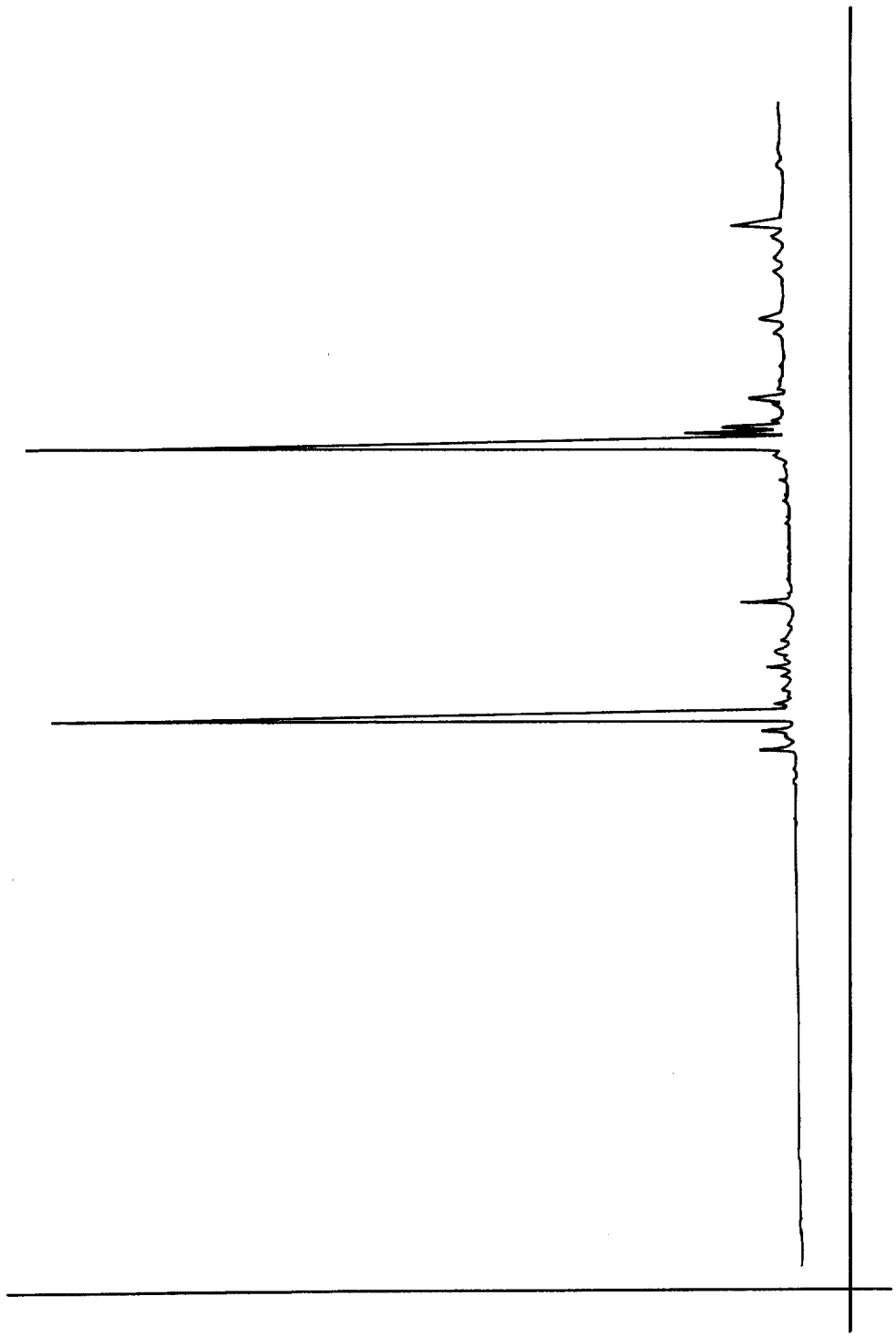
Figure 37:
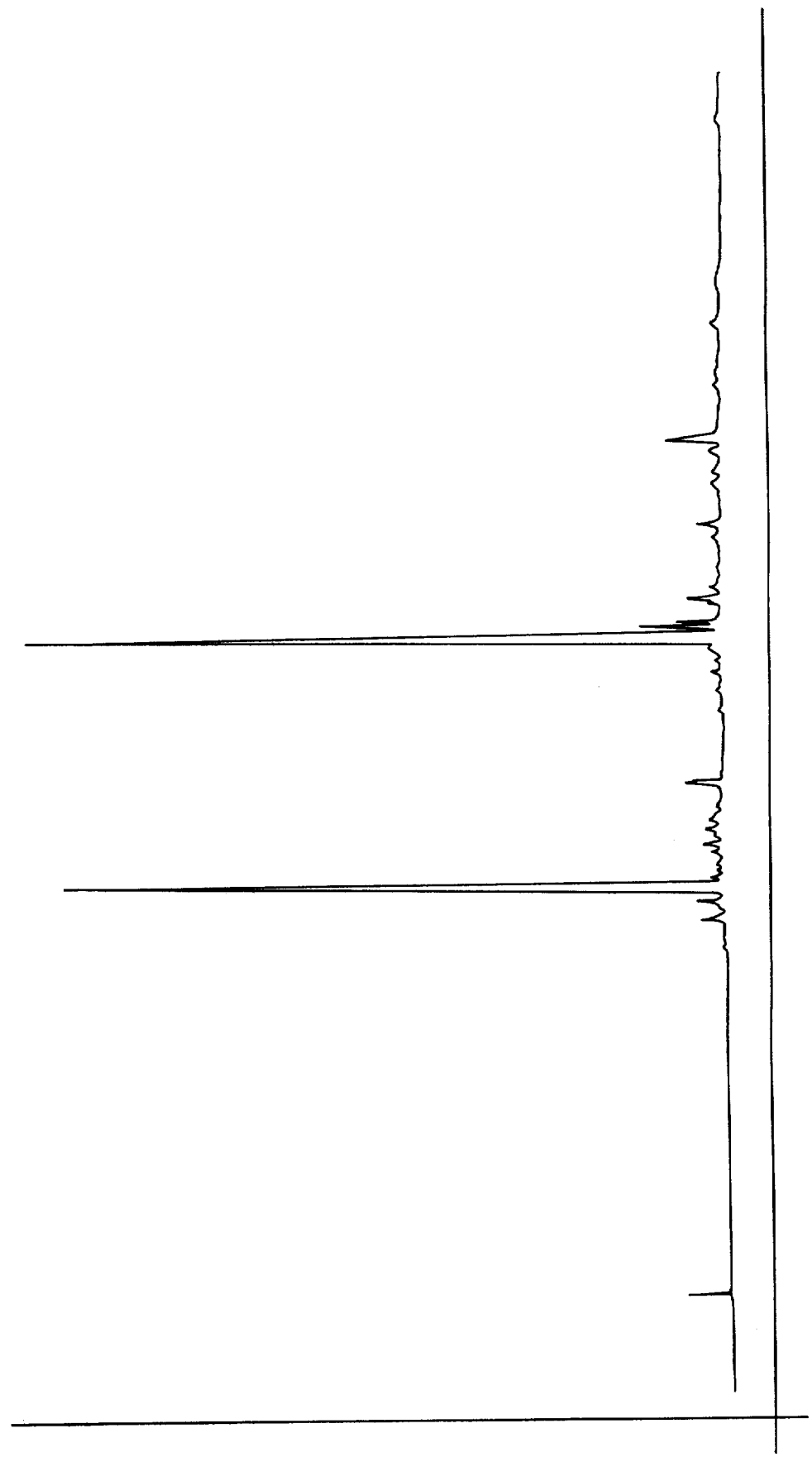
Figure 38:
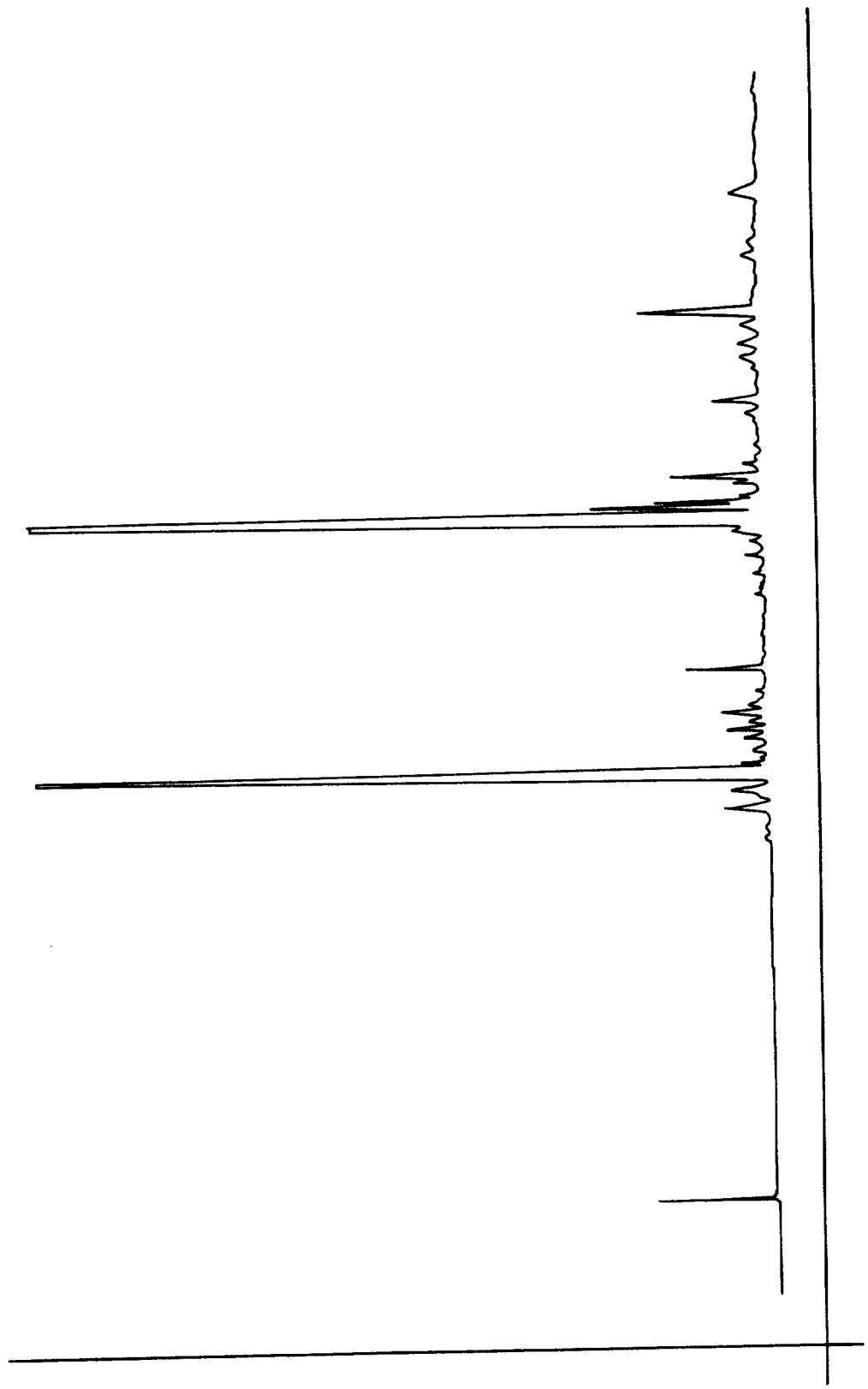
Figure 39:
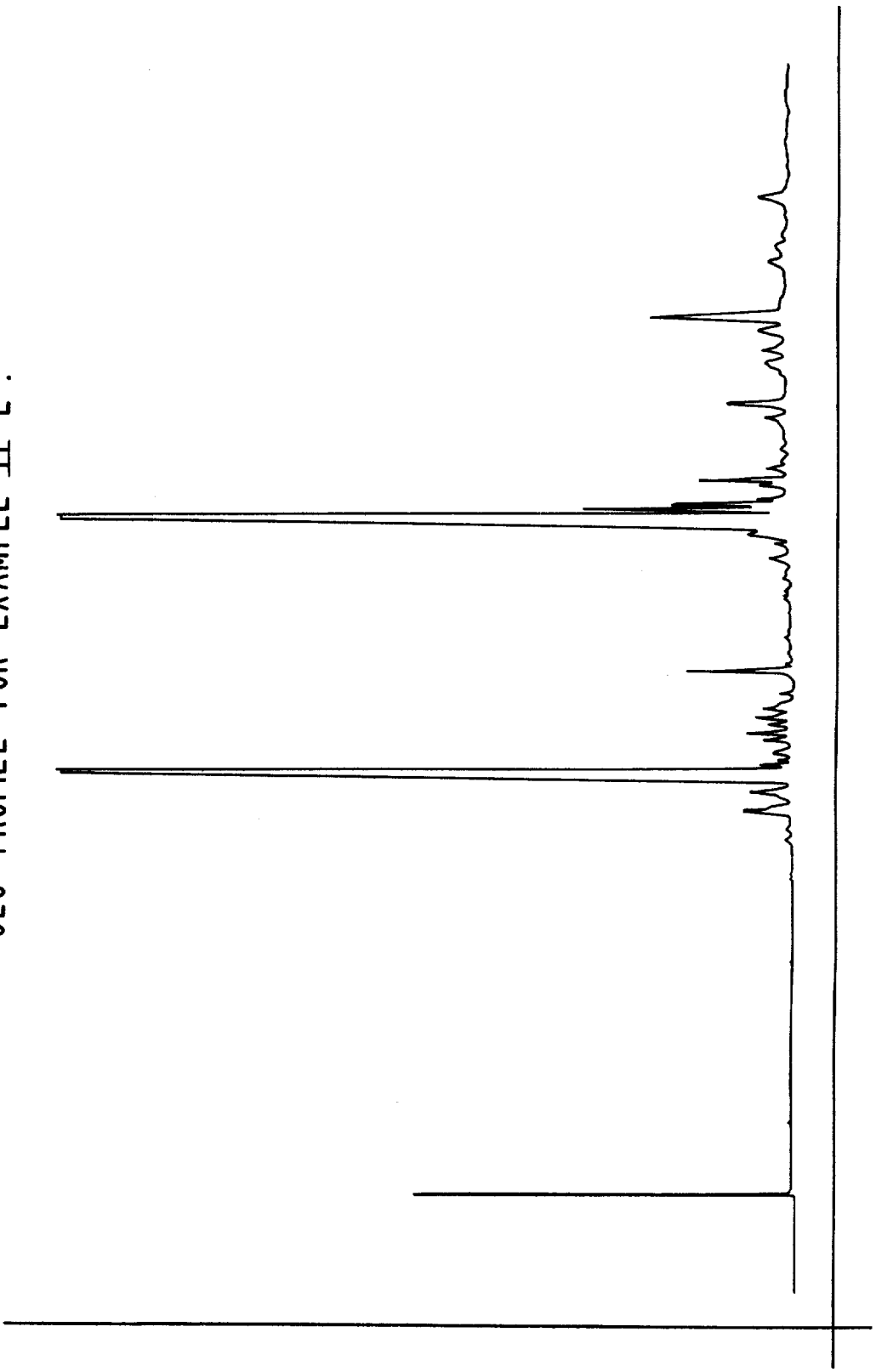
Figure 40:
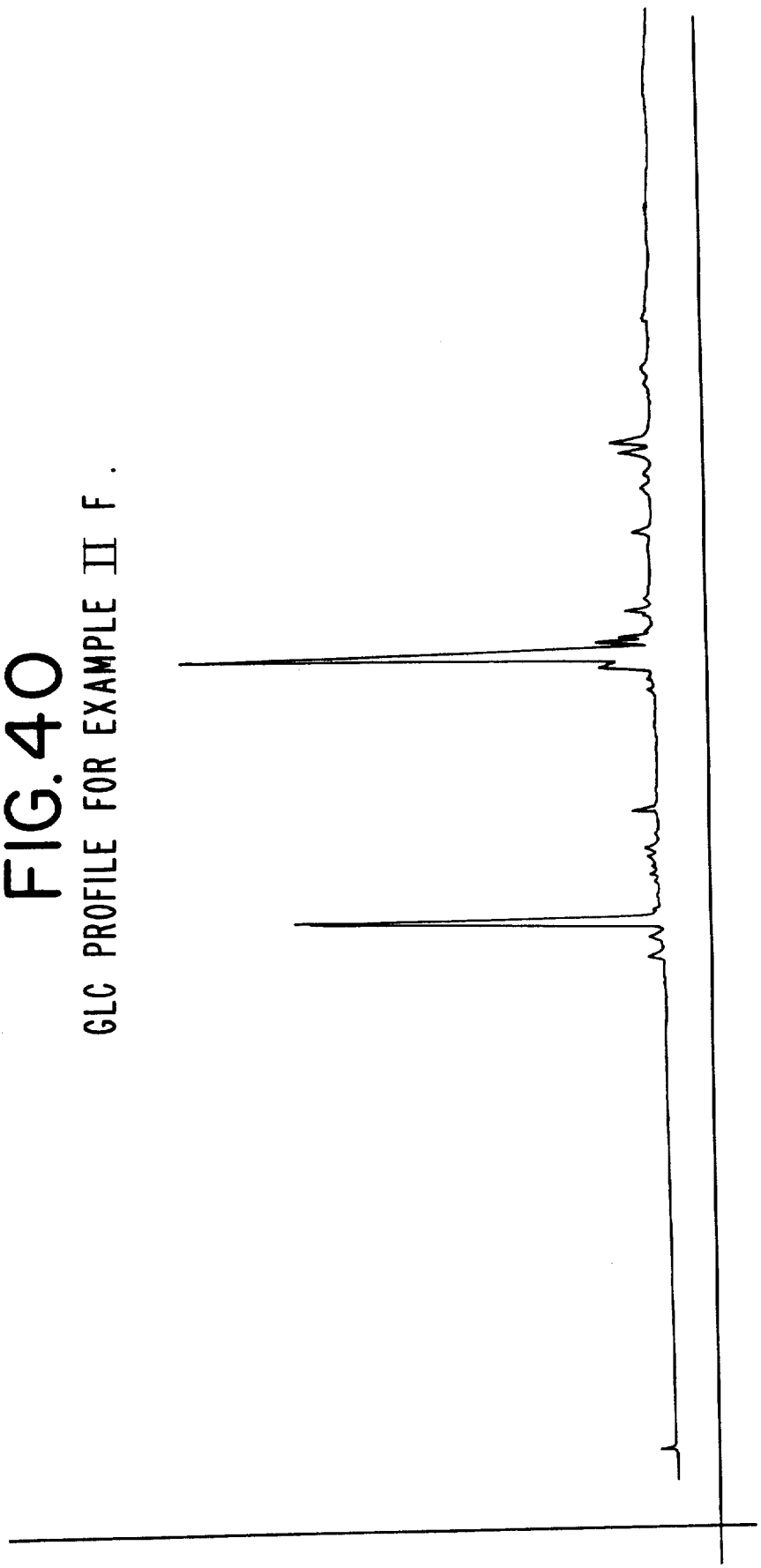
Figure 41:
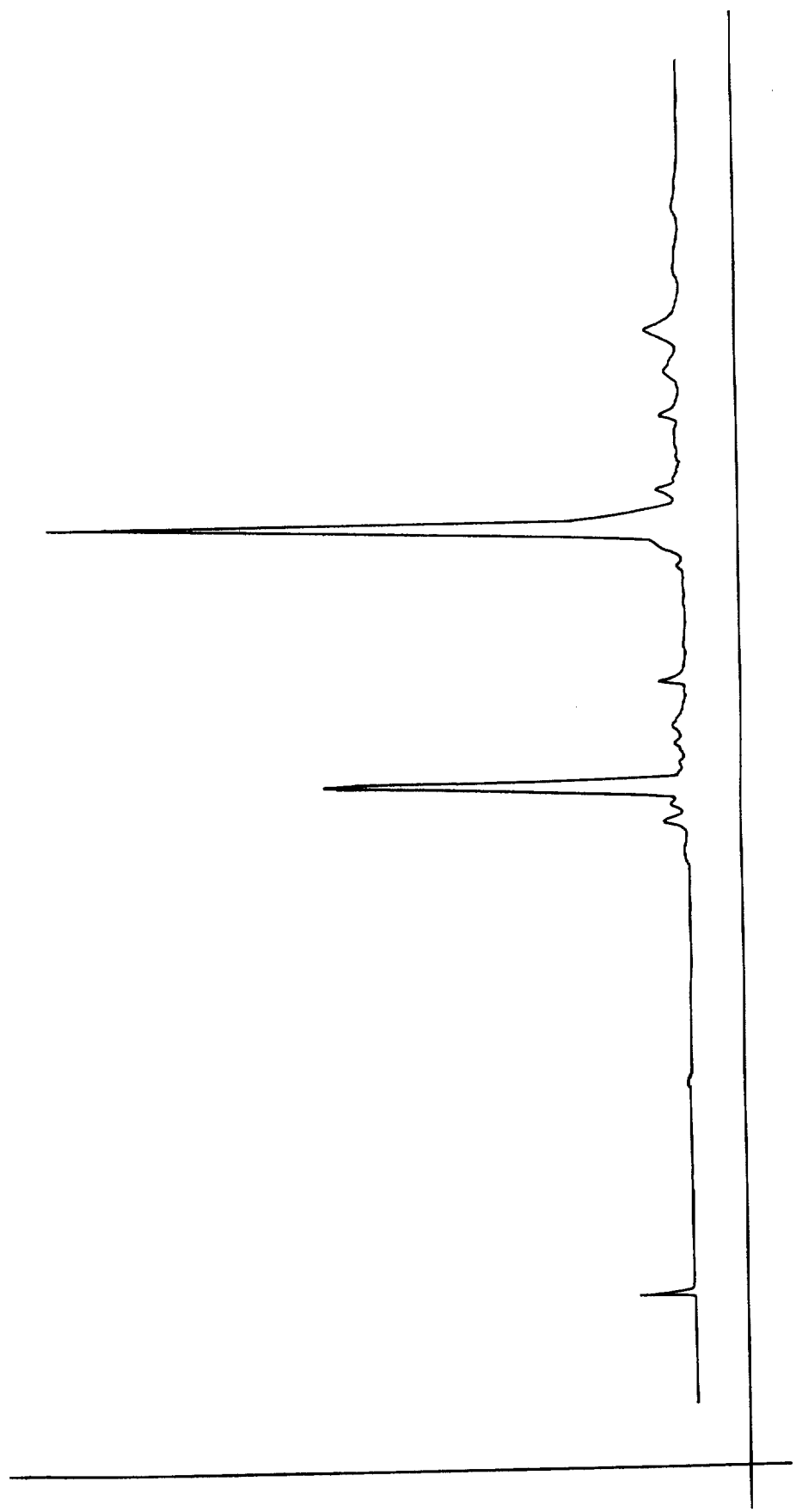
Figure 42:
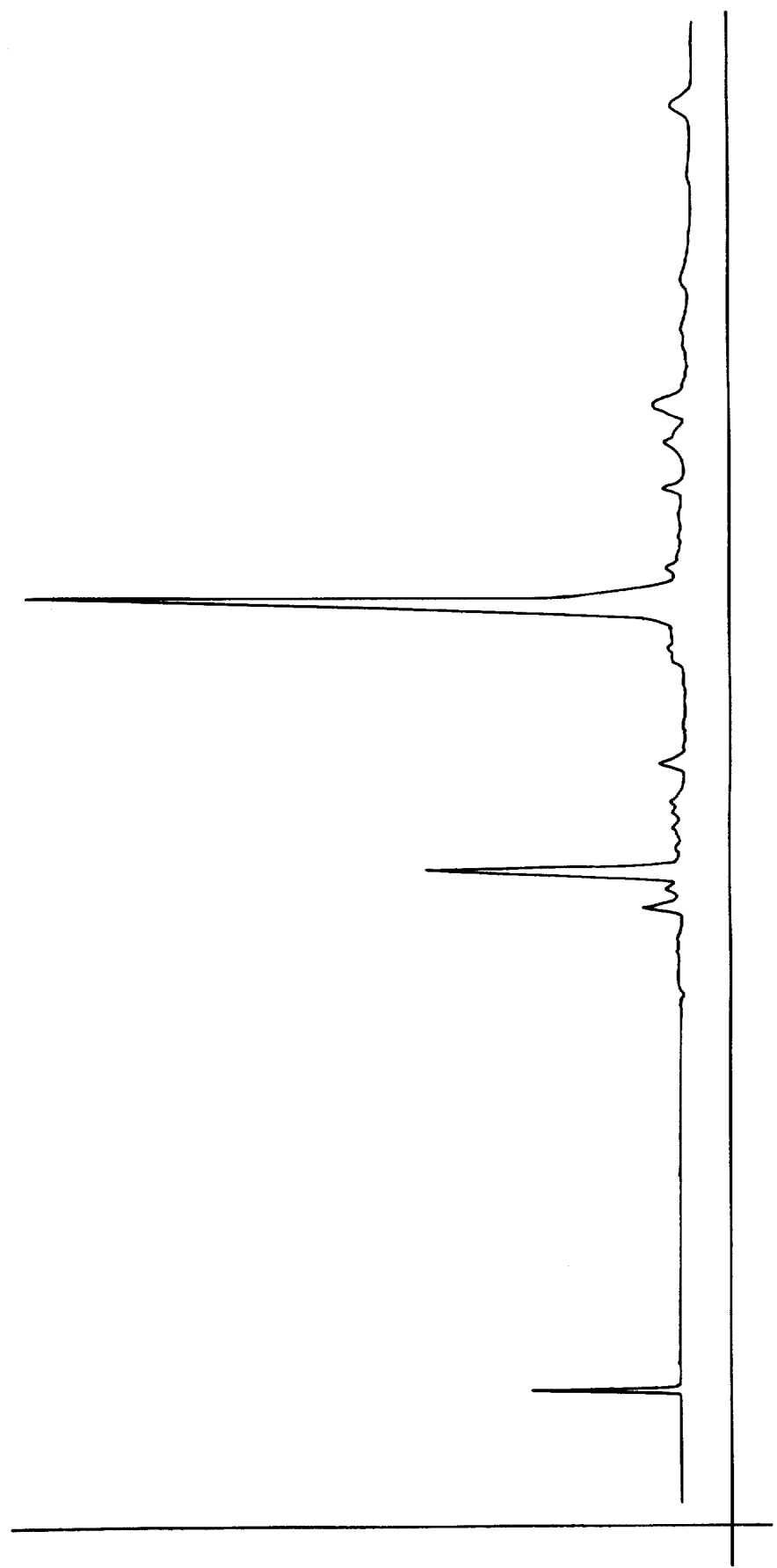
Figure 43:
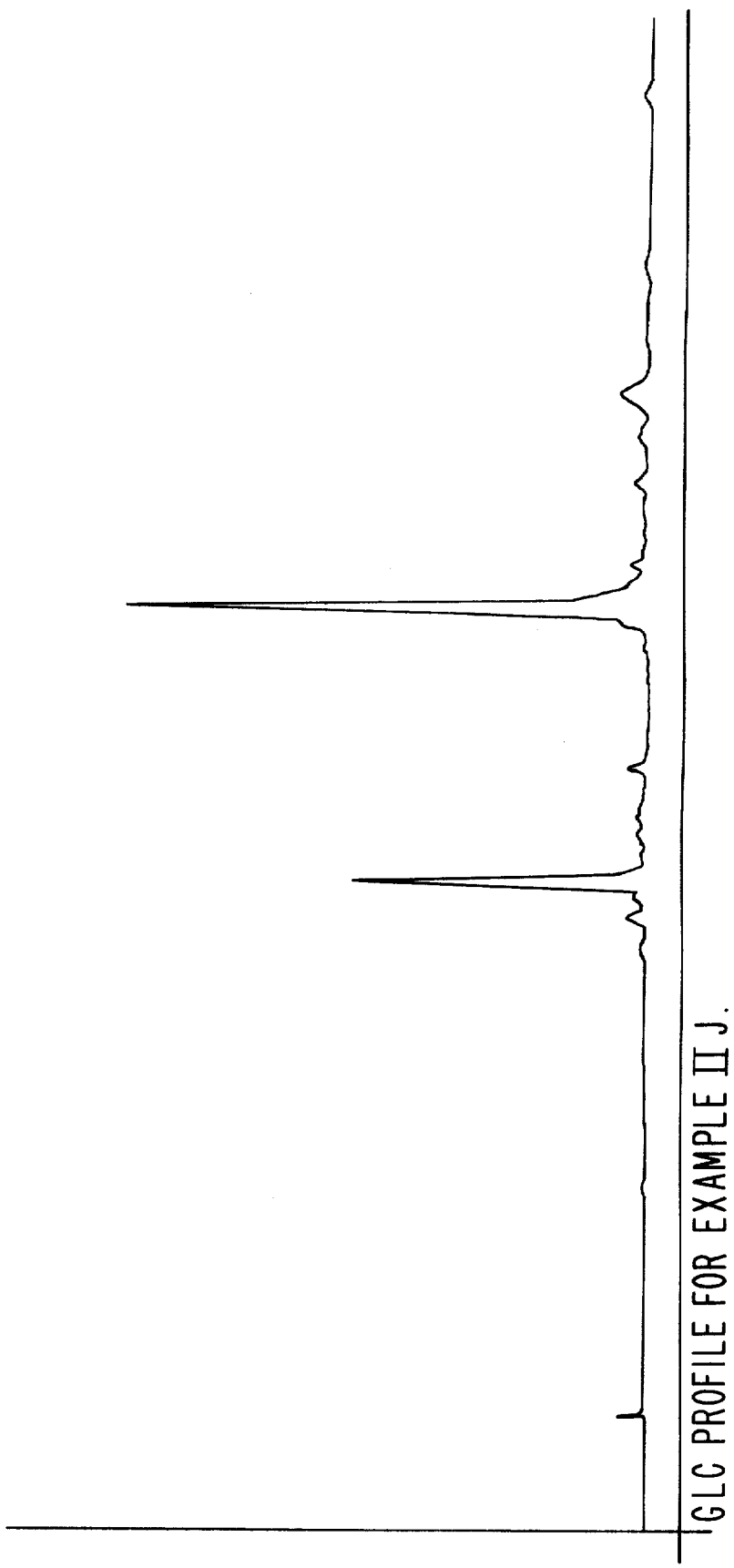
Figure 44:
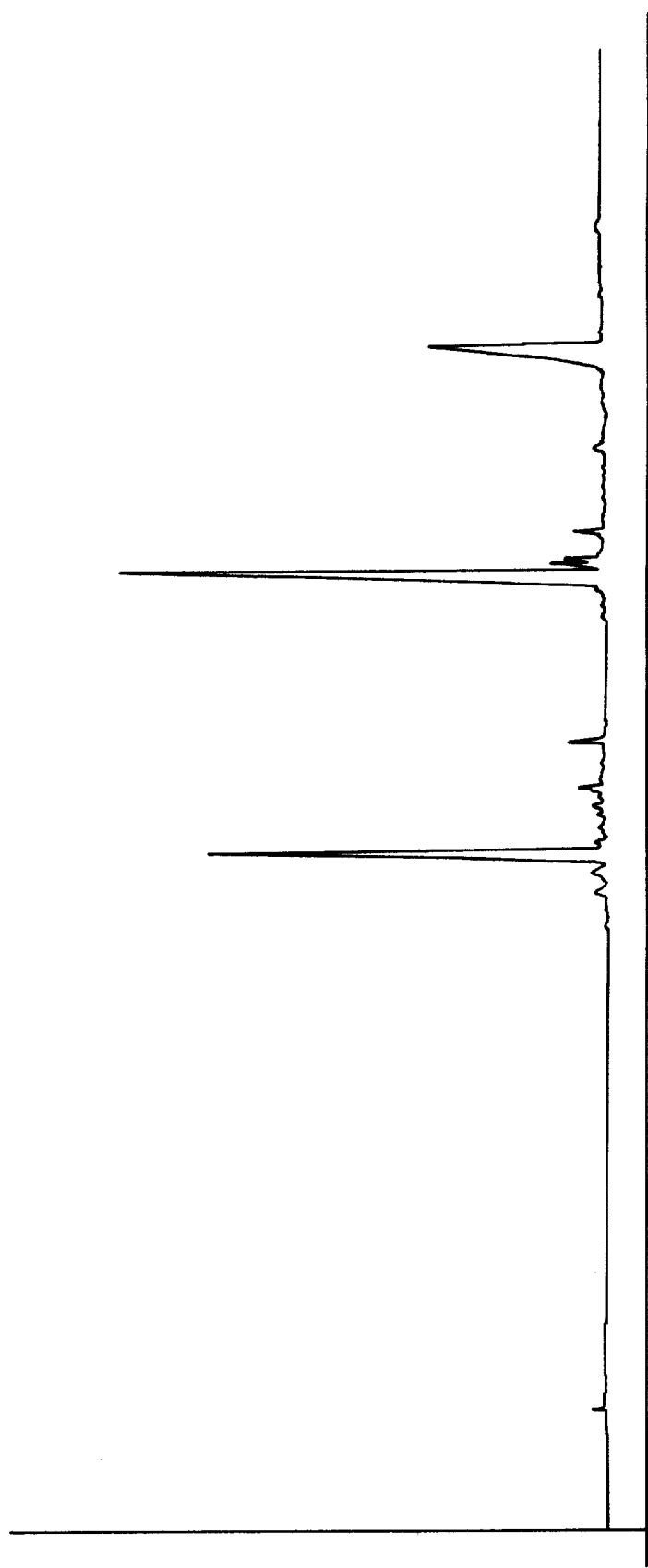
Figure 45:
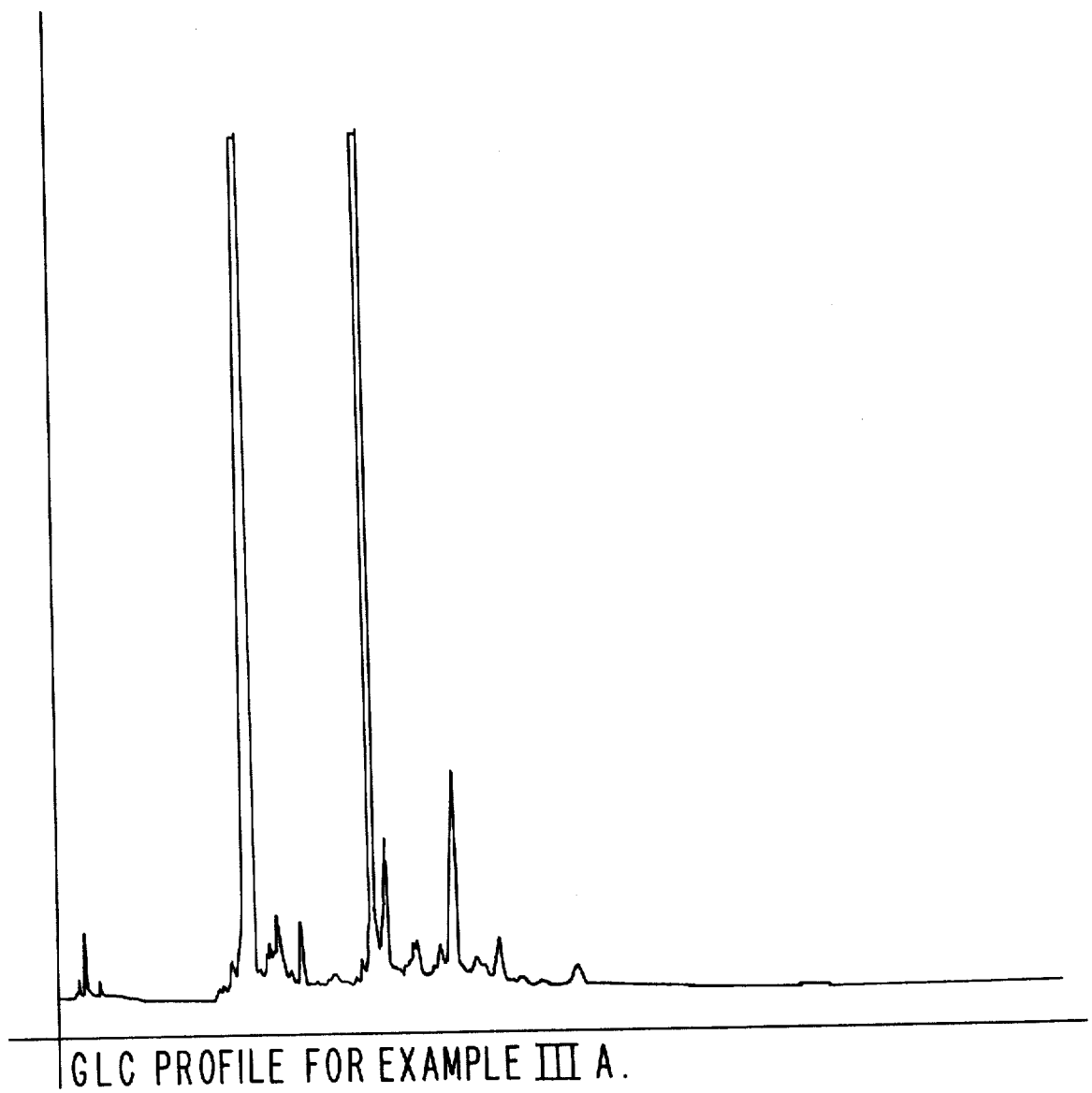
Figure 46:
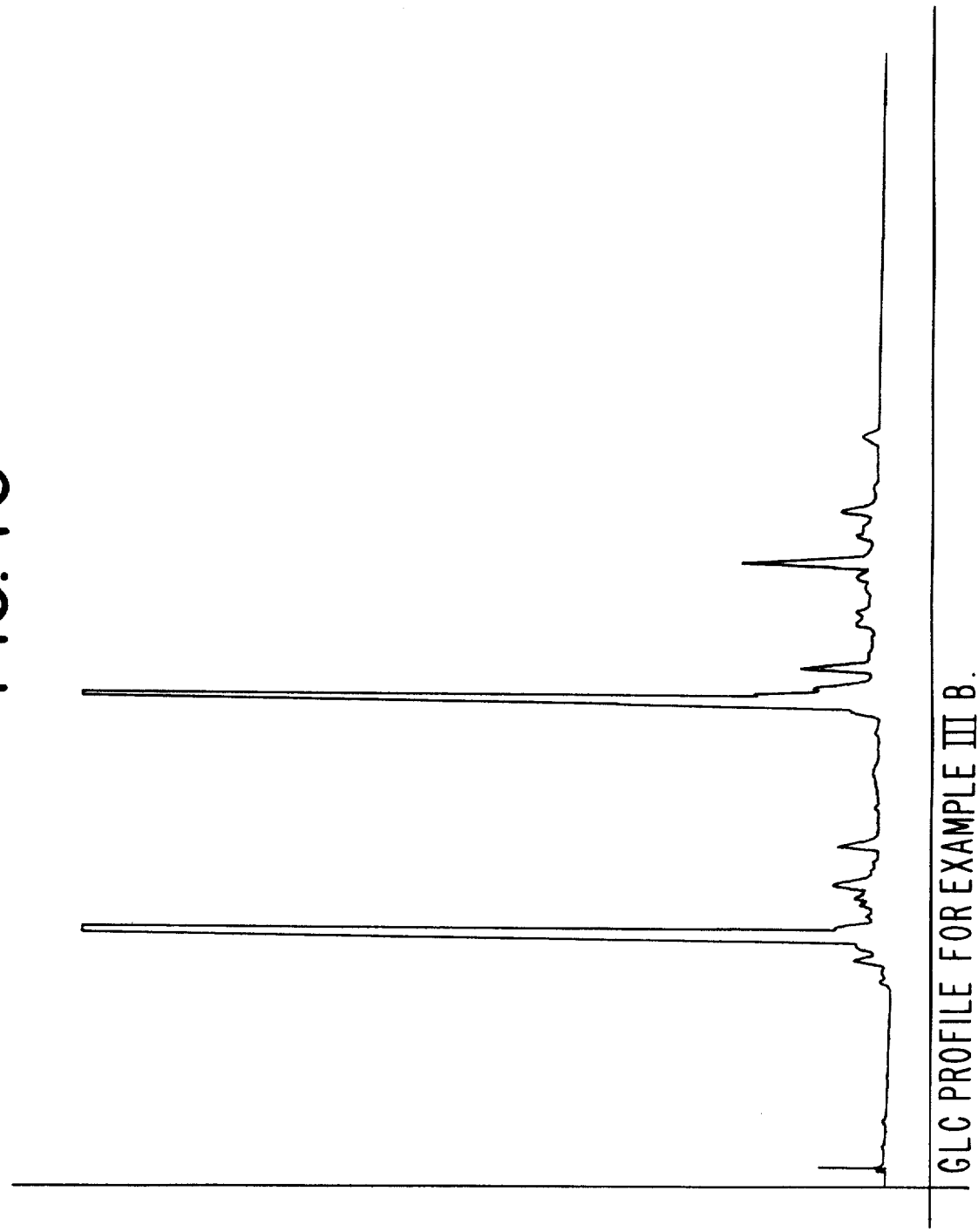
Figure 47:
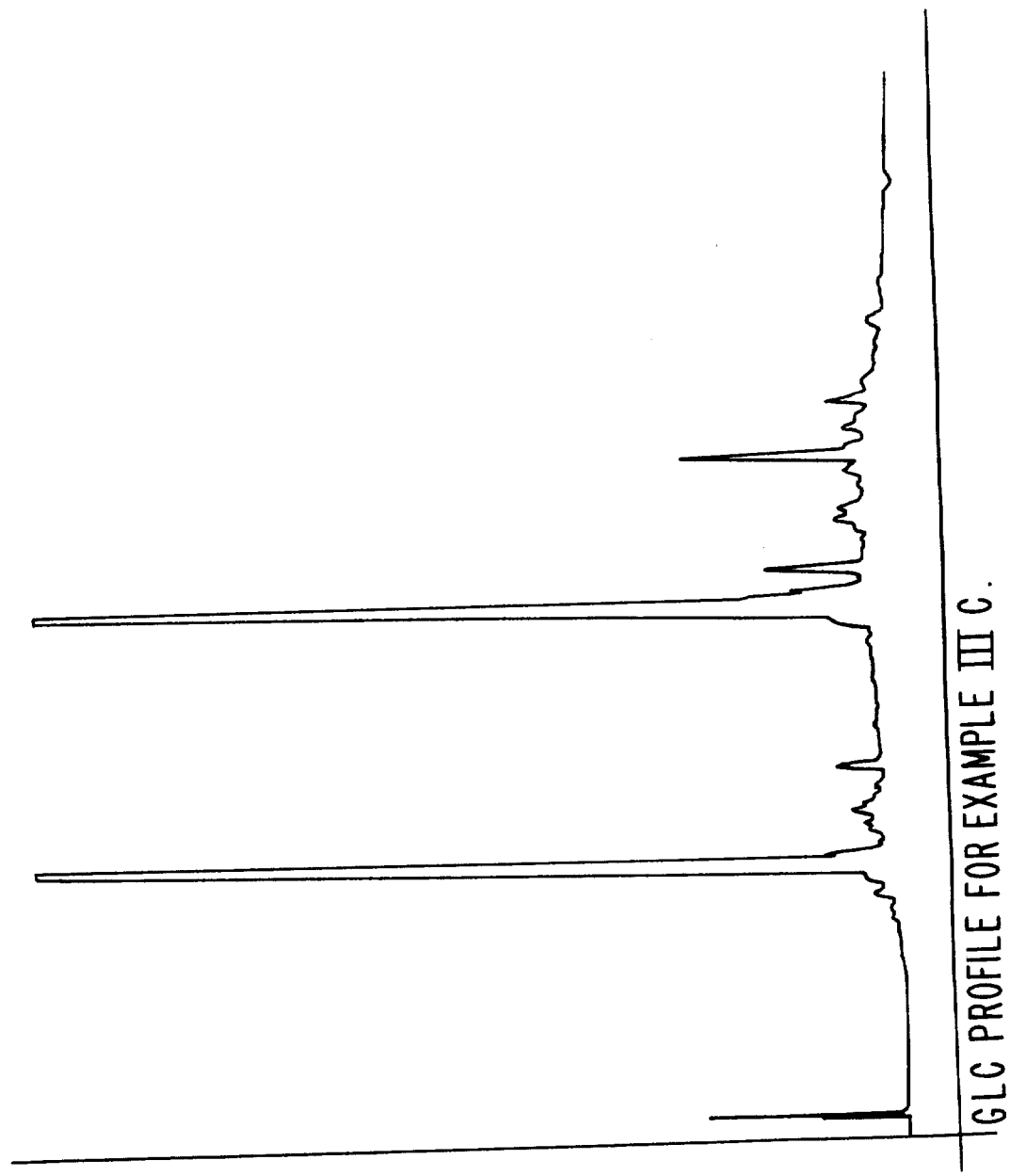
Figure 48:
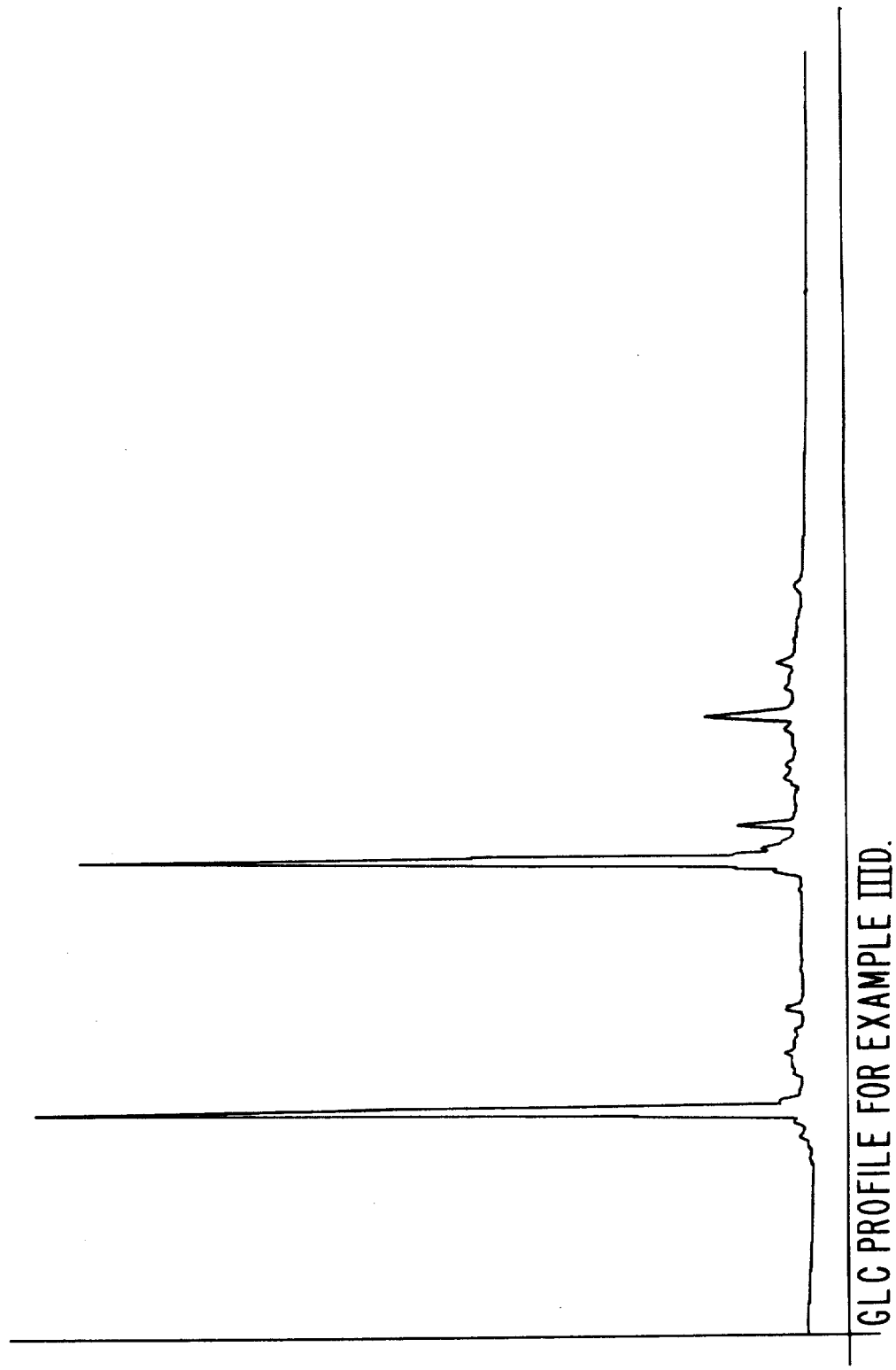
Figure 49:
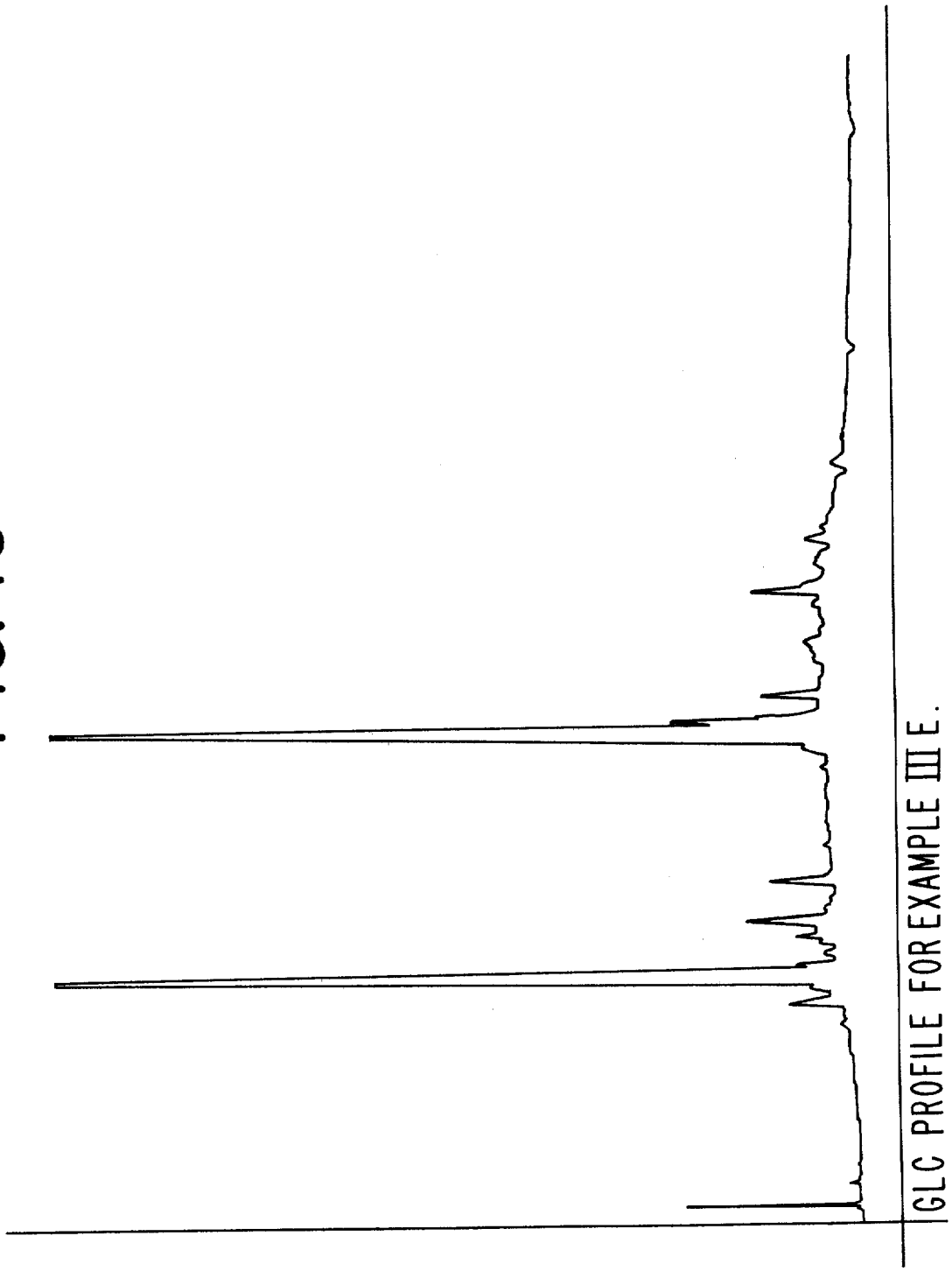
Figure 50:
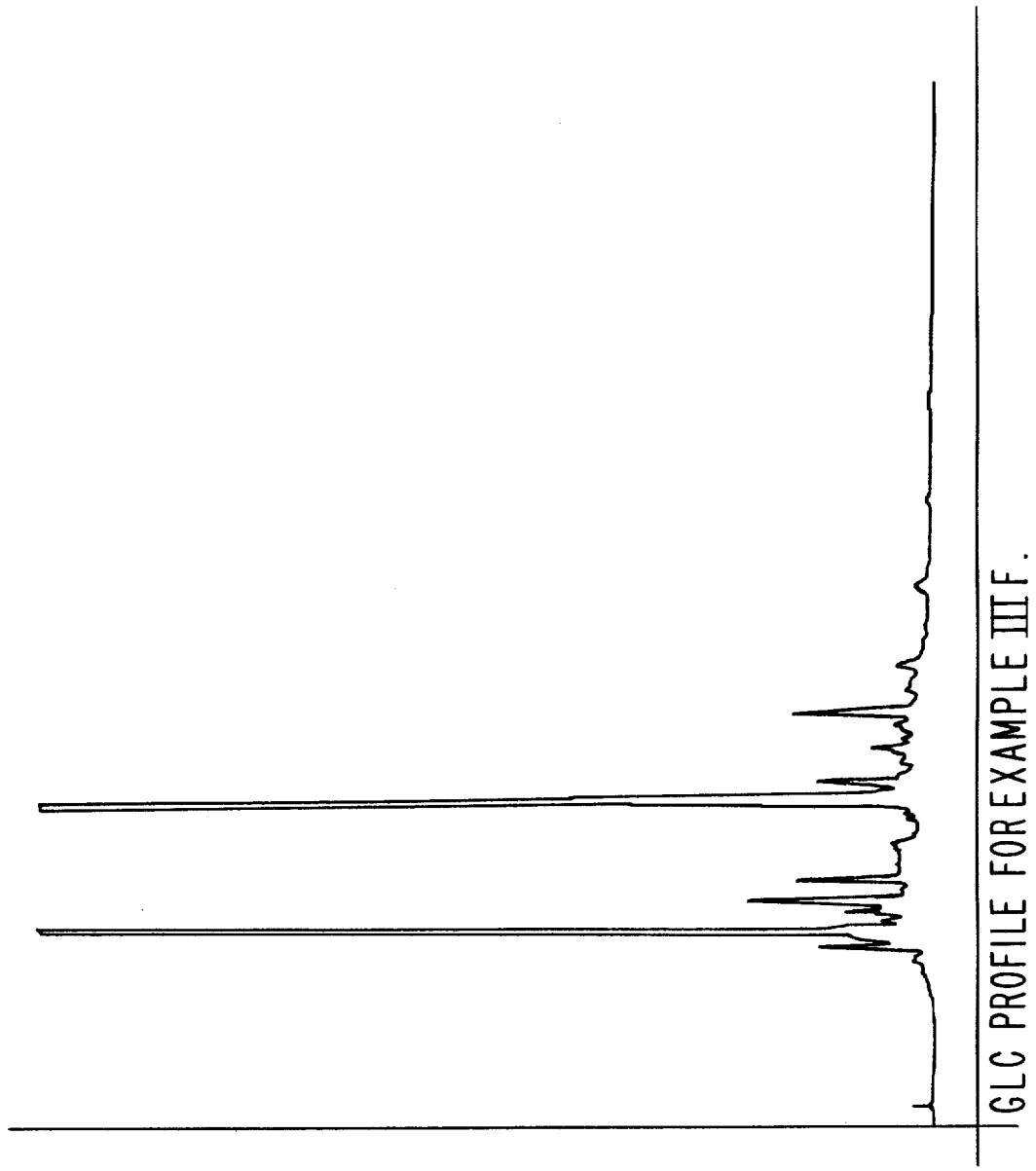
Figure 51:
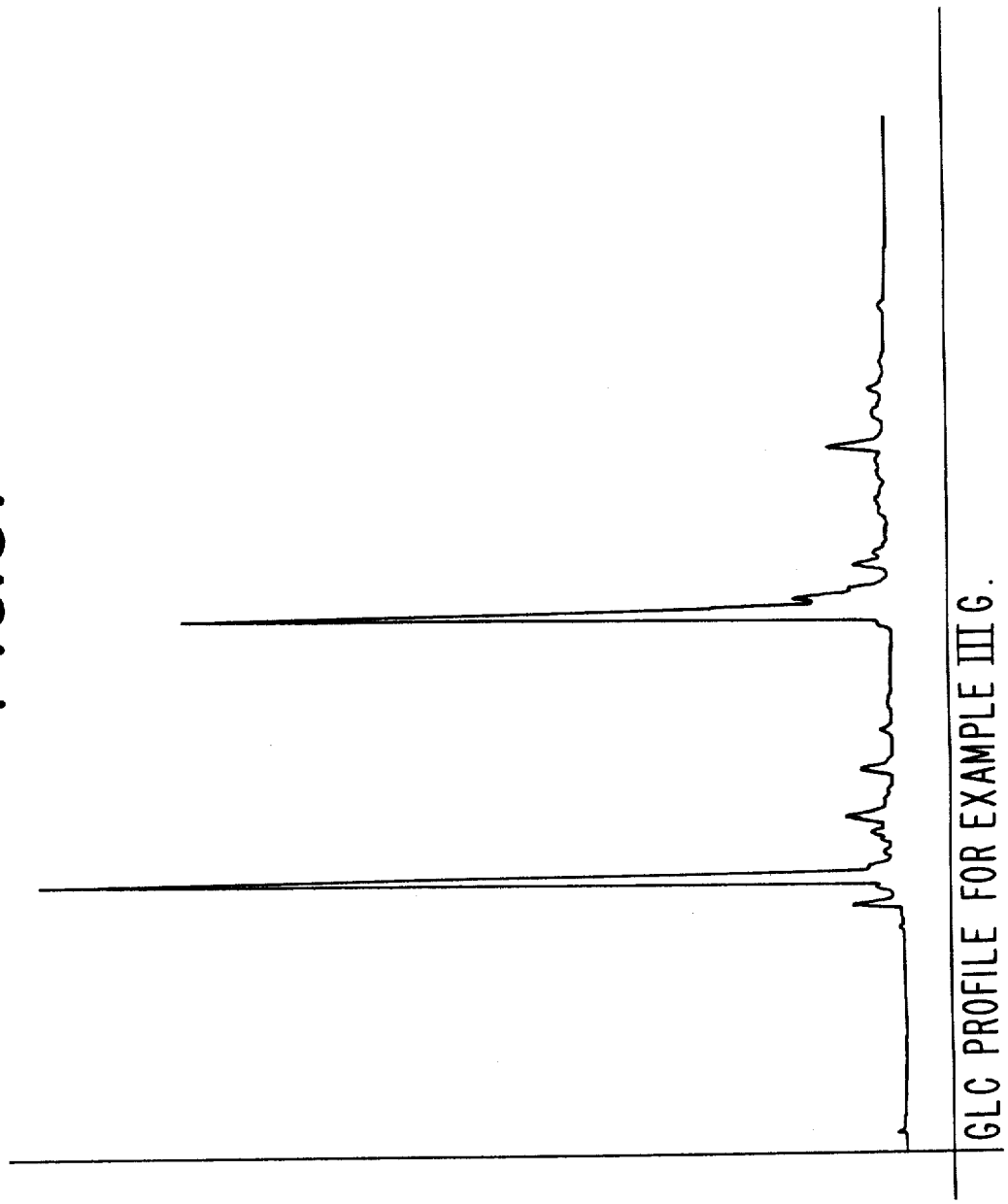
Figure 52:
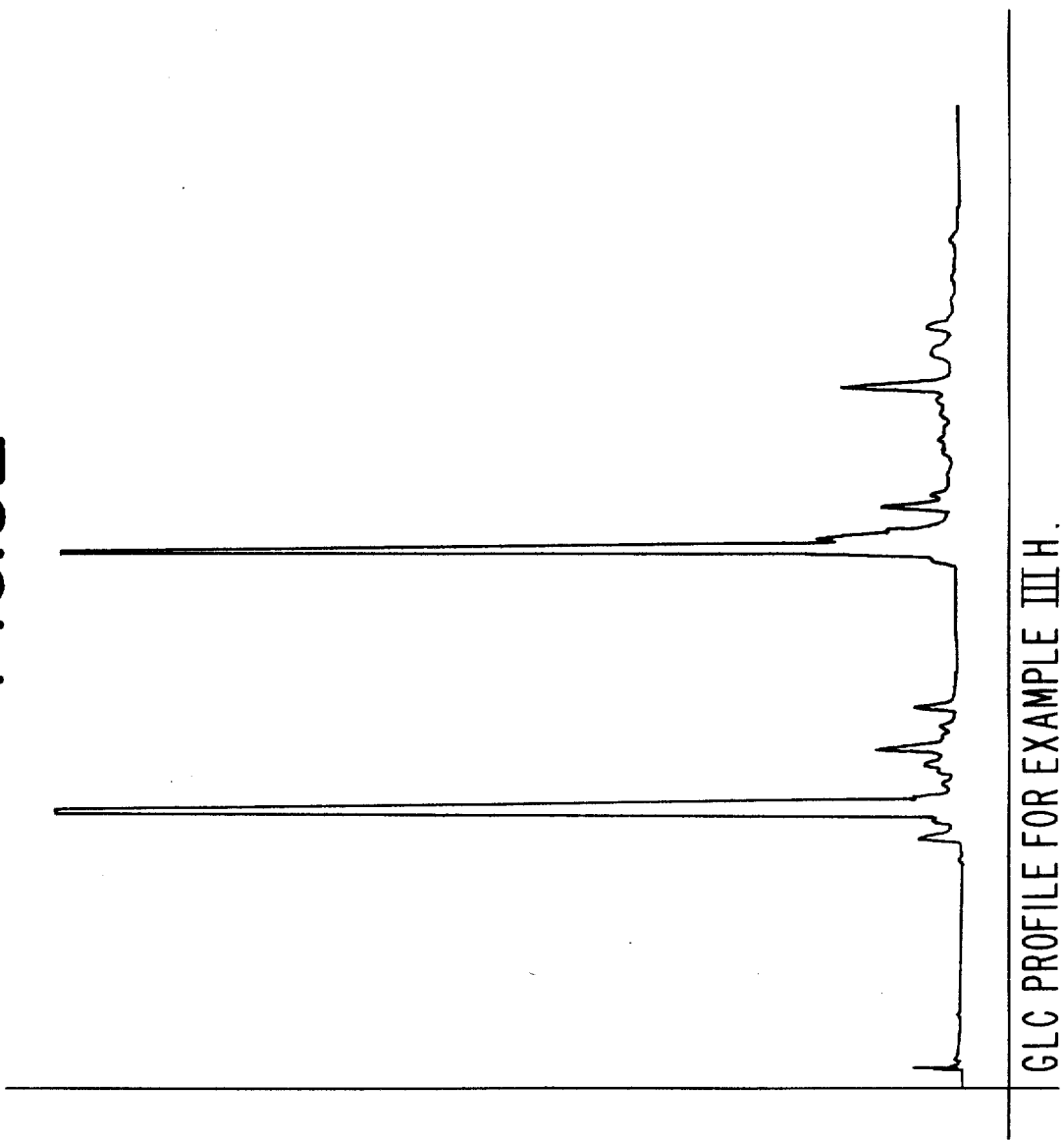
Figure 53:
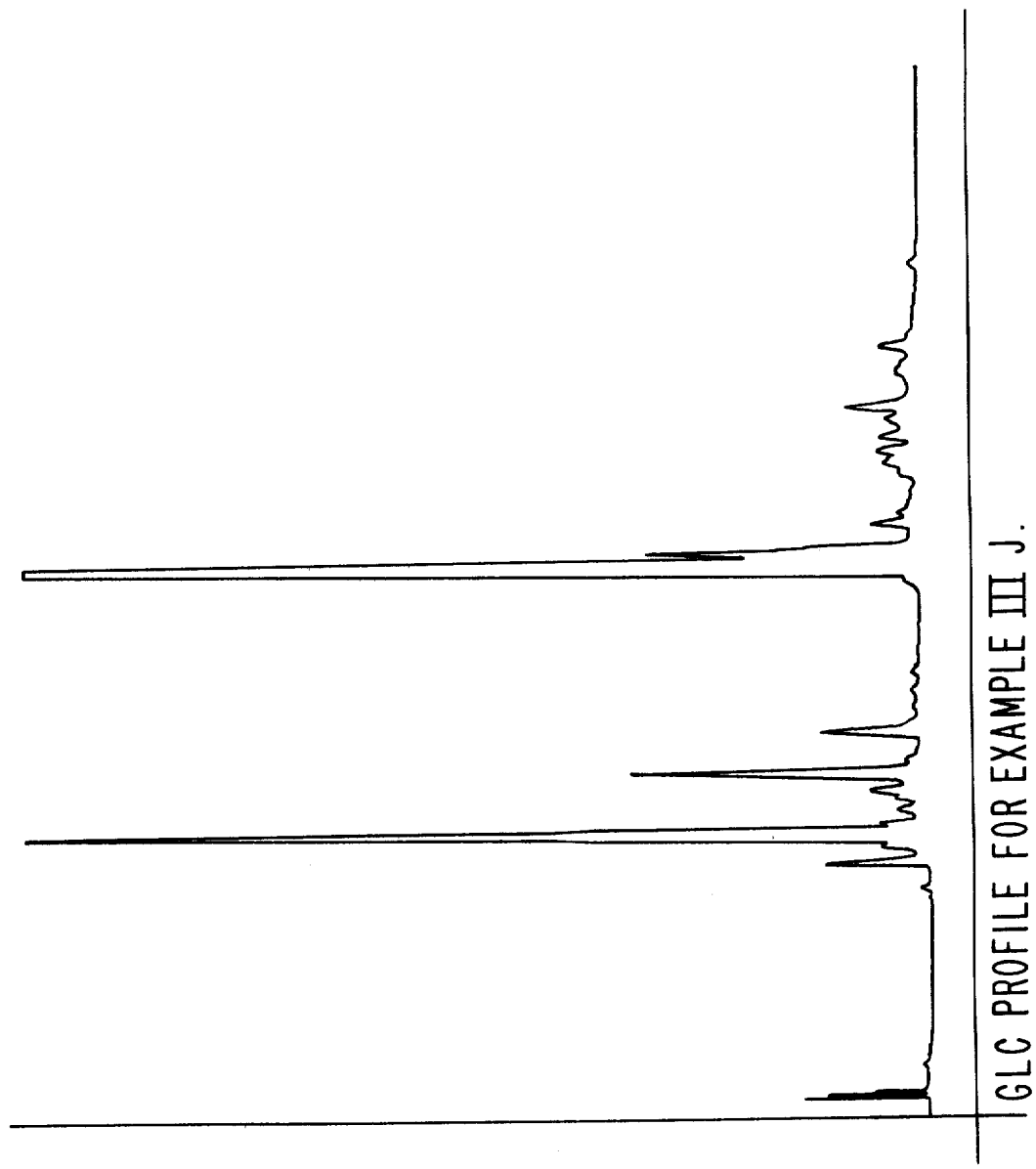
Figure 54:
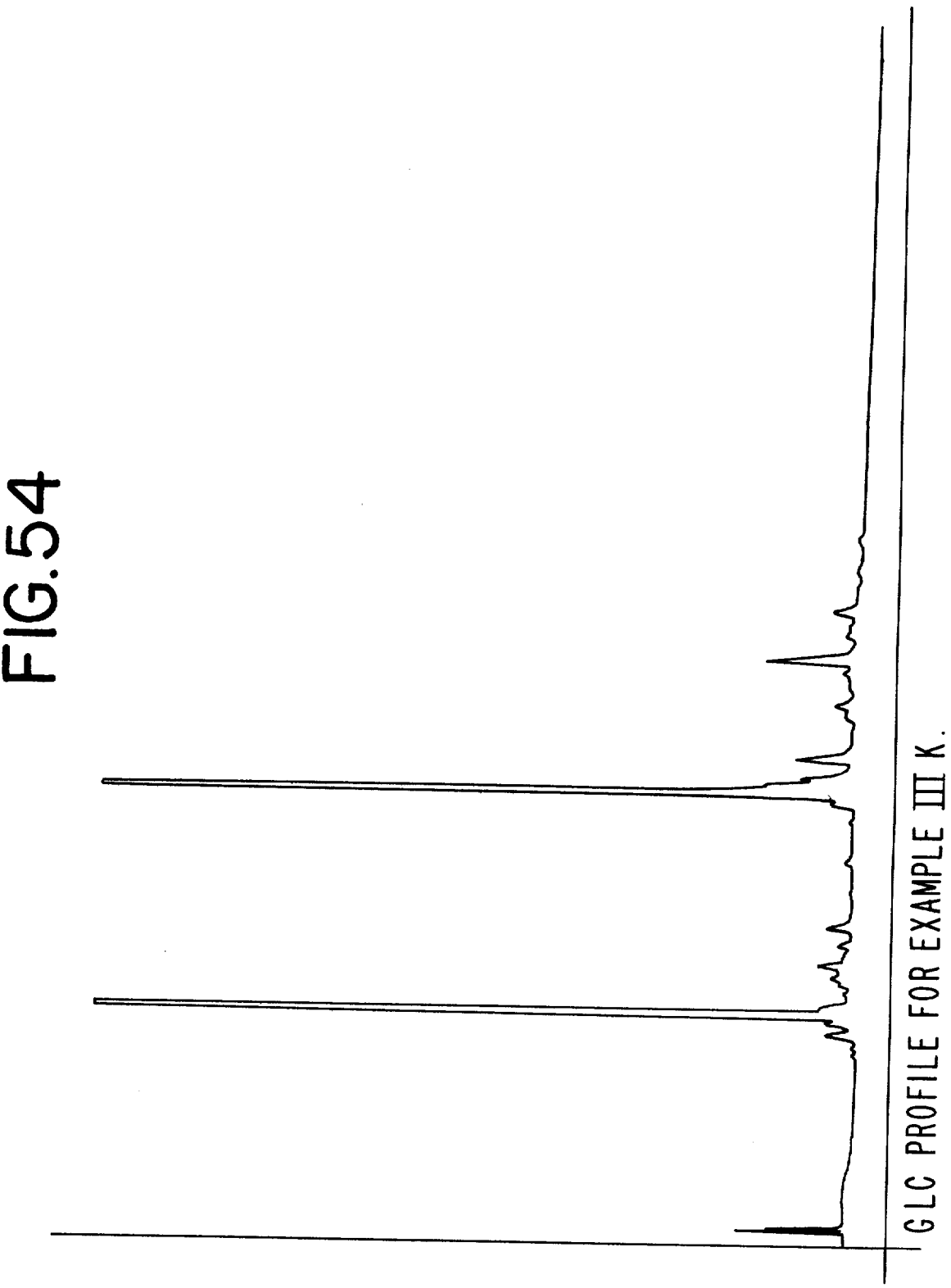

FIG. 34 is the infra-red spectrum for the organic phase of the steam distillation product produced according to Example I(C).

FIGS. 35, 36, 37, 38, 39, 40, 41, 42, 43 and 44 are GLC profiles for the organic phases of steam distillation products produced according to the processes of Examples II(A), II(B), II(C), II(D), II(E), II(F), II(G), II(H), II(J) and II(K) using the heartwood of sections of a *Juniperus Mexicana* tree which is the subject of the schematic diagram of FIG. 57 infra. The following table sets forth the GLC profile figure number, example number and tree section relating to the tree section of the schematic diagram of FIG. 57:

TABLE I

| Figure Number | Example Number | Tree Section |
|---|---|---|
| 35 | II(A) | 809-A |
| 36 | II(B) | 809-B |
| 37 | II(C) | 809-C |
| 38 | II(D) | 814-A |
| 39 | II(E) | 814-B |
| 40 | II(F) | 814-B |
| 41 | II(G) | 814-B |
| 42 | II(H) | 804-B |
| 43 | II(J) | 804-C |
| 44 | II(K) | stump (801) |

The following FIGS. 45, 46, 47, 48, 49, 50, 51, 52, 53 and 54 set forth GLC profiles for the organic phase of steam distillates produced according to the process of steam distillation of *Juniperus Mexicana* trees previously treated with compounds defined according to the structure:

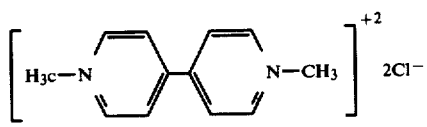

in accordance with Examples III(A), III(B), III(C), III(D), III(E), III(F), III(G), III(H), III(J) and III(K) as specifically set forth in Table II below:

TABLE II

| Example Number | Figure Number | Tree Number |
|---|---|---|
| III(A) | 45 | 49 (base) |
| III(B) | 46 | 49 (middle) |
| III(C) | 47 | 49 (top) |
| III(D) | 48 | 49 (branch) |
| III(E) | 49 | 11 (base) |
| III(F) | 50 | 11 (top) |
| III(G) | 51 | 12 (base) |
| III(H) | 52 | 12 (top) |
| III(J) | 53 | 35 (base) |
| III(K) | 54 | 35 (base) |

FIG. 55 is a schematic flow diagram of the process used to produce *Juniperus Mexicana* oil as carried out in practice.

FIG. 56 is a diagram of the laboratory apparatus and to carry out an extraction of untreated chips of aged or green *Juniperus Mexicana* in order to emulate the commercial prior art techniques.

FIG. 57 is a schematic diagram of a *Juniperus Mexicana* tree indicating numerically various sections tested in order to ascertain quantities of high thujopsene-containing cedarwood oil in various sections of said *Juniperus Mexicana* tree.

FIGS. 58, 59, 60, 61, 62, 63, 64 and 65 are diagrams illustrating a preferred method of treatment of the *Juniperus Mexicana* trees using the bipyridylium salts as embodied in U.S. Pat. No. 3,971,159, the specification of which is incorporated by reference herein.

Figure 58:
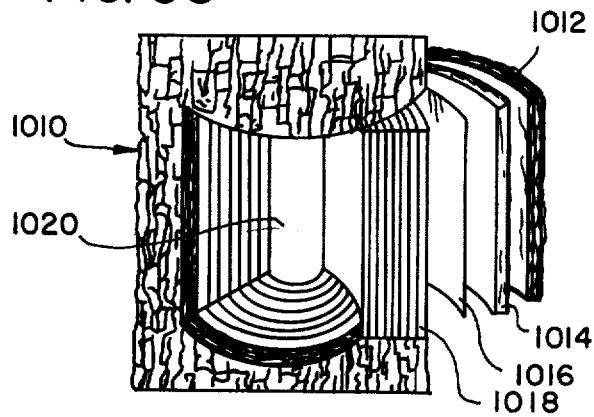

FIG. 58 shows the layers of *Juniperus Mexicana* to be treated.

Figure 59:
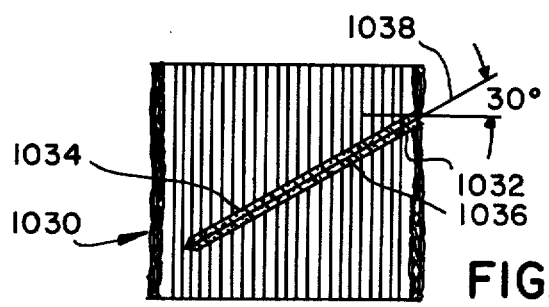

FIGS. 57, 58 and 59 show a single treatment site of the *Juniperus Mexicana*.

Figure 62:
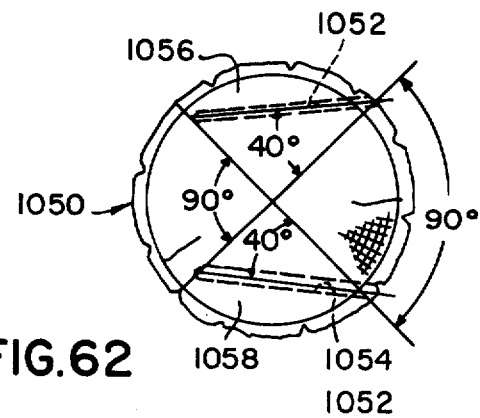
Figure 63:
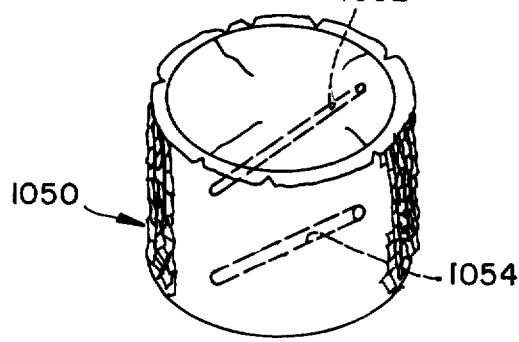

FIGS. 62 and 63 show the use of two treatment sites.

Figure 64:
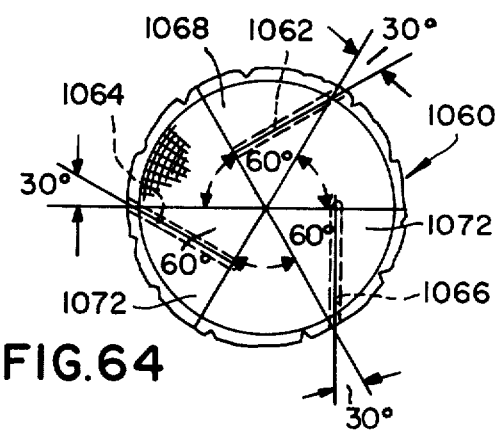
Figure 65:
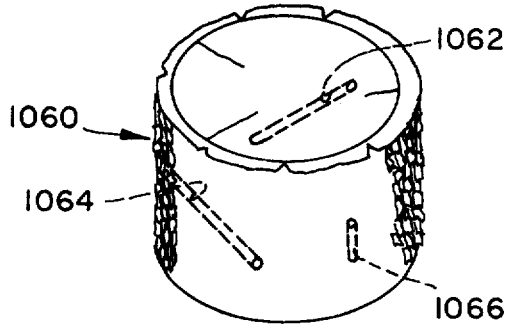

FIGS. 64 and 65 show the use of three treatment sites of the *Juniperus Mexicana* using the bipyridylium salts.

Figure 66:
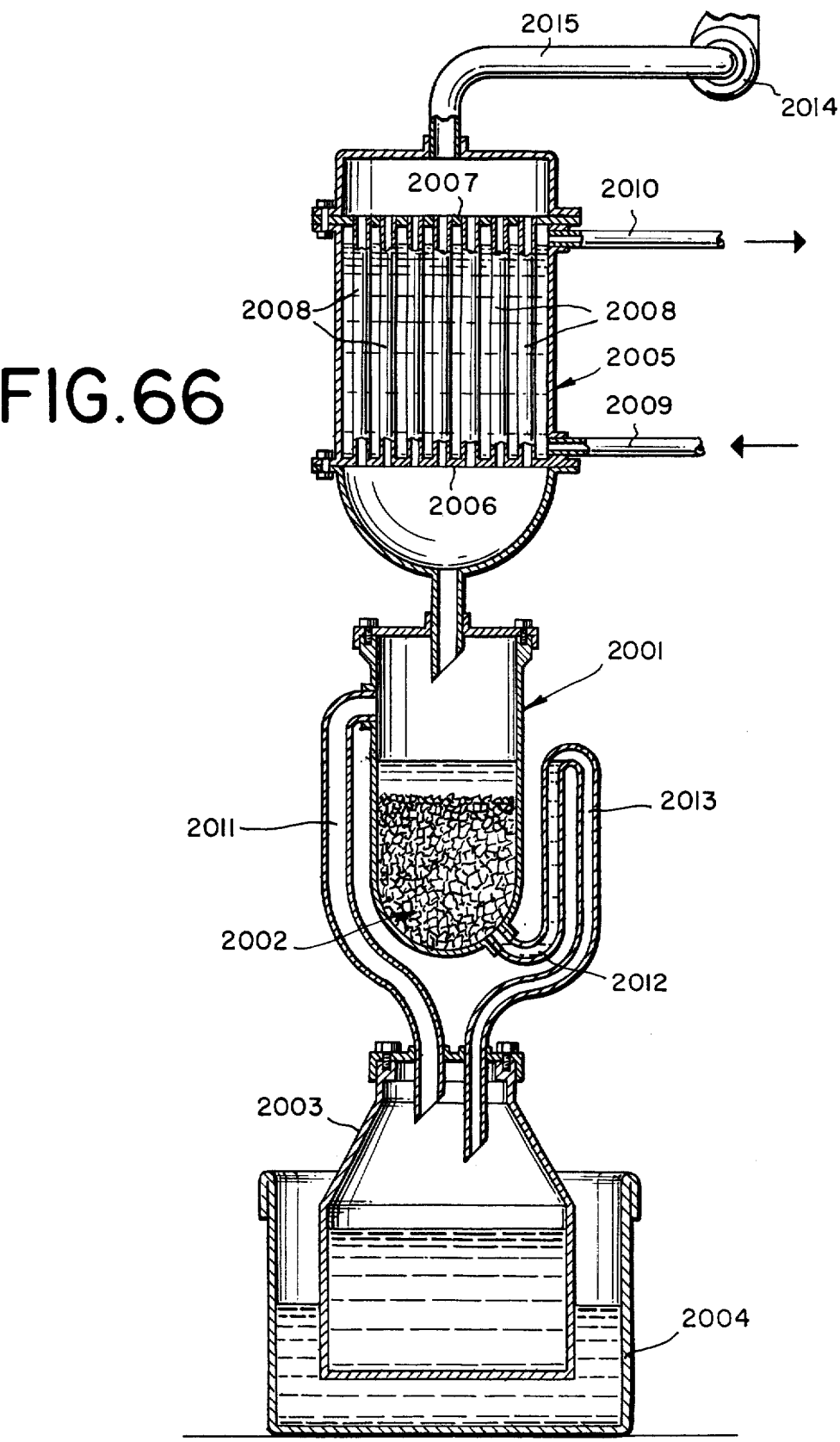

FIG. 66 is a diagram of the extraction apparatus useful in the practice of the extraction of the *Juniperus Mexicana* chips "A", aged or green, which can be used to replace the steam distillation column and is shown using the reference numeral "95" in FIGS. 4, 5, 6, and 7, supra.

DETAILED DESCRIPTION OF THE DRAWINGS AND PREFERRED EMBODIMENTS OF THE INVENTION

FIG. 1 is the GLC profile for high thujopsene-containing cedarwood oil produced from *Juniperus Mexicana* according to the process diagrammed by means of the schematic diagram in FIG. 57. Conditions of GLC operation: 10'×0.125" 5% Carbowax column programmed at 100°-220° C. at 4° C. per minute; chart speed 0.4 cm per minute.

The peak indicated by reference numeral "1" is the peak for alpha-cedrene. The peak indicated by reference numeral "2" is for beta-cedrene. The peak indicated by reference numeral "3" is for thujopsene. The peak indicated by reference numeral "4" is for alpha-chamigrene. The peak indicated by reference numeral "5" is for cuparene. The peak indicated by reference numeral "6" is for isolaurene. The peak indicated by reference numeral "7" is for delta-cadinol. The peak indicated by reference numeral "8" is for cedrol. The peak indicated by reference numeral "9" is for widdrol.

Figure 2B:
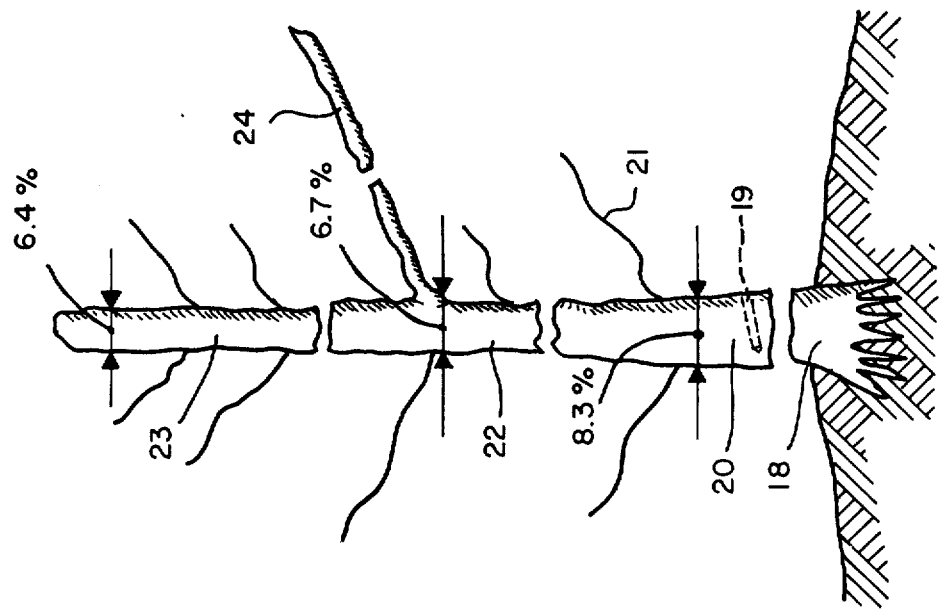
FIGS. 2A and 2B are schematic diagrams of cedarwood trees.
Figure 2A:
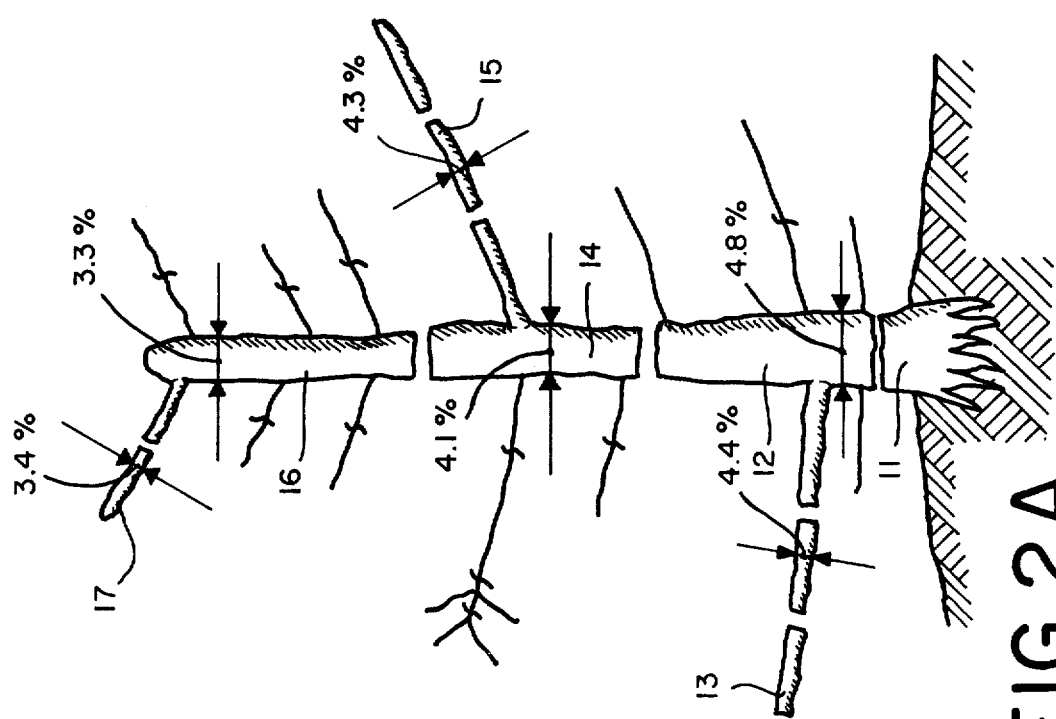

FIGS. 2A and 2B are diagrams of *Juniperus Mexicana* trees showing percentages of high thujopsene-containing cedarwood oil in various parts of said trees. FIG. 2A is a *Juniperus Mexicana* tree in schematic diagram form not having been pre-treated during the growth stage (12 months prior) with a 1% aqueous solution of PARAQUAT ®, a compound having the structure:

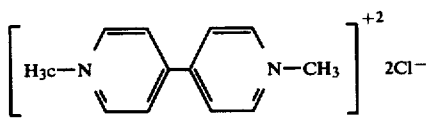

The schematic diagram of the tree in FIG. 2B is for a Juniperus Mexicana tree treated 12 months prior to testing with a 1% aqueous PARAQUAT ® solution with the point of application being indicated by reference numeral "19".

Referring in detail to FIGS. 2A and 2B; the region indicated by reference numeral "11" is the base of the untreated Juniperus Mexicana tree. The region indicated by reference numeral "13" is a lower branch of the Juniperus Mexicana tree containing 4.4% by weight of high thujopsene-containing cedarwood oil. The region indicated by reference numeral "12" is the lower region of the Juniperus Mexicana tree containing 4.8% by weight of high thujopsene-containing cedarwood oil. The region indicated by reference numeral "14" is the upper midsection of the Juniperus Mexicana tree containing 4.1% by weight of high thujopsene-containing cedarwood oil. The region indicated by reference numeral "15" is an upper branch of the Juniperus Mexicana tree containing 4.3% by weight of high thujopsene-containing cedarwood oil. The region indicated by reference numeral "16" is the upper "top" portion of the Juniperus Mexicana tree containing 3.3% by weight of high thujopsene-containing cedarwood oil. The region indicated by reference numeral "17" is an upper branch of the Juniperus Mexicana tree containing 3.4% by weight of high thujopsene-containing cedarwood oil. Referring to FIG. 2B, the region indicated by reference numeral "18" is the base region ("stump") of the treated Juniperus Mexicana tree. As stated supra, the region indicated by reference numeral "19" is the point of application of the 1% aqueous solution of PARAQUAT ® having the structure:

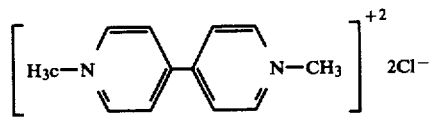

The region indicated by reference numeral "20" is the lower midsection of the Juniperus Mexicana tree containing 8.3% by weight of high thujopsene-containing cedarwood oil (12 months subsequent to treatment at point "19" with 1% aqueous PARAQUAT ®). The region indicated by reference numeral "21" is a lower branch of the Juniperus Mexicana tree containing 7.3 % by weight of high thujopsene-containing cedarwood oil. The region indicated by reference numeral "22" is the upper midsection of the Juniperus Mexicana tree containing 6.7% by weight of high thujopsene-containing cedarwood oil. The region indicated by reference numeral "23" is the upper portion (top) of the Juniperus Mexicana tree containing 6.4% by weight of high thujopsene-containing cedarwood oil. The region indicated by reference numeral "24" is the upper branch of the Juniperus Mexicana tree. The point of application 19 is created by means of a drill application analogous to that set forth in U.S. Pat. No. 3,971,159 issued on July 27, 1976, the specification of which is incorporated by reference herein.

FIG. 3 sets forth the laboratory equipment used to determine an appropriate optimal procedure for extracting high thujopsene cedarwood oil from treated or untreated chips of the Juniperus Mexicana tree and thus testing the effectiveness of the use of the compounds defined according to one of the structures:

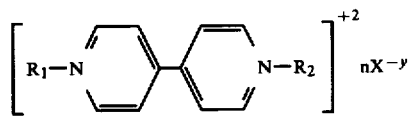

or

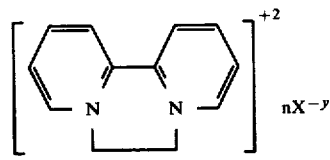

Steam from source 30 under high pressure is passed through steam line 31 at a pressure measured using a pressure gauge 32 into "Y" adapter 33 through vacuum hose 34 into a super-heating three-neck flask 42 heated using heating mantle 41. Condensate from the steam is collected in separatory funnel 35 to which is connected steam vent or relief valve 36 useful for venting excess steam through line 38 into sink 37. The super-heated steam whose temperature is measured using thermometer 40, is passed into steam distillation column 44 which is an 18" jacketed glass column in which is located chips of Juniperus Mexicana either treated with PARAQUAT ® or other compound defined according to one of the structures:

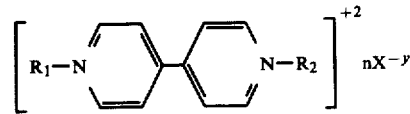

or

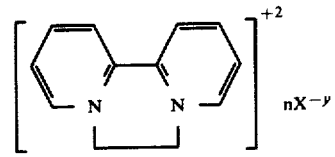

wherein $R_1$, $R_2$, X, n and y are defined supra, through glass wool trap 43 and Goodloe packing 43a into condenser line 46 through condenser 47 which is cooled using inlet water at 49 and which exits at outlet 48. The condensed two-phase system at 50 enters Bidwell trap 51 to which is connected separatory funnel 52 wherein high thujopsene cedarwood oil and water is collected. Steam condensate passes through line 54 into three-neck separatory funnel 62, stirred using stirrer 63 driven by a motor 55. Extractive solvent in extractive solvent holding tank 57 (e.g. diethylether) is added together with saturated aqueous sodium chloride or potassium chloride from tank 60, through "Y" adapter 59 and "Y" adapter 61 into said three-neck separatory funnel 62 in order to cause an extraction of the aqueous phase. The extract is removed and subsequently concentrated, dehydrated and combined with dehydrated oil from separatory funnel 52 for subsequent fractional distillation.

A similar process is carried out using the commercial equipment as set forth in FIGS. 4, 5, 6 and 7.

The operation of this apparatus is set forth in exemplary form in detail in Examples II and III, infra.

Referring to FIG. 4, *Juniperus Mexicana* trees are treated at 76 at a time t-12 months, t-6 months or t-3 months with at least one compound defined according to one of the structures:

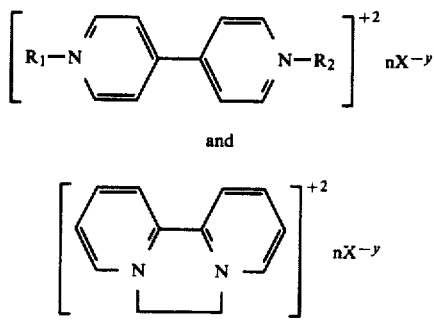

and wherein $R_1$, $R_2$, X, n and y are defined supra, from a PARAQUAT® source 70 through valve 75, pump 71 and line 72, the bipyridylium salt or salts being in liquid form either in aqueous or alcoholic or aqueous/alcoholic solutions. The treatment can be by means of spraying on the leaves or by insertion into the bark or into a drilled hole as exemplified in U.S. Pat. No. 3,971,159 issued on July 27, 1976, the specification of which is incorporated by reference herein, and the technique of which is illustrated in FIGS. 58, 59, 60, 61, 62, 63, 64 and 65, infra. At a point in time=t, either 3, 6 or 12 months subsequent to the treatment with the bipyridylium salts, the *Juniperus Mexicana* trees are cut and the resultant wood is particularized into chips, sawdust or powder at 78 being conveyed through conduit 77. The thus-particularized *Juniperus Mexicana* wood is then placed through conduit 79 in apparatus 80 for feed through line 81 via a pump or conveying mechanism 90 and line 89 into either steam distillation apparatus 95 or solid/liquid extraction apparatus 95. In the event that the apparatus 95 is a steam distillation apparatus, steam from steam source 82 is pased through valve 83 to super-heater 84 or by-passing super-heater 84 through line 85 or both through super-heater 84 and by-pass line 85 is passed through valve 86 and line 88 into column 95 wherein the *Juniperus Mexicana* particularized material is stripped of high thujopsene-containing cedarwood oil and the vaporized material is passed through line 98 and reflux cutter 99 through condenser 101, the oil phase being split and passed through line 110 using pump 111 and valve 112 and the aqueous phase being split at 109 and passed into extractor 102 through line 107. Extractive solvent from source 103 and recycle line 121 is passed into extractor 102 through line 106. The extractive solvent is used to extract the aqueous phase which is then passed into 104 for possible re-extraction through conduit 105. The solvent containing extract obtained from extractor 102 is sent through line 108 into evaporator 115 wherein the overhead vapor (solvent) is passed through line 116, surge tank 117, through line 118 and into recycle line 121 past pumps 119 and valve 120. In the event that the steam distillation apparatus 95 is replaced by a solid/liquid extraction apparatus, the extraction apparatus can be of the type set forth in FIGS. 8, 9, 10, 11, 12, 13, 14 and 15 and specifically described in U.S. Pat. No. 4,313,912 issued on Feb. 2, 1982, the specification of which is incorporated by reference herein. On the other hand, the solid/liquid extraction apparatus can be of the "Soxhlet" type either for operation at atmospheric pressure or at super atmospheric pressure and is illustrated in schematic form in FIG. 66 infra, which embodies apparatus specifically disclosed in U.S. Pat. No. 1,636,550 issued on July 19, 1927, the specification of which is incorporated by reference herein. As a further alternative, however, both steam distillation apparatus and solid/liquid apparatus of the type set forth in FIG. 66 or of the type set forth in FIGS. 8-15 inclusive, infra, may be utilized in series wherreby efficient extraction of the particularized material of the treated *Juniperus Mexicana* tree may be effected. The extractor 102, a liquid/liquid extractor, may be of the type set forth in FIGS. 16-24 inclusive, infra, and specifically described in U.S. Pat. No. 2,665,196 issued on Jan. 5, 1954, the specification of which is incorporated herein by reference.

The extractive solvents used when apparatus 95 is an extractor and useful in apparatus 102 are not limited to diethylether but may also be freon under super-atmospheric pressure, tetrachloroethylene, methylene dichloride, chloroform, toluene, benzene, n-hexane, n-heptane, n-pentane, 2,2,4-trimethyl pentane or combinations of the foregoing. The steam distillation and/or extraction can be carried out at atmospheric pressure or super-atmospheric pressure up to 500 atmospheres and at temperatures high enough for the extraction but not so high as to effect decomposition of the high thujopsene cedarwood oil or components thereof and not so high as to effect pyrolysis of the particularized form of the *Juniperus Mexicana*. The residue from the evaporator 115 is passed through line 122 through pump 123 and valve 124 to combine at valve 114 with oil phase emanating from apparatus 95 and passing through line 113. The combined phases are then passed through line 125 into distillation column 126 containing stages or plates 127. The overhead from distillation column 126 passes through line 128 and may be refluxed in part through line 130 using reflux cutter 129. The overhead product containing high thujopsene cedarwood oil is passed through valve 131 and pump 132 into collector 133. The bottoms are passed through line 134 through reboiler cutter 135 which reboils part of the bottoms back through line 136 into distillation column 126. The bottoms are passed through line 137, valve 139 and pump 140 into collecting tank 138. If desired, products held in tanks 133 and 138 may be commercially separated by means of further fractional distillation or commercial chromatographic apparatus. If desired, the spent particularized *Juniperus Mexicana* solid substances at 97 may be re-extracted or resteam distilled in appropriate apparatus such as that described for apparatus 95 through a conduit 96.

FIG. 5 is a modified embodiment of the process flow scheme of FIG. 4 wherein additional apparatus is shown whereby other particularized woods are admixed with the particularized Juniperus Mexicana at production location 78 and/or other particularized *Juniperus Mexicana* is treated using materials other than the bipyridylium salts having the structure:

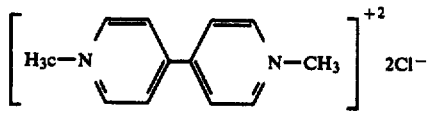

For example, compounds defined according to the structure:

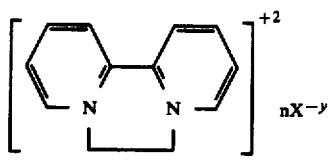

wherein X represents sulfate, n represents 1 and y is −2. Thus, for example, treatment material which is PARAQUAT® having the structure:

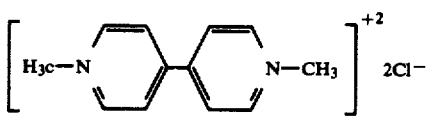

is fed from location 70 into *Juniperus Mexicana* at 76 at time t-12. Simultaneously, compound having the structure:

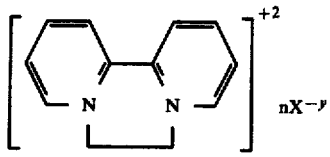

wherein X represents sulfate, n is 1 and y is −2 is fed from location 200A through line 202a to *Juniperus Mexicana* trees at 201 at time t-12. The same trees at time t-10 are treated from location 200B via line 202b with a compound such as 1,1'-diisopropyl-4,4'-biypridylium diiodide (1.8% solution). At time t-3, treatment from location 200C through line 202c to *Juniperus Mexicana* trees at 201 takes place using a 0.3% by weight aqueous solution of 1,1-diethyl-4,4'-bipyridylium dibromide. Green wood at time = t is then particularized at location 78 along with the *Juniperus Mexicana* treated at location 76 by the PARAQUAT® from location 70. Simultaneously therewith, trees of a different species, for example, may be treated at location 206. Thus, for example, at location 206, there are 40 trees of the species *Pinus elliottii* (slash pine). These trees are treated at t-12 using PARAQUAT® from location 204A through line 205a (0.7% by weight aqueous treating solution of 1,1'-dimethyl-4,4'-bipyridylium dichloride). At t-6 from location 204B through line 205b to tree location 206, the *Pinus elliottii* is treated with a 0.4% solution of 1-ethyl-1'-isopropyl-4,4'-bipyridylium dichloride. At t-3 from location 204C through line 205c to location 206, the *Pinus elliottii* is treated with 1,1'-di-n-propyl-4,4'-bipyridylium difluoride. At time = t the *Pinus elliottii* is cut according to the teachings of Example I at column 5 of U.S. Pat. No. 3,971,159 issued July 27, 1976, the specification for which is incorporated herein by reference, and the wood is then particularized along with the wood of the *Juniperus Mexicana* at location 78, the thus-mixed woods are then used to make a pre-planned essential oil using the equipment as set forth in FIG. 5 in precisely the same manner as the equipment of FIG. 4 is used. Thus, treated *Juniperus Mexicana* trees from location 201 are fed into production location 78 through line 203. On the other hand, other treated particularized woods are fed into production location 78 through line 207.

Referring to FIG. 6, it sets forth the apparatus and process flow diagram of FIG. 4 with the inclusion of additional computer program control apparatus 199 whereby the output of high thujopsene content containing cedarwood oil controls various fluid feed and bipyridylium salt feed inputs. Thus, valve 75 in the flow line of the PARAQUAT® into the *Juniperus Mexicana* tree area is controlled through control system 75C and 199C with electronic programmer system 199. The opening and closing and degree of flow through valve 75 is determined by the output of analyzers 197 and 198 through control systems 197C and 198C and through control systems 133C and 138C (concerning quantities of high thujopsene-containing cedarwood oil flowing into apparatus 133 and apparatus 138). The operation of the actual treatment is controlled through control system 76C. The operation of valve 120 is controlled through valve control system 120C and control system 199C. The operation of valve 83 controlling the steam super-heat line and super-heat by-pass line 85 is controlled through control system 83C.

The operation of valve 86 controlling the flow of steam into distillation column 95 is operatively controlled through control line 86C and control line 199C.

The operation of solid/liquid extractor or steam distillation column 95 is controlled through control system 95C and control line 199C. The operation of reflux cutter 99 and the reflux system 98/99/100 is controlled through control system 99C. The operation of the separation valve and system 109 for separating the organic phase from the aqueous phase is controlled through control system 109C and control line 199C. The operation of valve 124 in the line 122 (for the evaporator residue) is controlled through control system 124C and 199C. The operation of valve 114 for control of feed into distillation column 126 is controlled through control system 114C. The operation of re-boiler cutter 135 is controlled through control line 135C and control system 199C. The operation of valve 139 in the line 137 is controlled through control system 139C and control system 199C.

FIG. 7 shows the use of apparatus identical to that set forth in FIG. 5 and the use of the control systems of FIG. 6 and, in addition, control systems 203C and 207C operatively connected to the program control apparatus 199 through a control line 199C governing the input from treatment areas 201 (through control system 201C and control system 199C) and with input area 206 (through control system 206C and control system 199C).

The solid/liquid extraction apparatus which can be used for the apparatus indicated by reference numeral "95" in FIGS. 4, 5, 6 and 7 is set forth in detail in FIGS. 8-15 inclusive.

Thus, in an embodiment as illustrated in FIG. 8, the multiple-stage extractor 310 is provided with four processing sections or stages indicated generally as stages 312, 314, 316 and 318, although the number of stages can be varied in accordance with the desired volume flow and depth of material to be processed. Beneath the last stage 318 is the process material removal stage 320 from which the slurry of particularized wood which has been sequentially processed through each of the prior stages, is removed for subsequent processing and/or for disposal.

A single drive motor 322 drives all of the rotating apparatus in each of the stages through a gear reduction device 324 as described more fully infra. The material to be processed is introduced through a feed screw conveyor 326 where it is introduced into the upper region of the first extractor section 312.

Referring now to FIG. 9, the large arrows "A" indicate the direction of flow of the material to be processed as it is introduced through the feed screw conveyor 326 and through a cylindrical spout 327 onto a trough 328 which uniformly distributes the particularized wood in each of the baskets in the first section 312 as the trough 328 is rotated in a circular path above the baskets. Each of the extractor sections or stages is constructed essentially the same with a cylindrical wall 330 forming the outer housing of the apparatus and an inner cylindrical concentric wall 332. Between these walls extend a plurality of vertically disposed radially extending partitions 334 which form the plurality of bottomless baskets therebetween.

Immediately between the concentric cylindrical walls 330 and 332 is a disc-shaped screen assembly 340 formed of a plurality of pie-shaped screen segments 342 as shown in FIG. 11, for example, with an opening 344 approximately the extent of the bottoms of two of the baskets formed by the partitions 334. This permits the material being processed to be passed from one extractor section to another sequentially from each basket. Each screen assembly 340 is supported in the upper region of a cylindrical wall 346 which forms the outer wall of the miscella collection pan 350. The bottom of the collection pan 350 is formed by a conically-shaped downwardly and outwardly extending disc 352 which joins the bottom edge of cylindrical wall 346.

As best seen in FIG. 15, a plurality of small openings 354 are provided around the outer periphery of the collection pan 350 to permit the miscella to drain out of the collection pan and enter the miscella distribution system as described infra. A hopper 356 is formed in each of the miscella collection pans 350 by providing two vertically extending partitions 358 and 360 which extend from a central region of the pan outwardly to meet the cylindrical wall 346 to provide the pie-shaped opening of the hopper 356.

The bottom 352 of the pan 350 is interrupted at that point and the partions 358 and 360 extend downwardly through the bottom of the pan as best seen in FIG. 10 so that a trough is formed to direct the particularized wood being processed either into the subsequent basket or into the material removal section 320 in the case of the last stage. It is to be noted that the hoppers 356 in the sections other than section 318 are not seen in FIG. 9 since in the relative positions of the hoppers of the various sections, as shown by FIGS. 11 through 15, the hopper is in front of the section lines.

Referring again to FIG. 9, an annular ring 362 is welded to the outside cylindrical wall 346 and is provided with a plurality of stiffening webs 364. The annular ring 362 supports the miscella collection pan 350 and screen assembly 340 around the outer periphery of the pan. A plurality of roller assemblies 366 are mounted at equally angular spaced locations around the outer periphery of the apparatus with the annular ring 362 riding on the rollers 368 thereof. The support roller assemblies 366 are each mounted to a support plate 370 which, in turn, is welded to the side of a cylindrical wall 372 which extends completely around the juncture of adjacent extractor sections. This juncture area is enclosed by upper and lower annular rings 373 and 374 which are welded on their inside edges to the cylindrical walls 330 of the respective extractor section and welded at their outside edges to wall 372.

A cylindrical ring 376 is welded to and depends downwardly from the bottom 352 of miscella collection pan 350 and closely surrounds the upper edge of the cylindrical wall 330 of the next lower extractor section in order to prevent the miscella or material being processed from passing through the gap which would otherwise exist in this area.

A collection trough 378 is formed by the cylindrical wall 372 and annular ring 374 in the lower region of each of the extractor sections and receives miscella from the plurality of openings 354 defined in the lower portion of the collection pan 350. Miscella distribution pipes connect to the bottom of each of the troughs 378 which, for each extractor section, distributes the miscella to either a preceding extractor section or to a collection tank when the miscella is completely enhanced as is explained more fully infra.

The miscella or solvent is distributed over the upper portion of the baskets in each extractor section by a plurality of miscella distribution troughs 382 which extend radially outwardly at predetermined angular locations from a central cylindrical trough 384 as seen for each section in FIGS. 11 through 14. It is to be noted that the miscella distribution system for the first extractor section 312 is somewhat different in that the troughs 382 are connected to the central cylindrical trough 384 through interconnecting pipes 385 which also support the troughs 382. In the other sections, the troughs 382 are directly connected to the central cylindrical trough 384 as shown.

All of the miscella distribution troughs, screen assemblies 340 and miscella collection pans 350 are mounted to a central shaft 386 for rotation therewith. In addition, the material distribution trough 328 is also mounted to the upper end of shaft 386 for rotation therewith. The lower end of shaft 386 is supported in a hub 388 as shown in FIG. 10 which additionally supports the collection pan 350 and screen assembly 340 of the last extractor section 318. In this last section, the miscella collection trough 378 formed by the cylindrical wall 372 and upper and lower annular rings 373 and 374 is somewhat expanded in order to accommodate a ring gear 390 which is supported by an also expanded annular ring 362, for rotation therewith. The gear reduction unit 324 and motor 322 then, through a pinion gear 392, rotates the ring gear 390 which thus simultaneously rotates all of the miscella distribution troughs, screen assemblies and miscella collection pan.

Referring now to the material removal stage 320, the hopper 356 in the last extractor stage 318 empties directly into a conical chute 394 which directs the material towards a horizontally extending pair of miscella extraction screws 396 and 398 which convey the material out of the apparatus. In doing so, however, the extraction screws 396 and 398 are so designed and positioned that they tend to squeeze the material (the particularized wood) to thus remove further miscella (extract) therefrom. The miscella passes through the screen surface 400 beneath the screws and is collected in a further collection trough 402 from which it is removed by a miscella distribution pipe 404 and pumped by pump 405 into miscella collection trough 378 of the last stage 318. Thus additional miscella (extract) is removed from the material than would otherwise be the case if it were dumped into the hopper and simply removed. It is contemplated that other means may be utilized for removal of the material from beneath the conical chute 394 such as a single feed screw or mechanical picker.

Referring now to the miscella collection and distribution system as shown in FIGS. 9 and 10, the pure solvent such as n-hexane, is introduced through a pipe 406 into the miscella distribution trough 384 from which it then passes into the individual miscella distribution troughs 382. As the troughs 382 overfill, the miscella cascades over the sides of the troughs and is thus applied to the upper surface of the material (the particularized wood, e.g. the particularized *Juniperus Mexicana* being processed in each of the baskets as the troughs 382 are rotated by the shaft 386.

As the thus applied solvent (e.g. n-hexane) passes through the material, it extracts the high thujopsene-containing cedarwood oil from the particularized wood and passes through the screen assembly 340 beneath the bottom of the baskets and is collected in the collection pan 350. It then passes through the openings 354 in the bottom of the collection pan 350 and enters the cylindrical collection trough 378 beneath the last stage extractor 318. From there, it passes into the pipe 408 and is pumped by pump 410 up to the upper region of the previous extraction stage 316 where it is introduced into the cylindrical miscella distribution trough 384 and hence through the troughs 382 onto the material in the baskets. This miscella, as it passes through the material in the baskets is again further enhanced and collected in the collection pan 350 where, as before, it passes into the collection trough 378.

This now-enhanced miscella is taken through the pipe 412 and pumped by pump 414 up to the next previous stage, as shown in FIG. 9, through pipe 416 and is introduced into the upper region of extractor stage 314 through the central cylindrical miscella distribution trough 384 and the individual distribution troughs 382. As before, it passes through the beds of particularized wood, e.g. particularized pre-treated *Juniperus Mexicana* previously treated with, for example, the compound having the structure:

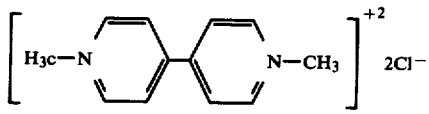

and becomes further enhanced and is then subsequently pumped to the first stage through pipe 418 and distributed over the particularized wood substance as before. The miscella from the first stage is then removed to a distillation system (not shown) through pipe 419. This distillation system is, however, set forth in FIGS. 4, 5, 6 and 7 as apparatus indicated by reference numeral "126" through pipe 419.

The sections of the device shown in FIGS. 11 through 14 show that each of the sets of miscella distribution troughs 382 are in a specific relationship relative to those in the other stages, which is important in processing the particularized wood substance, e.g. *Juniperus Mexicana*, through the apparatus of the present invention. As shown in FIG. 11, the five miscella distribution troughs 382 are positioned at equal angular locations behind the material distribution trough in the direction of rotation, which is counterclockwise as viewed. Likewise, the screen assemblies 340 and the openings 344 therein are in a specific relation between the various stages with the opening 344 being in advance of the material distribution trough in the first stage and being in the other stages in advance of the opening in the subsequent immediately following stage.

As material is being introduced through the material distribution trough into a basket as illustrated in FIG. 11, in the first stage, the previously filled baskets are being treated with the previously enhanced miscella. The last distribution trough 382 is somewhat in advance of the opening 344 in the screen so as to permit the miscella to drain through the material being processed before the opening 344 allows the material to pass into the basket in the subsequent stage positioned immediately below the basket being emptied. When the opening 344 in the first stage screen assembly is positioned as illustrated in FIG. 11, the opening 344 in the screen assembly of the second stage is positioned as illustrated in FIG. 12 so that the screen in the second section will cover the bottom of the basket in which the material being processed is received from the first extractor section.

It is also to be noted that the troughs 382 in FIG. 12 have not yet reached the position where the particularized wood material is being passed from the first stage to the second, in order that it does not interfere with the passage of the material. Also, it is to be noted that the opening in the screen of the second stage immediately precedes, in the direction of rotation, the opening in the screen of the first stage so that the material in the second stage is being dumped just prior to new material (particularized wood) being received from the first stage. All subsequent stages are similarly aligned in regard to the openings 344 in the screen assemblies as well as the positioning of the miscella distribution troughs 382 so that material is fully processed and the miscella removed through each cycle of rotation of the miscella distribution trough, material distribution trough and screen assemblies.

It is to be noted that the hoppers 356 in each of the collection pans 350 remain in alignment with the openings 344 in each of the screen assemblies in order to permit the material to be passed from one basket to a subsequent one in vertical registry therewith.

FIGS. 16-24 inclusive illustrate a multi-stage internal mixer-settle extraction apparatus particularly useful in carrying out the process of our invention as illustrated in FIGS. 4, 5, 6 and 7, supra.

In those figures, such apparatus is specifically referenced using reference numeral "102". Such apparatus is specifically described in U.S. Pat. No. 2,665,196 issued on Jan. 5, 1954, the specification of which is incorporated by reference herein.

Referring to FIGS. 16–23, the liquid/liquid extraction apparatus 102 comprises a vertically disposed cylindrical vessel 510 having a circular access port 511 concentric with the cylinder, in one head 512 which is closed by cover plate 513 (FIG. 23) bearing axially disposed rotor shaft 514 and the core assembly to be described infra. A heavy phase inlet (e.g. the aqueous phase to be extracted using such solvent as diethylether) 515 is provided near the top of the cylinder 510 and a light phase inlet (the solvent extraction material, that is, diethylether or the like) 516 is provided near the lower end thereof. A heavy phase outlet 517 is provided in the bottom of the vessel and a light phase outlet 518 is provided in the top. An even number of horizontal plates 519 is spaced along the cylinder 510 dividing the latter into an odd number of compartments. Each plate 519 has a central opening 519a, all of uniform size and no larger than access port 511, for insertion and removal of the core assembly. In the embodiment shown in FIG. 16, plates 519 have the same diameter as the interior of cylinder 510 and each plate has a plurality of perforations 520 near its periphery to serve as interzonal fluid passageways. In the embodiment shown in FIG. 18, the inwardly directed risers 522 and downcomers 523 serve to direct liquid flow toward the center of the cylinder. The plates shown in FIG. 19 are of slightly smaller diameter than cylinder 510 to provide peripheral passageways 524 and horizontal rings 525 cooperate with these passageways for the same purpose. In the last described embodiment, tie rods or brackets are needed to hold the plates 519 in position, but these have been omitted from FIG. 19 for clarity. In FIGS. 16, 18 and 19, the cylinder 510 is illustrated as having settling chambers "S" about twice the height of the mixing chamber "M". This proportion is not critical but it is preferable that the settling zones be deeper than the mixing zones. In the taller multiple stage extractors, it is desirable to provide three or more guide rails 526 disposed symmetrically about the axis of the cylinder 510 and set flush with the edge of the central openings in plates 519 to facilitate insertion and removal of the core assembly. A bearing 527 is provided in the normally closed end of cylinder 510 coaxial with the cylinder to receive the end of rotor shaft 514 when the core assembly is in place.

Rotor shaft 514 passes through an axial bearing 528 in cover plate 513 and axially through the core assembly shown in FIG. 20. A plurality of tie rods 529 passes through cover plate 513 and supports a series of discs 530 in horizontal planes spaced so as to coincide with the planes of plates 519 when the core assembly is positioned in the cylindrical shell. Each of the discs 530 is centrally bored for free rotation of the shaft 514 and to provide a small annular passageway 531 (FIG. 22) for flow of liquid along rotor 514 from one side of each disc 530 to the other. Discs 530 are all of the same diameter, just slightly smaller than the diameter of the central openings 519a in plates 519, to leave a small annular passageway 532 (FIG. 23) for flow of liquids from one side to the other of plates 519 and discs 530. The face of each disc 530 which is directed toward a settling chamber "S" may carry a plurality of radially disposed vertical vanes 533 to serve as baffles for damping any swirling action in the liquids in such chambers, or such baffle vanes may be similarly disposed in the settling chambers on supports other than discs 530. The baffle vanes 533 may be attached at their inner edges to axial bearings 534 for shaft 514. In each of the mixing chambers, a plurality of radially disposed vertical impeller blades 535 is mounted for rotation on shaft 514, the combined radial lengths of each blade 535 and its supporting member 536 being short enough to permit rotation without interference from tie rods 529. The supports 536 for impeller blades 535 may be radial arms, as illustrated in FIG. 22, or they may be discs mounted for rotation with shaft 514.

The apparatus of FIGS. 16-23 may be built with as many or as few mixing and settling zones as desired and the core assembly may be removed and replaced readily through the access port 511.

The apparatus 102 may be operated with either the heavy liquid or the light liquid as the disperse phase. By adjusting the rate of withdrawal of the heavy liquid, a single fixed liquid-liquid interface can be maintained at any desired level in the system. Above the interface, the light liquid (e.g. the diethylether extracting agent) is the continuous phase and below it the heavy phase (the aqueous phase or other phase evolving out of the solid/liquid extraction vessel or the liquid phase of the condensate from the steam distillation apparatus) is the continuous phase. The control interface is most commonly maintained in one of the end settling compartments in the diagram of FIG. 24. The interface 540 is shown in the uppermost settling chamber and the light liquid (the solvent for extraction) is the disperse phase through all of the rest of the column as illustrated by the rising droplets 541.

In operation, the extractor of FIGS. 16-24 is nearly filled with the liquid which is to be the continuous phase. Enough of the other liquid is introduced to complete the filling of the extractor of FIGS. 16-24. The rotor shaft 514 and its supported impeller blades 535 are set in motion and the two liquids are introduced through their respective inlets 515 and 516 at the desired rates. The light layer overflows freely or through the pressure control valve (not shown) and the heavy layer is withdrawn at a rate that will maintain interface 540 at the desired level. Assuming the light liquid is the disperse phase, as illustrated, it rises from inlet 516 and tends to a layer beneath the nearest plate 519 and disc 530. The outward thrust of impellers 535 in the adjacent mixing chamber draws the light liquid upward through the passageways 531 and 532 and some of the heavy liquid from the next higher settling zone is simultaneously drawn down through similar passageways 531, 532 into the same mixing zone where redispersion occurs. The mixed liquids are impelled outwardly toward the periphery of cylinder 510 and part of the mixture is displaced downwardly through passageways 520, 523 or 524 while the rest of the mixture is displaced upwardly through passageways 529, 522 or 524 into adjacent settling chambers. Radially disposed vertical baffles 533 and, if desired, similar baffles in the cylindrical shell, minimize the surging and haphazard recirculation of the continuous phase, and the liquids separate again into layers along the surfaces of plates 519 and discs 530 in the settling chamber. The heavy layer is drawn down through passageways 531, 532 into the next lower mixing chamber while the light layer is drawn up through similar passageways into the next higher mixing chamber. The process repeats itself continuously, with the light phase finally layering below the outlet port 518 in the uppermost chamber while the heavy phase settles above outlet 517 in the lowermost chamber. The settled heavy and light phases are withdrawn through outlets 517, 518 at the respective rates at which they are being introduced through inlets 515, 516, modified only by the volume change accompanying the extractive interchange between the phases during their counterflow through the extractor. End-to-end flow through the extractor is prevented principally by the liquid velocities induced through interzonal passages 531, 532 at the suction side of the mixers and through interzonal passages 520, 522, 523, 524 on the discharge side of the mixers. Rotor shaft 514 is driven at a sufficient speed to induce velocities at these points which prevent counterflow. End-to-end flow along rotor shaft 514 may be prevented further by mounting impeller blades 535 on horizontal discs secured axially to shaft 514. During its traverse of the system, each particle of the disperse phase is collected and redispersed many more times (from 2 to 10 or more) than the number of mixing stages due to the large volume handled at each stage relative to the volumes of the two phases fed to the extractor of FIGS. 16–24 inclusive.

In a specific example, a small 8-stage extractor is constructed in accordance with the disclosure of U.S. Pat. No. 2,665,196, the specification of which is incorporated by reference herein, having a 4" core assembly and 6" diameter settling sections. A brine mixture containing 2.44% by weight of high thujopsene-containing cedarwood oil is introduced as the continuous phase through inlet 515 at the rate of 1.1 gallons per minute and diethylether is introduced through inlet 516 at the rate of 0.275 gallons per minute. The diethylether becomes the disperse phase. The impellers are driven at 240 revolutions per minute. The exit brine withdrawn through port 517 contains at most 0.0033% high thujopsene-containing cedarwood oil while the diethylether extract withdrawn through port 513 contains 7.28% by weight of high thujopsene-containing cedarwood oil. The stage efficiency is about 75%.

A similar extractor is constructed with two stages, the impellers being 4" in diameter, the core assembly 6" in diameter and the settling sections 15" in diameter. A similar brine-high thujopsene-containing cedarwood oil feed is used, countercurrent to diethylether at rates of 1.5 gallons per minute of brine and 0.5 gallons per minute of diethylether. Counterflow through the interzonal ports is prevented and optimum extraction occurs with a rotor speed of 240 revolutions per minute. Analysis of the inlets and outlets shows:

TABLE III

|  | Percent high thujopsene-containing cedarwood oil by weight |
|---|---|
| Incoming brine | 2.44 |
| Exit brine | 0.12 |
| Exit diethylether | 4.82 |

FIGS. 25, 26, 27A and 27B illustrate another embodiment of the liquid-liquid extraction apparatus which could be used in the process of our invention as shown in schematic form in FIGS. 4, 5, 6 and 7. The liquid-liquid extractor apparatus is shown using reference numeral "102". This apparatus is specifically described in U.K. Patent Specification No. 1,324,261 published on July 25, 1973, the specification for which is incorporated by reference herein.

With reference to FIG. 25, reference numeral "601" denotes an inlet port through which the liquid mixture of solvent, e.g. benzene or diethylether, and a denser liquid, in this case, the aqueous phase evolving from the steam distillation apparatus, for example, is supplied to the separator. Port 601 is offset with respect to a chamber 602 so that a swirling motion is given to the liquid in a vertical circular trunk pipe 603; such a motion assists in the separation of the organic phase from the aqueous phase.

When the liquid reaches the top of the pipe 603, it enters the tank 605 flowing in a radial direction where rough separation takes place when the organic phase globules cling to the underside of the fixed perforated (or slotted) header plate 606a and after growing in size, ultimately percolate into the header tank or cover 607.

This header tank 607 has a cover provided with a top access door 608 which (if necessary) carries a steam or hot water heating coil 616, if improved separation is required, or when the organic phase is too cold to flow freely.

After this rough separation, the organic phase (the solvent containing the high thujopsene-containing cedarwood oil) is guided downward and radially through a series of slotted ring-like separating plates 623 in a cascade fashion by means of a series of annular plates 604 and 604a disposed vertically one over the other. Plates 604 and 604a may be of cast iron, bronze or aluminum, alternatively of fabricated mild steel.

These annular plates are supported, one on top of the other, the bottom plate being supported on a circular cast or fabricated internal rib in tank 605. Plate 604 and 604a have integral, vertical frustro-conical funnels 625, each funnel being provided with a rib 624 internally at a predetermined height to support the guide plate immediately above it. Separated solvent-high thujopsene-containing cedarwood oil solution passes upwards through the frustro-conical funnels unimpeded by the motion of the rest of the liquid as it passes radially and downward through the separator.

The outer rims of plates 604 abut against the inside wall of tank 605 while the inner rims are spaced from trunk pipe 603. With plates 604a, the outer rims are spaced from the inside wall of tank 605 while the inner rims abut trunk pipe 603. The liquid as well as flowing radially, cascades downwards as indicated by the arrows through the spaces so defined, passing through the separating plates and the chambers formed by them and the plates 604 and 604a.

Thus, in its passage through the vessel, the liquid is guided through the separation slots on its downward path to the clean water outlet 610 on which is mounted a spring (or weight) loaded valve 620, maintaining a predetermined pressure in the tank 605 and the header tank 607.

The plates 604 and 604a have an inverted dished shape so that organic phase which collects on the vertical slotted ribs can travel circumferentially along the underside of the said plates and eventually rise freely through the frustro-conical funnels eventually entering the header tank or cover 607 through a pipe 606 incorporated in the header plate 606a. Any air collecting in header tank 607 is released through an air valve 611 connected by an open pipe 612 to a collector tundish 614, provided to catch any liquid "carryover".

Test cocks 613 are situated at suitable heights on header tank 607 to give approximate indication of separated organic phase level in header tank 607 and/or casing 605.

In operation, the organic phase containing the high thujopsene cedarwood oil which eventually collects in the upper part of header tank is released through a port 609 controlled by an electrically operated valve 619, the opening of which is controlled by the probes 617a and 617b inserted at different levels in the cover 607. The amount of opening of valve 619 can be controlled electronically by circuitry in the panel 618.

An alternative method of guiding the flow of the liquid through the separator is shown in FIGS. 26, 27A and 27B. In this case all the control plates 604b and 604c are of the same internal and external diameters but instead of spaces between plates 604a and 604 and the vessel 605 and the trunk pipe 603, respectively, as in FIG. 25, slots 621 and 622 are incorporated on the outer and inner sloping sides of the annular plates connecting the vertical frustro-conical funnels.

In each of the GLC profiles of FIGS. 28-54, the GLC conditions are: 10'×0.125" 5% Carbowax column programmed at 100°-230° C. at 4° C. per minute. Each of the GLC profiles indicates that whether the *Juniperus Mexicana* tree is treated with PARAQUAT ® solution or other bipyridylium solution or not, the thujopsene content of the cedarwood oil and the overall individual chemical composition of the high thujopsene-containing cedarwood oil is substantially unaffected.

FIG. 55 sets forth a schematic flow diagram of apparatus used in the prior art for obtaining high thujopsene-containing cedarwood oil from particularized *Juniperus Mexicana* trees. The *Juniperus Mexicana* trees at location 700 are processed from conveyor 701 at location 702 where green wood and aged wood (2 years aging) may be combined or may be used separately. The particularized green and aged wood of the Juniperus Mexicana is then treated in steam distillation apparatus 707 where steam taken alone or combined with ethanol, isopropanol or methanol in the vapor phase at atmospheric or super-atmospheric pressure is passed through valve 705 and line 706 (if desired through a superheater) through column (of the distillation apparatus) 707 whereupon the overhead vapor 708 is passed into condenser 709 wherein liquid 712 (the heavy phase) is removed and stored in 713 and overhead high thujopsene-containing cedarwood oil is passed through line 710 and collected in 711.

FIG. 56 illustrates laboratory apparatus used in simulating the commercial process for extracting high thujopsene-containing cedarwood oil from particularized *Juniperus Mexicana* particles. Thus, steam from source 901 is passed through line 902 into steam trap 904. Condensate is permitted to drain out through line 917 and the steam proceeds through line 905 into steam distillation apparatus 906. The steam is used in part to preheat the particularized high thujopsene-containing cedarwood chips which are located in column 907. The steam proceeds through outer annulus 909 through vacuum hose 908 and into column 907 through the high thujopsene-containing cedarwood chips (thermometer control 911). The overhead vapor is passed through line 910 into condenser 912 which is cooled using water passed through outer jacket 913 from inlet 914. The condensed two phases, the organic phase and the aqueous phase, are collected in separatory funnel 915 with the heavy phase being ultimately collected in flask 916.

FIG. 57 is a schematic diagram of a "control" Juniperus Mexicana tree used for the purposes of determining the concentration of high thujopsene-containing cedarwood oil in various parts of the *Juniperus Mexicana*, not treated with bipyridylium salts at any concentrations.

The stump of the control tree is indicated by reference numeral "801". The center part of the trunk portion of the *Juniperus Mexicana* above the stump and below the top is indicated by reference numerals "801A", "801B", "801C", "801D", and "801E". The lower branches of the control *Juniperus Mexicana* is indicated, in general, by reference numeral "804" and specifically by reference numerals "802", "803", "804A", "804B", "804C", "805A", "805B", "806A", "806B" and "807". The middle branches are indicated by reference numeral "805" in general, and specifically by reference numerals "808-1-A", "808-2-A", "808D", "808-3", "808A", "808B", "808C", "809A", "809B", "809C", "810A", "810B", "811A", "811B", "812A", "812B", "813A", "813B", "814A", "814B".

FIGS. 58, 59, 60, 61, 62, 63, 64 and 65 set forth in schematic form, a preferred method of preparing a treatment site on the *Juniperus Mexicana* for treatment with the bipyridylium salt composition of matter defined according to one of the structures:

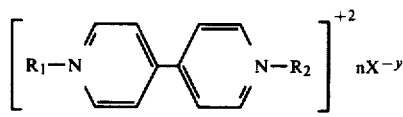

and/or

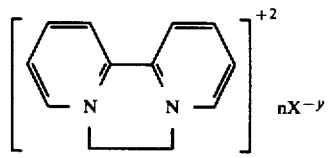

taken alone or further together with another treatment material such as an ethylene-producing material as disclosed in U.S. Pat. No. 4,203,253 issued on May 20, 1980, the specification of which is incorporated by reference herein. An example of an ethylene-releasing chemical which can be used in combination with the bipyridylium salt is 2-chloroethylphosphonic acid. Other examples of ethylene-producing materials are as follows:

ethylhydrazine
beta-hydroxyethylhydrazine
sym-diethylhydrazine
unsym-bis-(2-hydroxyethyl)hydrazine
aminomorpholine
2-hydroxy-N-(2-hydroxyethyl)carbazinate
2-(2-hydroxyethyl)semicarbazine
ethylpropyl phosphonate
monoethyl sulfate
2-chloroethylphosphonic acid as set forth at column 3, lines 50-60 of U.S. Pat. No. 4,203,253.

Referring to FIG. 58, there are shown four distinct layers of a living *Juniperus Mexicana* 1010, each of which plays a particular role in the life of a *Juniperus Mexicana*. Outer bark 1012 insulates the *Juniperus Mexicana* from extreme heat and cold, helps keep out rain and protects the *Juniperus Mexicana* against insects. Phloem 1014 conducts food from leaves of the *Juniperus Mexicana* to the rest of the *Juniperus Mexicana*. Cambium layer 1016 produces a new bark, a new wood annually in response to hormones which stimulate the growth of cells. Sapwood 1018 is the pipeline for water moving from roots to the leaves. When its inner cells lose their vitality, they turn into heartwood. Heartwood 1020 is the central supporting column of a mature Juniperus Mexicana. It will not decay or lose strength as long as the outer layers of the *Juniperus Mexicana* remain intact.

While heartwood is present in mature *Junperus Mexicana*, *Juniperus Mexicana* used may contain a large amount of heartwood (aged trees) or little heartwood (green trees). To produce high thujopsene-containing cedarwood oil, either the green trees containing little heartwood or the aged trees containing a large amount of heartwood may be used. The interior portion of the *Juniperus Mexicana* adjacent the cambium layer will consist essentially of sapwood. Thus the *Juniperus Mexicana* preferred for treatment in our invention will be from about 20 up to about 80 years old, will be from about 5 up to about 40 feet tall and will have a cross-sectional outer diameter of at least about 20 inches in breast-height.

FIG. 59 is a view section of the bole section 1030 of a *Juniperus Mexicana* showing a single treatment site 1032. Treatment site 1032 consists of elongated hole 1034 filled with fibrous material 1036. FIG. 59 shows axis 1038 of the elongated hole 1034 at its preferred vertical angle of 30°.

Figure 60:
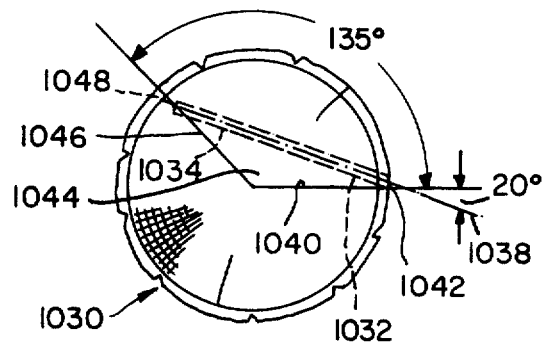

FIG. 60 shows the axis 1038 of elongated hole 1034 at its preferred angle of 20° to entry end including radial plane 1040 that includes axis entry end 1042 of the elongated hole axis 1038. As shown elongated hole 1034 is of a length such that the sector angle of deposition sector 1044 is 135°. Deposition sector 1044 is that area included by entry end included radial plane 1040 and terminal end included radial plane 1046. Terminal end included radial plane 1046 includes axis terminal end 1048 of axis 1038.

Figure 61:
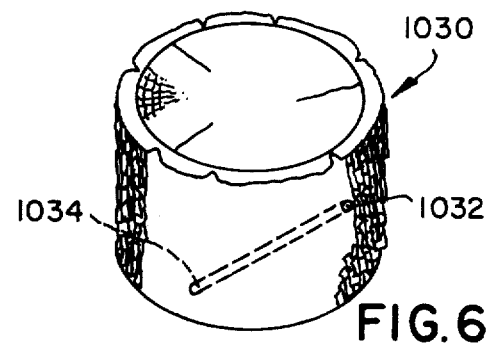

FIG. 61 is a view in perspective of bole 1030 showing the treatment site 1032 which includes elongated hole 1034.

FIGS. 62 and 63 are similar to FIGS. 60 and 61, respectively, and show the preferred embodiment when two treatment sites are employed to provide two deposition sectors. Shown in the bole section 1050 are two treatment sites 1052 and 1054. A deposition sector 1056 having a sector angle of 90° is created by treatment site 1052 and a deposition sector 1058 having a sector angle of 90° is created by treatment site 1054. While not shown, the axis of the elongated hole of each treatment site will be at its preferred vertical angle of about 30°. Each horizontal angle, as shown, is 40°.

FIGS. 64 and 65 are similar to FIGS. 62 and 63, respectively, and show the preferred embodiment when three treatment sites are employed to provide three treatment sectors. Shown in bole section 1060 are three treatment sites 1062, 1064, 1066 which provide, respectively, deposition sectors 1068, 1070 and 1072, each deposition sector having a sector angle of 60°. While not shown, the axis of the elongated hole of each treatment site will be at its preferred vertical angle of about 30°. Each horizontal angle, as shown, is 30°.

FIG. 66 is a schematic diagram of solid-liquid extraction apparatus which can be used in place of the steam distillation apparatus or solid-liquid extraction apparatus discussed supra. This solid-liquid extraction apparatus is useful as apparatus indicated on FIGS. 4, 5, 6 and 7 by reference numeral "95".

The apparatus is a "Soxhlet" type apparatus as specifically described in U.S. Pat. No. 1,636,550, the specification for which is incorporated herein by reference. Specifically, in FIG. 66, the numeral "2001" designates a holder for the particularized *Juniperus Mexicana* wood taken alone or mixed with other particularized wood which is shown at 2002 in the drawing. Arranged below the holder is a vaporizing apparatus for the solvent, e.g. freon, which apparatus consists preferably of a closed container 2003 arranged in a water bath vessel 2004. Heat may be applied to vessel 2004 either by gas flame, steam coils located in the vessel, solar energy or any other suitable means. Connected with the holder 2001 is a condenser 2005. The condenser 2005 may be of any suitable construction. It is shown as consisting of a vessel provided with two interior headers 2006 and 2007 having a plurality of condensing tubes 2008. The space between the headers is supplied with a cooling fluid by means, for example, of a cold water inlet pipe 2009. 2010 is an outlet pipe for cooling fluid which fluid may, if desired, be artifically cooled before being introduced into the condenser to the extent necessary to completely condense the vaporized solvent to a temperature of 10° C. for example, although this temperature will necessarily vary with the pressure in the holder.

Reference numeral "2011" indicates a pipe for conducting the vaporized solvent from vessel 2003 into the upper portion of the holder 2001. Reference numeral "2012" indicates a pipe leading from the lower portion of the holder to the vessel 2003, preferably. It is desirable to form pipe 2012 with an upward bend 2013 whereby the solvent will be accumulated in the holder to a certain level, that is to say, above the body of material treated, that is, the particularized wood, treated before being discharged to vessel 2003. When the outflow from the holder is started, it is continued siphonically until the holder is emptied of liquid so that the action is intermittent.

Evacuating mechanism is provided for maintaining a constant sub-atmospheric pressure in the holder, condenser and vaporizing vessel 2003. For example, a vacuum pump 2014 may be connected by pipe 2015 to the top of the condenser 2005. The method of extraction applied to the treatment of the particularized wood, e.g. the particularized *Juniperus Mexicana* wood, and using the apparatus as above described is as follows:

The particularized wood, e.g. *Juniperus Mexicana* wood chips, are comminuted and placed in the holder 2001 and allowed to stand under a mixture of ethyl alcohol and n-hexanol for 72 hours more or less. The alcohol mixture may be used in an amount approximating 55% by volume of the particularized wood.

After the particularized wood has been macerated, in this manner, as long as necessary, a volume of alcohol as above stated, preferably equal at least to the volumetric contents of the holder 2001 is placed in vessel 2003 and the water in vessel 2004 is heated to 40°-45° C. to bring about vaporization of the alcohol mixture. At the same time, the vacuum pump 2014 is started. The pump is operated so as to maintain a constant vacuum in the apparatus of approximately 4 mm/Hg pressure.

The vaporized solvent passes from vessel 2003 through pipe 2011 into the space 2016 above the material 2002 in the holder and into the condenser 2005. Coming in contact with the water cooled tubes 2008, the vapor is condensed and is refluxed upon the particularized woods treated. As soon as the level of the liquid in the holder rises above the upper bend of siphon 2013, the solvent with extractive matters, e.g. high thujopsene-containing cedarwood oil, from the particularized wood is drawn from the bottom of the holder and discharged into vessel 2003 by the siphoning action described. The vaporization of the solvent and its condensation and precipitation on the material treated is continuous so that the extracting operation may be carried on as long as may be necessary in order to remove the extractives, e.g. the high thujopsene-containing cedarwood oil, from the particularized wood to the extent desired. Ordinarily, the vaporization and condensation of the solvent will not keep pace with its discharge through the siphon so that the operation of the apparatus so far as withdrawal of the solvent and extraction is concerned, will be intermittent. That is, a certain amount of the solvent will collect and remain in contact for a time with the particularized wood and then will be discharged, the holder being practically emptied of liquid before the siphoning action is stopped.

When utilizing the apparatus of FIGS. 4, 5, 6 and 7, the apparatus element indicated by reference numeral "94" is a steam distillation apparatus, the variables for low pressure steam distillation as specified particularly in U.S. Pat. No. 3,542,755 issued on Nov. 24, 1970, may be utilized in our process. Accordingly, the specification of U.S. Pat. No. 3,542,755 issued on Nov. 24, 1970 is hereby incorporated by reference herein.

In further illustration of this invention, the following examples are given. The instant invention should not be limited to these examples but is only limited by the scope of the claims set forth infra.

A summary of the results of Examples I, II and III is as follows:

i. The treatment of *Juniperus Mexicana* with 1% solution of the compound having the structure:

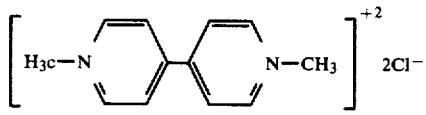

using the method of U.S. Pat. No. 3,971,159, the specification of which is incorporated by reference herein, results in a 60-90% increase in high thujopsene cedarwood oil.

ii. Spraying the foliage with a solution containing 0.3% of the compound having the structure:

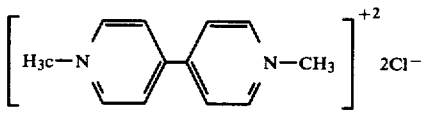

results in an 80-100% increase in high thujopsene-containing cedarwood oil within 6 months.

iii. There is no apparent change in the chemical composition of the oil whether the *Juniperus Mexicana* is treated or not with the compound having the structure:

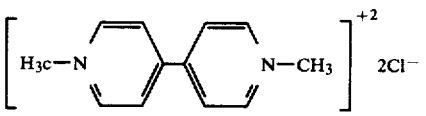

iv. The amount of high thujopsene-containing cedarwood oil is increased still further when using 2-chloroethylphosphonic acid in addition to the compound having the structure:

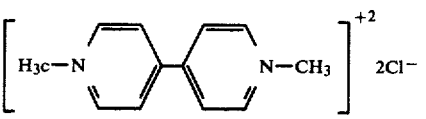

In each of Examples I, II and III, 100 grams of ground heartwood from each segment of the *Juniperus Mexicana* is subjected to a super-heated steam distillation (steam inlet temperature 135° C.; steam outlet temperature 110° C. at 4 psig for 6 hours). During distillation, the steam condensate is saturated with sodium chloride and extracted using diethylether.

After separation, the organic layer is dried over anhydrous magnesium sulfate and extracting solvent is removed under reduced pressure at 50° C. until the resulting high thujopsene-containing cedarwood oil is brought to constant weight. The oil layer is then combined with the evaporated ether extract layer and the high thujopsene cedarwood oil content is determined based on the total weight of fresh cut wood.

EXAMPLE I

Comparison of Treated Versus Untreated *Juniperus Mexicana*

Example I(A)

Using the procedures set forth above, and using the apparatus of FIG. 56, high thujopsene cedarwood oil was recovered and distilled at 86°-144° C. vapor temperature, 110°-212° C. liquid temperature at 1.0 mm/Hg pressure in a Vigreux column. The *Juniperus Mexicana* used was commercial Juniperus Mexicana. From 100 grams of high thujopsene cedarwood oil entering the distillation column, 94.7 grams is recovered causing there to be a 5% residue.

Example I(B)

Untreated *Juniperus Mexicana* trees, section 801C, section 801B, section 803, section 804A, section 801D, section 801B, section 804B, section 804C, section 801D are combined and the resulting high thujopsene cedarwood (see references made to FIG. 57) is distilled. The distillation conditions are: 70°-90° C. vapor temperature, 105°-210° C. liquid temperature and 1 mm/Hg pressure. The distillation is carried out on a micro-Vigreux column. The yield is 89.1% with a 11% residue. Thus, 15.6 grams is the starting material and 13.9 grams are distilled.

Example I(C)

Tree "49" treated with 1% aqueous PARAQUAT ® (having the structure:

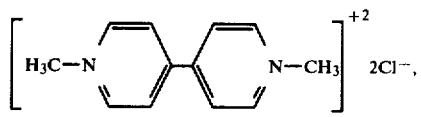

is stripped. The heartwood is ground into a powder which is steam distilled at the above conditions. The high thujopsene-containing cedarwood oil is then fractionally distilled at 67° C. vapor temperature, 89° C. liquid temperature and 1.0 mm/Hg pressure. The distillation is carried out on a micro-Vigreux column. 13.2 grams is recovered leaving a 15% residue (starting material 15.6 grams to be distilled).

EXAMPLE II

Comparison of Sections of Untreated *Juniperus Mexicana* Trees as Shown in FIG. 57

A tree as shown in FIG. 57, untreated with any bipyridylium salts, is cut up and each of the sections is processed using the foregoing procedure and using the apparatus of FIG. 3.

100 grams of *Juniperus Mexicana* wood is chopped up into chips having an average diameter of 1 mm. The chips are charged to the 19" jacketed glass column 44. The chips are indicated by reference numeral "45" in FIG. 3. Using a Thermowatch apparatus, steam at a temperature of 150° C. (super-heated steam) at 3 pounds per square inch gauge pressure is charged to column 44 through three-neck flask 42, heated using heating mantle 41.

Six one-liter fractions of water are collected from the continuous extractor 52 to which saturated sodium chloride from source 60 and diethylether from source 57 are added. During each extraction, approximately 250 grams of sodium chloride and 500 ml of diethylether are added.

After six liters of water are collected, the diethylether layers from the jacketed separatory funnel 62 and the separatory funnel 52 (below the Bidwell trap 51) are combined, dried and concentrated on a rotary evaporator yielding 3.8 grams of oil.

The oil is then distilled at 100° C. vapor temperature, 140°-145° C. liquid temperature and a vacuum of 3.0-4.0 mm/Hg on a 2" packed column.

The following examples relate to the following tree sections of FIG. 57 having the following GLC profiles (Figure numbers) (GLC conditions: 10'×0.125" 5% Carbowax column programmed at 100°-230° C. at 2° C. per minute):

| Example Number | Section of FIG. 57 | GLC Figure Number |
|---|---|---|
| II(A) | 809A | 35 |
| II(B) | 809B | 36 |
| II(C) | 809C | 37 |
| II(D) | 814A | 38 |
| II(E) | 814B (inner heartwood) | 39 |
| II(F) | 814B (outer heartwood) | 40 |
| II(G) | 814B (heartwood) | 41 |
| II(H) | 804B (heartwood) | 42 |
| II(J) | 804C (heartwood) | 43 |
| II(K) | 801 (stump) | 44 |

EXAMPLE III

Results of Treatment of *Juniperus Mexicana* with Paraquat ®

In each of Examples III(A)-III(K) aqueous solution of PARAQUAT ® having the structures:

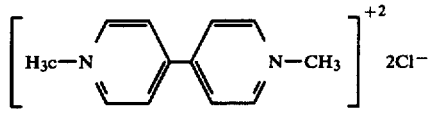

is applied to 20-30 year old, 15-20 foot tall, *Juniperus Mexicana* trees.

Using the above procedure, the following results were obtained (and compared with the high thujopsene content cedarwood oil obtained from untreated trees):

A. Untreated Trees

TABLE IV

| Section | Percent Oil |
|---|---|
| Bottom | 4.8 |
| Middle | 4.1 |

TABLE IV-continued

| Section | Percent Oil |
|---|---|
| Top | 3.3 |
| Branch, lower | 4.4 |
| Branch, middle | 4.3 |
| Branch, top | 3.4 |

B. Treated Trees

According to Example III, trees are treated with various levels of PARAQUAT ® and the oils analyzed. In those trees numbered 11',12' and 49' with average moisture content being 10%, the following results were obtained:

TABLE V

| Tree Number | Section | Percent High Thujopsene Cedarwood Oil |
|---|---|---|
| 11' | Bottom | 7.8 |
| 11' | Top | 7.5 |
| 12' | Bottom | 9.4 |
| 12' | Top | 8.3 |
| 49' | Bottom | 8.3 |
| 49' | Middle | 6.7 |
| 49' | Top | 6.4 |
| 49' | Branch (lower) | 7.3 |

When the bark of the main trunk of Tree number 67' is sprayed with a 1% PARAQUAT ® solution until it is entirely wet, 6 months after treatment, assay shows an oil content in the bottom trunk of 5.8%.

When the foliage of Tree number 56' is sprayed with a 0.3% PARAQUAT ® solution until all the branches are saturated, 6 months after treatment, assay shows the following percent of high thujopsene-containing cedarwood oil in the sections of said Tree number 56':

TABLE VI

| Section | Percent High Thujopsene-Containing Cedarwood Oil |
|---|---|
| Bottom | 9.7 |
| Top | 9.0 |
| Branch (middle) | 8.0 |

In Examples III(A)-III(K), the following tree numbers were treated with the following percentages PARAQUAT ® in the following stated manners yielding the GLC profiles of high thujopsene-containing cedarwood oil as set forth in the following Figure numbers:

| Example Number | Tree Number | PARAQUAT ® Concentration and Treatment Method | Figure Number | Percent Yield High Thujopsene Containing Cedarwood Oil |
|---|---|---|---|---|
| III(A) | 49' (base) | 1%, drilled, (U.S. Pat. No. 3,971,159 method) | 45 | 7.5 |
| III(B) | 49' (middle) | 1%, drilled | 46 | 6.1 |
| III(C) | 49' (top) | 1%, drilled | 47 | 5.8 |
| III(D) | 49' (branch) | 1%, drilled | 48 | 6.6 |
| III(E) | 11B' | 1%, drilled | 49 | 7.0 |
| III(F) | 11' (top) | 1%, drilled | 50 | 6.8 |
| III(G) | 13B' | 1%, drilled | 51 | 8.5 |
| III(H) | 812' (top) | 1%, drilled | 52 | 7.5 |
| III(J) | 35B' | 0.2%, drilled | 53 | 3.9 |

-continued

| Example Number | Tree Number | PARAQUAT ® Concentration and Treatment Method | Figure Number | Percent Yield High Thujopsene Containing Cedarwood Oil |
|---|---|---|---|---|
| III(K) | 52' (branch) | 0.2%, drilled | 54 | 4.5 |

The range of bipyridylium compounds without addition of any other material for use on *Juniperus Mexicana* is from about 0.25% up to about 3.5% of the bipyridylium salts having one of the structures:

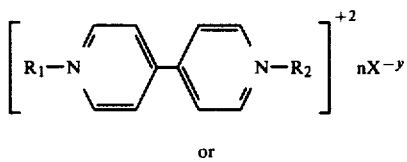

or

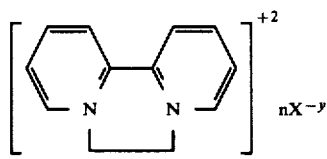

wherein $R_1$, $R_2$, X, n and y are defined supra. The tree, the *Juniperus Mexicana* may then be grown from $t=2$ months after treatment up to about $t=18$ months after treatment before cutting and extracting the high thujopsene-containing cedarwood oil therefrom. As will be seen in Example IV, when using an ethylene yielding material in addition to the bipyridylium salts having one of the structures:

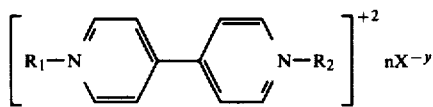

and

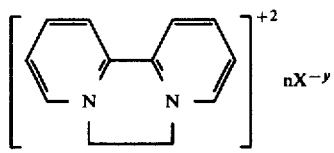

the concentration of bipyridylium salt may be as low as 0.1% to get a significantly higher yield of high thujopsene-containing cedarwood oil from the *Juniperus Mexicana* tree. Thus, when using a mixture of ethylene yielding compound, for example:

2-chloroethylsulfonic acid
beta-hydroxyethylhydrazine
ethylhydrazine
sym-diethylhydrazine
unsym-bis-(2-hydroxyethyl)hydrazine
aminomorpholine
2-hydroxy-N-(2-hydroxyethyl)carbazinate
2-(2-hydroxyethyl)semicarbazine
ethylpropyl phosphonate
monoethyl sulfate
2-chloroethylphosphonic acid.

EXAMPLE IV

Twenty year old, 15–20 foot *Juniperus Mexicana* trees are treated with mixtures of 300 ml of the following ethylene-yielding materials in combination with 0.1% solutions of PARAQUAT ® having the structure:

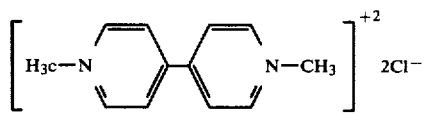

in accordance with the procedures specified in U.S. Pat. No. 3,971,159. The trees are then permitted to grow for periods of 3 months, 6 months and 12 months after treatment and are then cut and the resulting woods are particularized and processed using the process scheme as set forth in FIG. 3, supra. The resulting high thujopsene cedarwood oil content of the trees averages 8.5% and varies between 7% and 10%.

What is claimed is:

1. A method of chemically inducing the production of increased quantities of high thojopsene cedarwood oil within living *Juniperus Mexicana* trees by treating living *Juniperus Mexicana* trees with at least one bipyridylium salt having a structure selected from the group consisting of:

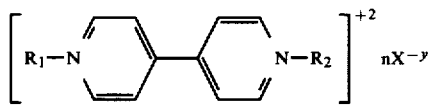

and

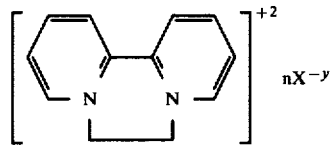

wherein $R_1$ and $R_2$ are the same or different and each represents $C_1$-$C_4$ lower alkyl; wherein $n=1$, $y=1$ and the product of n and y is 2 and wherein X represents chloride, bromide, fluoride, iodide, sulfate, nitrate, hydroxyl or methyl sulfate; permitting the so-treated *Juniperus Mexicana* trees to grow for a time of between 2 months and 18 months; harvesting the resulting *Juniperus Mexicana* trees; and extracting high thujopsene-containing cedarwood oil from the thus-harvested trees, the concentration of bipyridylium salt being between 0.15% and 40%.

2. The process of claim 1 wherein the bipyridylium salt is admixed with at least one ethylene-releasing agent.

3. The process of claim 1 wherein the bipyridylium salt has the structure:

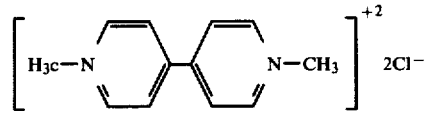

4. The process of claim 2 wherein the ethylene-releasing agent is selected from the group consisting of:

B-hydroxyethylhydrazine
Ethylhydrazine
Sym-diethylhydrazine
Unsym-bis-(2-hydroxyethyl)hydrazine
Aminomorpholine
2-hydroxy-N-(2-hydroxyethyl)carbazinate
2-(2-hydroxyethyl)semicarbazine
Ethylpropyl phosphonate
Monoethyl sulfate
2-chloroethylphosphonic acid.

5. The process of claim 1 wherein the bipyridylium salt composition is injected in a section of the *Juniperus Mexicana* tree at a location proximate the base of said tree.

6. The process of claim 1 wherein the bipyridylium salt composition is applied to the *Juniperus Mexicana* tree by spraying the foliage thereof.

7. The process of claim 1 wherein the bipyridylium salt is applied to the *Juniperus Mexicana* tree by spraying the bark thereof with a solution of said bipyridylium salt.

8. The process of claim 1 wherein the extraction of the high thujopsene-containing cedarwood oil from the harvested *Juniperus Mexicana* tree comprises the steps of:

(a) particularizing the *Juniperus Mexicana* wood;
 (b) steam distilling the thus particularized *Juniperus Mexicana* wood with super-heated steam;
 (c) condensing the steam distillate into two phases, an oil phase and an aqueous phase;
 (d) extracting the aqueous phase with an organic solvent;
 (e) evaporating the solvent from the solvent extract leaving an oil residue;
 (f) combining said oil residue with the oil phase of the steam distillate;
 (g) fractionally distilling the resulting combined oil phase.

9. The process of claim 1 wherein the extraction of the high thujopsene-containing cedarwood oil from the harvested *Juniperus Mexicana* tree comprises the steps of:

(a) particularizing the Juniperus Mexicana wood;
 (b) extracting the resulting particularized Juniperus Mexicana wood with a liquid organic extraction agent.

10. The process of claim 1 comprising the additional step of admixing with the harvested *Juniperus Mexicana* tree other harvested tree woods containing extractable oils other than or the same as high thujopsene-containing cedarwood oils.

11. The process of claim 1 wherein the step of extracting the high thujopsene-containing cedarwood oil from the thus harvested trees comprises the unit operation of steam distillation.

12. The process of claim 11 wherein the age of the *Juniperus Mexicana* trees is between 20 and 80 years.

* * * * *